US008496608B2

(12) United States Patent
Priplata et al.

(10) Patent No.: US 8,496,608 B2
(45) Date of Patent: Jul. 30, 2013

(54) SYSTEMS AND METHODS FOR TREATING OBESITY AND TYPE 2 DIABETES

(75) Inventors: Attila A. Priplata, Morristown, NJ (US); Joseph P. Errico, Green Brook, NJ (US); John T. Raffle, Austin, TX (US); Jonathan David Gardiner, Budd Lake, NJ (US)

(73) Assignee: E2 LLC, Morris Plains, NJ (US)

( * ) Notice: Subject to any disclaimer, the term of this patent is extended or adjusted under 35 U.S.C. 154(b) by 664 days.

(21) Appl. No.: 12/702,449

(22) Filed: Feb. 9, 2010

(65) Prior Publication Data

US 2011/0000496 A1 Jan. 6, 2011

Related U.S. Application Data

(63) Continuation-in-part of application No. 12/566,193, filed on Sep. 24, 2009, now abandoned, which is a continuation-in-part of application No. 12/508,701, filed on Jul. 24, 2009, now abandoned.

(60) Provisional application No. 61/239,506, filed on Sep. 3, 2009, provisional application No. 61/222,206, filed on Jul. 1, 2009.

(51) Int. Cl.
*A61M 5/00* (2006.01)
*A61F 2/04* (2006.01)

(52) U.S. Cl.
USPC .......................................... 604/8; 623/23.64

(58) Field of Classification Search
USPC ....................................................... 604/8, 9
See application file for complete search history.

(56) References Cited

U.S. PATENT DOCUMENTS

| | | | |
|---|---|---|---|
| 5,820,584 A | 10/1998 | Crabb | |
| 7,803,195 B2 * | 9/2010 | Levy et al. ................. | 623/23.68 |
| 2004/0092892 A1 | 5/2004 | Kagan et al. | |
| 2005/0085923 A1 * | 4/2005 | Levine et al. .............. | 623/23.65 |
| 2005/0096750 A1 | 5/2005 | Kagan et al. | |
| 2005/0192614 A1 | 9/2005 | Binmoeller | |
| 2005/0192629 A1 | 9/2005 | Saadat et al. | |
| 2005/0273060 A1 * | 12/2005 | Levy et al. .................... | 604/192 |
| 2006/0116736 A1 | 6/2006 | Dilorenzo | |
| 2008/0103604 A1 | 5/2008 | Levine et al. | |
| 2008/0262520 A1 | 10/2008 | Makower et al. | |
| 2008/0287969 A1 | 11/2008 | Tsonton et al. | |
| 2009/0182355 A1 * | 7/2009 | Levine et al. ................. | 606/153 |
| 2009/0198210 A1 | 8/2009 | Burnett et al. | |
| 2009/0247992 A1 | 10/2009 | Shalon et al. | |
| 2009/0259237 A1 | 10/2009 | Grau et al. | |

OTHER PUBLICATIONS

Rubino, et al. "Potential of surgery for curing type 2 diabetes mellitus", Annals of Surgery, (2002) vol. 236. No. 5: 554-9.*

(Continued)

*Primary Examiner* — Susan Su
(74) *Attorney, Agent, or Firm* — Joseph P. Errico

(57) ABSTRACT

The present invention provides systems and methods for treating wounds in patients who lack the innate ability to regulate glucose (e.g., diabetic patients). In one aspect of the invention, a method includes positioning an internal bypass device within the duodenum to inhibit contact between chyme passing therethrough and an internal wall of the duodenum and maintaining the internal bypass device within the duodenum for a sufficient period of time to decrease insulin resistance and reduce a blood glucose level in the patient. The internal bypass device increases peripheral blood flow and elevates an immune system response to accelerate healing of the wound.

20 Claims, 40 Drawing Sheets

OTHER PUBLICATIONS

Stansberry, et al. "Impairment of peripheral blood flow responses in diabetes resembles an enhanced aging effect", Diabetes Care, (Nov. 1997), 20(11): 1711-6.*

Lindenmeyer, et al. "Interstitial vascular rarefaction and reduced VEGF—a expression in human diabetic nephropathy", JASN, (2007) vol. 18 No. 6: 1765-76.*

Jakelic, et al. "Nonspecific immunity in diabetes: hyperglycemia decreases phagocytic activity of leukocytes in diabetic patients", Med. Arh. (1995), 49(1-2): 9-12.*

MedicineNet.com, "Hemoglobin A1c", (Mar. 12, 2007, obtained from Wayback Marchine).*

PCT International Search Report and PCT Written Opinion of the International Searching Authority for PCT application PCT/US2010/056789, Jan. 14, 2011.

PCT International Search Report and PCT Written Opinion of the International Searching Authority for PCT application PCT/US2010/055765, Jan. 5, 2011.

* cited by examiner

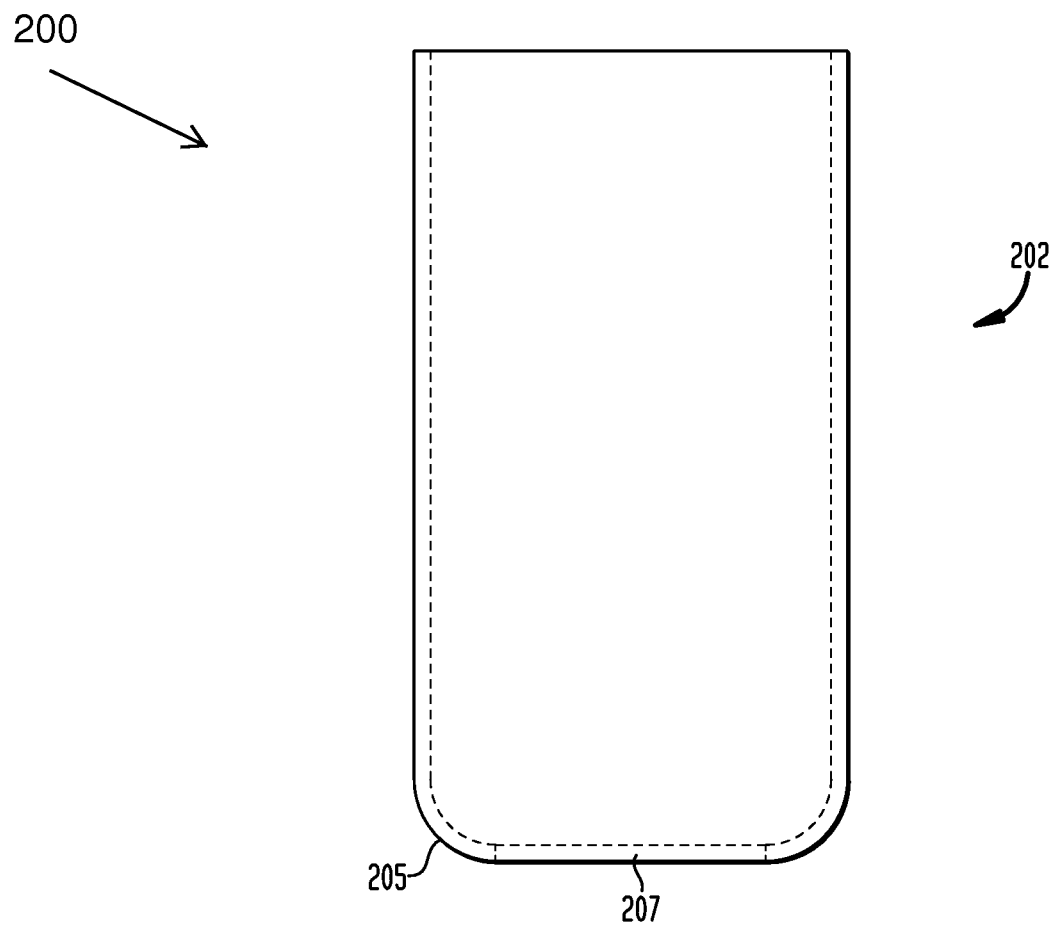

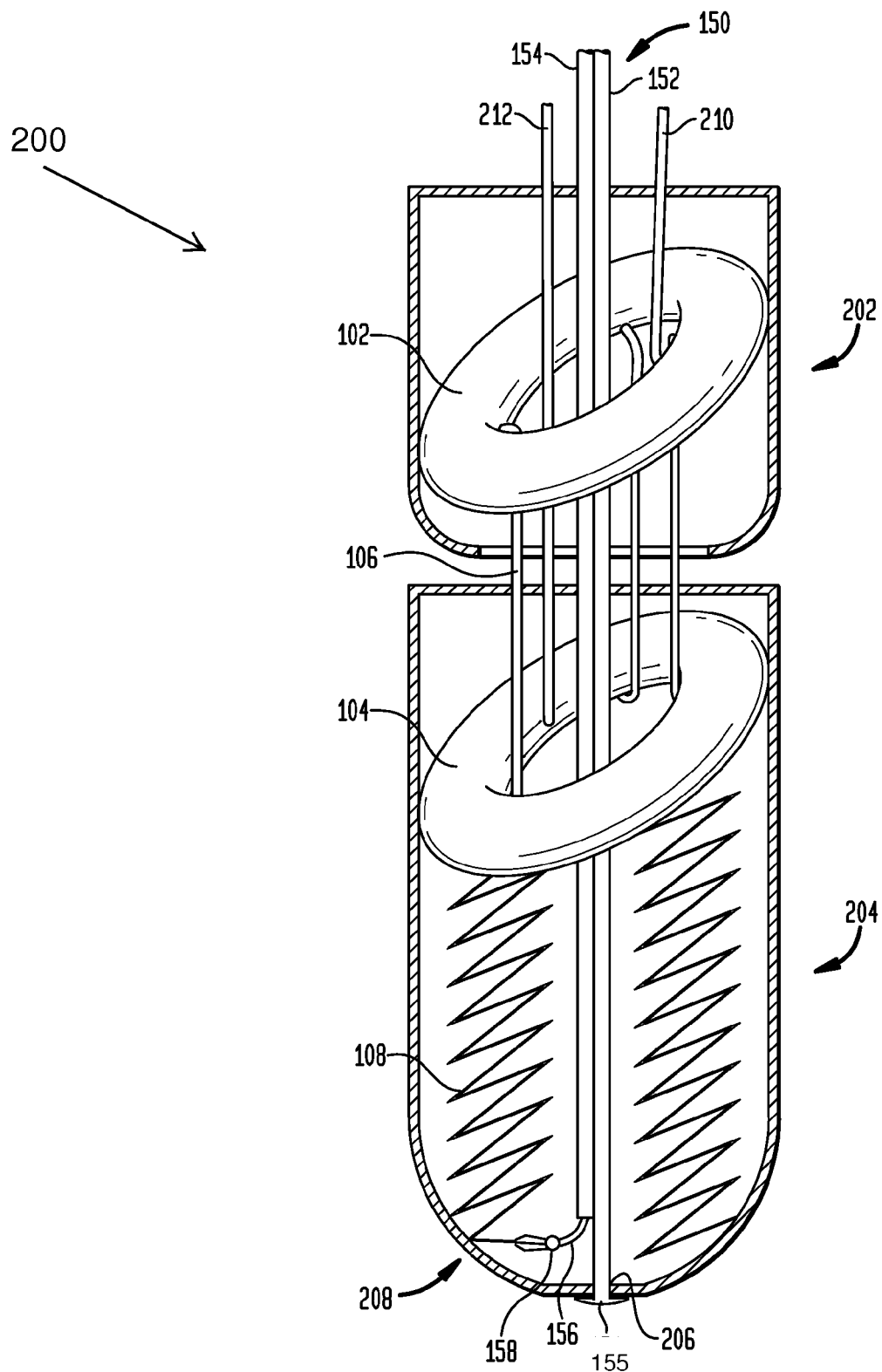

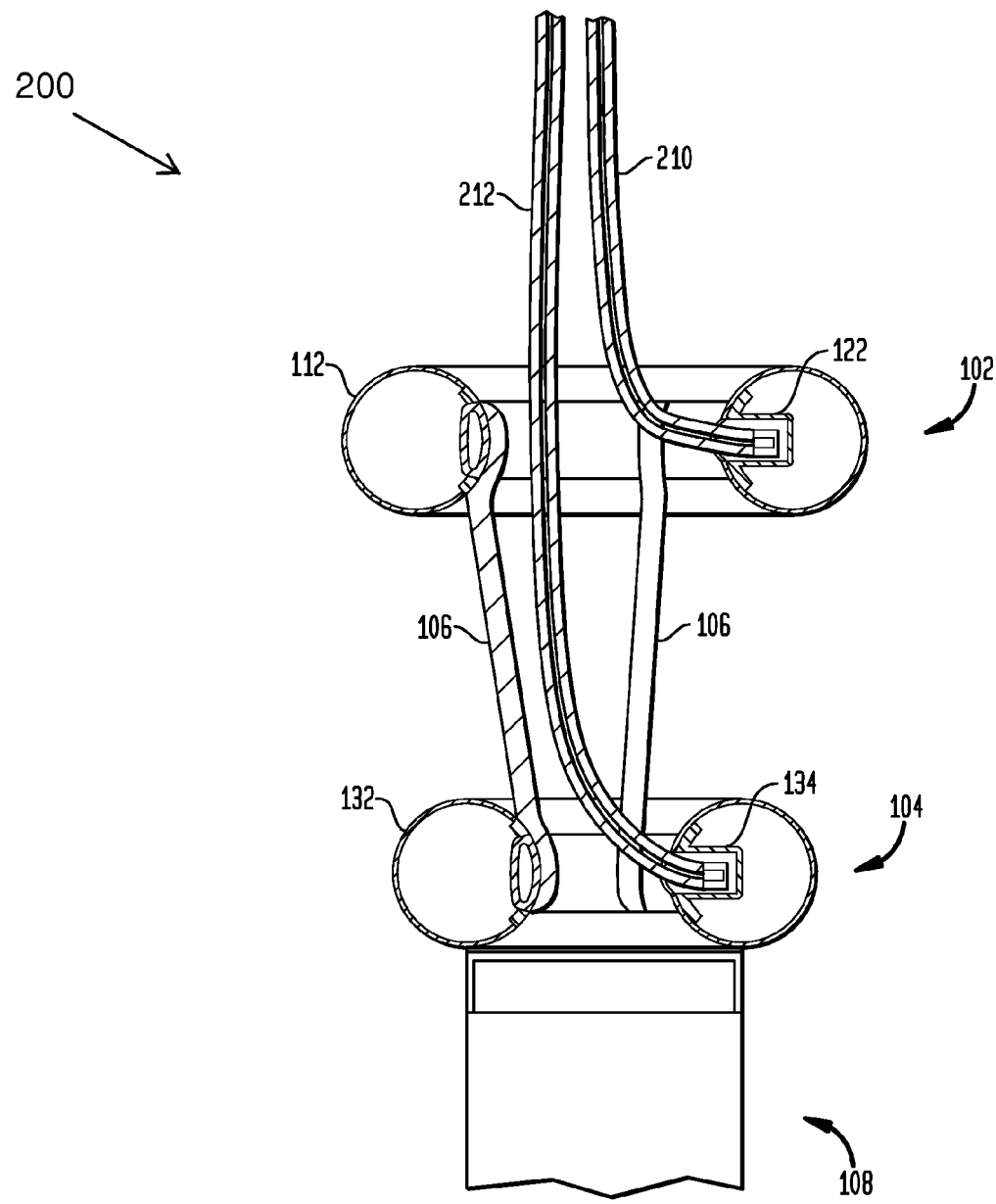

SYSTEMS AND METHODS FOR TREATING OBESITY AND TYPE 2 DIABETES

CROSS REFERENCE TO RELATED APPLICATIONS

This application is a continuation-in-part to U.S. patent application Ser. No. 12/566,193 filed Sep. 24, 2009, which claims the benefit of U.S. Provisional Patent Application Ser. No. 61/239,506 filed Sep. 3, 2009 and is also a continuation-in-part to U.S. patent application Ser. No. 12/508,701 filed Jul. 24, 2009, which claims the benefit of U.S. Provisional Patent Application Ser. No. 61/222,206 filed Jul. 1, 2009, the full disclosures of which are incorporated herein by reference for all purposes.

BACKGROUND OF THE INVENTION

The present invention relates to the field of obesity and diabetes and more specifically to minimally invasive systems and methods for controlling or treating obesity and/or type 2 diabetes.

Obesity is one of the leading preventable causes of death worldwide and has become a global epidemic affecting more than 400 million people. In the United States alone, approximately 300,000 obesity-linked deaths occur annually, and obesity-related co-morbidities lead to nearly $150 billion in healthcare spending. Obesity is a medical condition associated with many subsequent diseases, including type-II diabetes, cardiovascular disease, sleep apnea and certain types of cancer. These conditions often have severe adverse effects on overall health, reduce quality of life, limit productivity, lead to significant medical costs, and can ultimately lead to reduced life expectancy.

While obesity has a range of contributing causes, the vast majority of obese individuals are obese because they overeat, fail to exercise adequately, and in some cases have genetic predispositions to weight gain. The primary treatment for obesity is dieting, routine physical exercise, and in some cases pharmacologic therapy. Obesity surgery, including irreversible Roux-en-Y gastric bypass (RYGB) and Laparoscopic Adjustable Gastric Banding (LAGB), involves surgical restriction of the stomach. These interventions are typically directed at either (i) reducing the caloric intake of the patient by triggering the satiety impulse more rapidly or physically removing the ability of the individual to ingest more than a limited amount of food, or (ii) inhibiting the ability of the individual's digestive system to extract the full caloric value of the food being eaten.

The current surgical treatments for obesity, although often effective in achieving sustainable weight loss and thus reducing associated co-morbidities, involve gross anatomical reconstruction of the digestive system, which may be irreversible. Unfortunately, as has become widely publicized in the print and broadcast media, there can be significant adverse events, complications, and/or mortality associated with the most radical of these procedures (including but not limited to RYGB). In a large number of patients, subsequent surgical procedure(s) are required to address the complication(s) from the original surgery. While use of RYGB and LAGB are approved for individuals with lower BMIs (i.e., <40), the risks associated with the procedures have limited their adoption and/or use to only the morbidly obese population (>40 BMI). Recent reports indicate that there is a need to expand the options for obesity surgery in order to provide safer alternatives for individuals who are not prepared to risk the adverse consequences of radical RYGB and LAGB surgery, but for whom a surgical intervention is wholly appropriate. In fact, many individuals who could benefit from surgical intervention before their excess weight results in serious health problems forego surgery due to the significant complications and high rates of long-term adverse events leading to poor quality of life. Thus, there is a growing need for an effective and safe alternative to obesity surgery for the obese patient population worldwide.

Diabetes mellitus type 2 or type 2 diabetes is a disorder that is characterized by high blood glucose in the context of insulin resistance and relative insulin deficiency. There are an estimated 23.6 million people in the U.S. (7.8% of the population) with diabetes with 17.9 million being diagnosed, 90% of whom are type 2. With prevalence rates doubling between 1990 and 2005, CDC has characterized the increase as an epidemic. Traditionally considered a disease of adults, type 2 diabetes is increasingly diagnosed in children in parallel to rising obesity rates due to alterations in dietary patterns as well as in life styles during childhood.

Type 2 diabetes is a chronic, progressive disease that has no established cure, but does have well-established treatments which can delay or mitigate the inevitable consequences of the condition. Often, the disease is viewed as progressive since poor management of blood sugar leads to a myriad of steadily worsening complications. However, if blood sugar is properly maintained, then the disease is effectively cured—that is, patients are at no heightened risk for neuropathy, blindness, or any other high blood sugar complication. Type 2 is initially treated by adjustments in diet and exercise, and by weight loss, most especially in obese patients. The amount of weight loss which improves the clinical picture is sometimes modest (2-5 kg or 4.4-11 lb); this is almost certainly due to currently poorly understood aspects of fat tissue activity, for instance chemical signaling (especially in visceral fat tissue in and around abdominal organs).

Gastric bypass procedures typically entail surgical restriction of the size of the stomach and rerouting or bypassing a proximal portion the intestine to reduce absorption of nutrients. A study of 20-years of gastric bypass patients found that 80% of those with type 2 diabetes before surgery no longer required insulin or oral agents to maintain normal glucose levels. Weight loss also occurred rapidly in many people in the study who had had the surgery. Unfortunately, gastric bypass procedures involve irreversible reconstruction of gastrointestinal anatomy and may be associated with significant adverse events, and/or mortality. In spite of the growth in the number of surgical procedures for weight loss (greater than 250,000 annually in the US), only 1.2% of eligible patients elect to undergo these invasive surgeries each year.

Many patients who could benefit from these procedures forego surgery due to the significant complications and high rates of long-term adverse events leading to poor quality of life. The estimated 0.3-2% mortality rate along with the 19% surgical complication rate for RYGB have been major barriers for expanding the use of surgery in broader patient populations.

In view of the foregoing, there is a need in the art for new devices and methods for controlling and treating obesity and type 2 diabetes.

SUMMARY OF THE INVENTION

The present invention provides systems, apparatus and methods for treating wounds in patients, particularly chronic lower limb wounds in patients lacking the innate ability to regulate glucose (e.g., diabetic patients). In one aspect of the invention, a method for treating wounds includes positioning a flexible sleeve within the patient such that the sleeve extends through at least a portion of the duodenum to inhibit contact between chyme passing therethrough and at least a portion of an inner surface of the duodenum. The hollow sleeve is maintained within the duodenum for a sufficient period of time to reduce a blood glucose level in the patient. Preferably, the sleeve will be maintained in position for a sufficient period of time to permit the normalization of blood glucose levels in the patient (i.e., reducing such glucose levels to below about 150 mg, preferably below about 125 mg).

The sleeve creates an "internal bypass" that substantially inhibits contact between chyme and other substances entering the duodenum from the stomach of the patient and the bypassed portion of the duodenum. This reduces hormonal triggers that help to down-regulate the production of glucose, thereby resulting in the relief of certain symptoms that inhibit the body from effectively healing the wound, such as decreased peripheral vascular perfusion, neuropathy, a compromised or "inactive" immune system and a reduction in important components of healing, such as nitric oxide, vascular endothelial growth factors and the like.

In certain embodiments, the sleeve will be maintained in position for a sufficient period of time to increase the peripheral vascular perfusion in the patient. Patients lacking the innate ability to regulate glucose levels often suffer from decreased arterial perfusion of the extremities. The lack of blood flow to the extremities inhibits healing of wounds, such as foot ulcers and the like. In one embodiment of the present invention, the flexible sleeve is held in position within the duodenum until this process begins to reverse, thereby increasing peripheral vascular perfusion and allowing for accelerated healing of the wound.

In other embodiments, the sleeve will be maintained in position for a sufficient period of time to elevate an immune system response in the patient. Abnormally high glucose levels cause the body's immune system to become compromised or less active than normal. The white blood cells or leukocytes of the immune system that defend the body against infection become sluggish and unable to effectively fight infections, such as those associated with wounds. In this embodiment, the flexible sleeve is held in position within the duodenum until the activity of circulating leukocytes begins to substantially increase, which allows the patient's immune system to do its natural job of fighting the infection and accelerate healing of the wound.

In other embodiments, the flexible sleeve is maintained in position for a sufficient period of time to increase certain healing factors, such as nitric oxide and vascular endothelial growth factors (VEGF) in the patient. VEGF is an important signaling protein that stimulates the growth of new blood vessels, which can be a critical part of the angiogenesis process in wound healing. In one embodiment of the present invention, the flexible sleeve is held in position within the duodenum until a sufficient amount of VEGF are produced in the patient to accelerate healing of the wound.

In other embodiments, the flexible sleeve will be maintained in position for a sufficient period of time to halt or reverse neuropathy. Diabetic neuropathy is a common complication of patients lacking the innate ability to regulate glucose in which nerves are temporarily or permanently damaged as a result of high blood sugar levels (hyperglycemia). Neuropathy can complicate the wound healing process, particularly in the extremities. In this embodiment, the sleeve is held in position until nerves that have not been permanently damaged or destroyed can be repaired by the body to accelerate healing of the wound.

In a preferred embodiment, the flexible sleeve is sized and shaped to extend from the distal opening of the duodenal anchor through the duodenum and into a proximal portion of the jejunum of the patient. The sleeve is substantially hollow and positioned such that partially digested food, i.e. chyme, moving through the digestive tract passes through the interior of the sleeve. This inhibits the absorption of nutrients/calories in the upper segments of the small intestine and delays mixing of chyme with digestive enzymes such that a quantity of food ingested by the patient will have a smaller caloric value with the sleeve in place. In addition, it is believed that the sleeve inhibits certain hormonal triggers that would otherwise occur when food passes through the duodenum and proximal jejunum; hormonal triggers that cause the body to become insulin resistant and result in type 2 diabetes.

In certain embodiments, the sleeve is removably introduced through a natural orifice in the patient into the small intestines, preferably endoscopically through the patient's esophagus, stomach and pylorus. The sleeve can be maintained in position within the duodenum in a variety of ways known to those of skill in the art (e.g., sutures, hooks, barbs, atraumatic anchoring mechanisms and the like), typically for about 2 weeks to one year, preferably between about 1 month to 6 months and more preferably between about 6-12 weeks.

In a preferred embodiment, the sleeve is maintained in position with a pair of anchor elements flexibly coupled to each other and the sleeve. In the preferred embodiment, the flexible anchors are endoscopically introduced with the sleeve and positioned on either side of the pylorus. The duodenal anchor element is preferably expanded to a size that will inhibit proximal movement of the duodenal anchor through the pyloric sphincter to ensure that the sleeve remains in the patient's intestines. Likewise, the gastric anchor element is expanded to a size that will inhibit or prevent distal movement through the pyloric sphincter to ensure that the device does not pass further into the intestines and create a blockage. In a preferred embodiment, the anchor elements are expanded by delivering a fluid into each anchor element to inflate said anchors. In other embodiments, the anchor elements may be expanded mechanically or by other suitable means.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 9 is a perspective view of a dissolvable distal capsule of the delivery system according to the present invention;

FIG. 10A is a partial cross-sectional view of the bypass device and the delivery system according to the present invention;

FIG. 10B is a cross-sectional view of a portion of the bypass device with fluid tubes of the delivery system still coupled thereto;

DETAILED DESCRIPTION OF THE PREFERRED EMBODIMENTS

Figure 1:
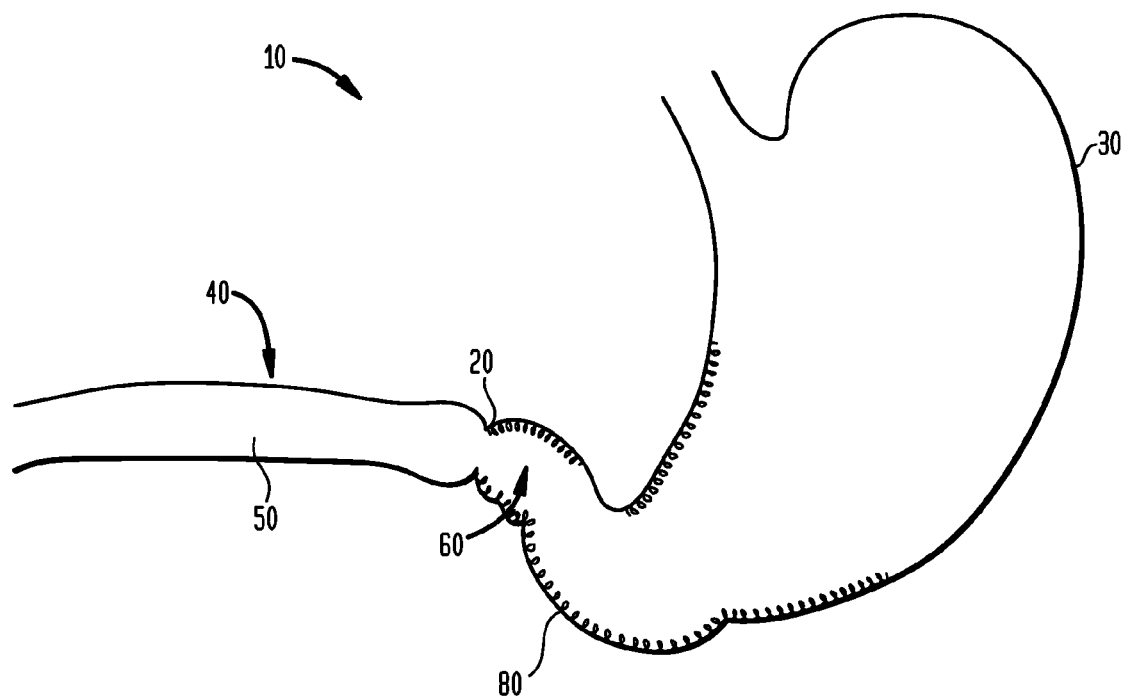
FIG. 1 is a view of a portion of a normal GI tract of a human.

In the present invention, systems, devices and methods are disclosed for treating and controlling obesity and/or type II diabetes. In particular, the systems and methods of the present invention provide an internal bypass of a proximal portion of the small intestines to inhibit contact between chyme and the bypassed small intestinal walls while allowing natural peristalsis to occur. The present invention is related to co-pending patent application Nos. 61/123,472 filed Apr. 9, 2008; 61/206,048 filed Jan. 27, 2009; Ser. No. 12/420,219 filed Apr. 8, 2009; Ser. No. 12/384,889 filed Apr. 9, 2009; Ser. No. 12/384,890 filed Apr. 9, 2009 and Ser. No. 12/384,898 filed Apr. 9, 2009, the full disclosures of which were previously incorporated herein by reference.

Diabetic foot ulcers are one of the major complications of diabetes mellitus. Foot ulcers occur in 15% of all patients with diabetes and precede 84% of all lower leg amputations. The significant increase in mortality among diabetic patients with foot ulcers observed over the past 20 years is considered to be due to the development of macro and micro vascular complications, including failure of the wound healing process.

Wound healing is a 'make-up' phenomenon for the portion of tissue that gets destroyed in any open or closed injury to the skin. Being a natural phenomenon, wound healing is usually taken care of by the body's innate mechanism of action that works reliably most of the time. The key feature of wound healing is the stepwise repair of lost extracellular matrix (ECM) that forms the largest component of the dermal skin layer. Therefore, controlled and accurate rebuilding becomes essential to avoid under or over healing that may lead to various abnormalities. But in some cases, certain disorders or physiological insults disturb the wound healing process that otherwise proceed smoothly in an orderly manner. Diabetes mellitus is one such metabolic disorder that impedes the normal steps of wound healing process. Many histopathological studies show a prolonged inflammatory phase in diabetic wounds, which causes a delay in the formation of mature granulation tissue and a parallel reduction in wound tensile strength.

High blood sugar levels prevent white blood cells, which are important in defending the body against bacteria and also in cleaning up dead tissue and cells, from functioning normally. When these cells do not function properly, wounds take much longer to heal and become infected more frequently. Also, long-standing diabetes is associated with thickening of blood vessels, which prevents good circulation including the delivery of enough oxygen and other nutrients to body tissues.

Another consequence of high blood sugar levels is that the body has difficulty producing many important components in the healing process, such as vascular endothelial growth factors (VEGF) and nitric oxide. For example, nitric oxide is known as an important stimulator of cell proliferation, maturation and differentiation. Thus, nitric oxide increases fibroblast proliferation and thereby collagen production in wound healing. Also, L-arginine and nitric oxide are required for proper cross linking of collagen fibers, via proline, to minimize scarring and maximize the tensile strength of healed tissue. Endothelial cell specific nitric oxide synthase (EcNOS) is activated by the pulsatile flow of blood through vessels. Nitric oxide produced by EcNOS, maintains the diameter of blood vessels and proper blood flow to tissues. In addition to this, nitric oxide also regulates angiogenesis, which plays a major role in wound healing.

Diabetic patients exhibit reduced ability to generate nitric oxide from L-arginine. Reasons that have been postulated in the literature include accumulation of nitric oxide synthase inhibitor due to high glucose associated kidney dysfunction and reduced production of nitric oxide synthase due to ketoacidosis observed in diabetic patients and pH dependent nature of nitric oxide synthase.

The present invention provides systems, apparatus and methods for treating wounds in patients, particularly chronic lower limb wounds in patients lacking the innate ability to regulate glucose (e.g., diabetic patients). In one aspect of the invention, a method for treating wounds includes positioning a flexible sleeve within the patient such that the sleeve extends through at least a portion of the duodenum to inhibit contact between chyme passing therethrough and at least a portion of an inner surface of the duodenum. The hollow sleeve is maintained within the duodenum for a sufficient period of time to reduce a blood glucose level in the patient. Preferably, the sleeve will be maintained in position for a sufficient period of time to permit the normalization of blood glucose levels in the patient (i.e., reducing such glucose levels to below about 150 mg, preferably below about 125 mg).

The sleeve creates an "internal bypass" that substantially inhibits contact between chyme and other substances entering the duodenum from the stomach of the patient and the bypassed portion of the duodenum. This reduces hormonal triggers that help to down-regulate the production of glucose, thereby resulting in the relief of certain symptoms that inhibit the body from effectively healing the wound, such as decreased peripheral vascular perfusion, neuropathy, a compromised or "inactive" immune system and a reduction in important components of healing, such as nitric oxide, vascular endothelial growth factors and the like.

In certain embodiments, the sleeve will be maintained in position for a sufficient period of time to increase the peripheral vascular perfusion in the patient. Patients lacking the innate ability to regulate glucose levels often suffer from decreased arterial perfusion of the extremities. The lack of blood flow to the extremities inhibits healing of wounds, such as foot ulcers and the like. In one embodiment of the present invention, the flexible sleeve is held in position within the duodenum until this process begins to reverse, thereby increasing peripheral vascular perfusion and allowing for accelerated healing of the wound.

In other embodiments, the sleeve will be maintained in position for a sufficient period of time to elevate an immune system response in the patient. Abnormally high glucose levels cause the body's immune system to become compromised or less active than normal. The white blood cells or leukocytes of the immune system that defend the body against infection become sluggish and unable to effectively fight infections, such as those associated with wounds. In this embodiment, the flexible sleeve is held in position within the duodenum until the activity of circulating leukocytes begins to substantially increase, which allows the patient's immune system to do its natural job of fighting the infection and accelerate healing of the wound.

In other embodiments, the flexible sleeve is maintained in position for a sufficient period of time to increase certain healing factors, such as nitric oxide and vascular endothelial growth factors (VEGF) in the patient. VEGF is an important signaling protein that stimulates the growth of new blood vessels, which can be a critical part of the angiogenesis process in wound healing. In one embodiment of the present invention, the flexible sleeve is held in position within the duodenum until a sufficient amount of VEGF are produced in the patient to accelerate healing of the wound.

In other embodiments, the flexible sleeve will be maintained in position for a sufficient period of time to halt or reverse neuropathy. Diabetic neuropathy is a common complication of patients lacking the innate ability to regulate glucose in which nerves are temporarily or permanently damaged as a result of high blood sugar levels (hyperglycemia). Neuropathy can complicate the wound healing process, particularly in the extremities. In this embodiment, the sleeve is held in position until nerves that have not been permanently damaged or destroyed can be repaired by the body to accelerate healing of the wound.

In a preferred embodiment, the flexible sleeve is sized and shaped to extend from the distal opening of the duodenal anchor through at least a portion of the duodenum (i.e., between about 4-12 inches). In some embodiments, the sleeve may extend throughout the duodenum and into a proximal portion of the jejunum of the patient (i.e., between about 12-30 inches, preferably about 12-16 inches). The sleeve is substantially hollow and positioned such that partially digested food, i.e. chyme, moving through the digestive tract passes through the interior of the sleeve. This inhibits the absorption of nutrients/calories in the upper segments of the small intestine and delays mixing of chyme with digestive enzymes such that a quantity of food ingested by the patient will have a smaller caloric value with the sleeve in place. In addition, it is believed that the sleeve inhibits certain hormonal triggers that would otherwise occur when food passes through the duodenum and proximal jejunum; hormonal triggers that cause the body to become insulin resistant and result in type 2 diabetes.

In certain embodiments, the sleeve is removably introduced through a natural orifice in the patient into the small intestines, preferably endoscopically through the patient's esophagus, stomach and pylorus. The sleeve can be maintained in position within the duodenum in a variety of ways known to those of skill in the art (e.g., sutures, hooks, barbs, atraumatic anchoring mechanisms and the like), typically for about 2 weeks to one year, preferably between about 1 month to 6 months and more preferably between about 6-12 weeks.

In a preferred embodiment, the sleeve is maintained in position with a pair of anchor elements flexibly coupled to each other and the sleeve. In the preferred embodiment, the flexible anchors are endoscopically introduced with the sleeve and positioned on either side of the pylorus. The duodenal anchor element is preferably expanded to a size that will inhibit proximal movement of the duodenal anchor through the pyloric sphincter to ensure that the sleeve remains in the patient's intestines. Likewise, the gastric anchor element is expanded to a size that will inhibit or prevent distal movement through the pyloric sphincter to ensure that the device does not pass further into the intestines and create a blockage. In a preferred embodiment, the anchor elements are expanded by delivering a fluid into each anchor element to inflate said anchors. In other embodiments, the anchor elements may be expanded mechanically or by other suitable means.

Referring to the drawings, wherein like reference numerals refer to like elements, there is shown in FIG. 1 an example of a portion of a GI tract 10 of a human body. Two smooth muscle valves, or sphincters, contain the contents of the stomach within the stomach upon ingestion. They are the esophageal sphincter (not shown), found in the cardiac region above the antrum cardiacum, and the pyloric sphincter 20, disposed between the stomach 30 and the small intestine 40. The pylorus 20 is the region of the stomach 30 that connects to the duodenum 50. The pylorus 20 is divided into two parts: the pyloric antrum 60 which connects the body to the stomach and the pyloric canal which connects to the duodenum 50. The pyloric sphincter 20 is a strong ring of smooth muscle at the end of the pyloric canal that functions to help regulate the passage of chyme from stomach 30 to the duodenum 50.

Satiety receptors 80 are generally located all along the inside lining of stomach tissue. Partially undigested food in GI tract 10 is generally referred to as chyme. If chyme remains in the region of the stomach before flowing into small intestine 40, satiety receptors 80 have a greater chance of being activated, which enhances the ability of an overweight or obese patient to feel satiated and suppresses the desire to eat.

Pyloric antrum 60 and duodenum 50 are innervated by the enteric nervous system and the parasympathetic nervous system (i.e., the vagus nerve). Many researchers have shown that the vagus nerve is responsible for the majority of afferent signals responsible for satiety. Thus, it is believed that increasing the afferent vagal nerve activity will result in satiety signals produced by the brain, making the patient feel more full and less inclined to eat.

A bypass device according to any of the below-described embodiments is preferably comprised of a polymeric structure that is compliant and generally flexible and bendable. Preferably, at least a portion of the device is made of silicone. Some portions of the device may be thicker than others for enhanced strength properties and to enhance the capability of the device to resist the natural peristaltic action of GI tract 10. Alternatively, some portions of the device may be thinner than others to allow for the material peristaltic actions of GI tract 10 to occur without the device providing a counteractive force. Preferably, if a portion of the device is bent or twisted during insertion, its polymeric structure will allow it to revert back to its resting or initial shape.

The one or more materials that comprise a bypass device according to the present invention are preferably selected for their ability to yield and flex during implantation and removal of the device. These properties also protect the patient and the tissues and organs with which the device comes into contact. The compliant nature of the bypass device allows its configuration to be manipulated during a surgical procedure, preferably in such a way that the device tends to revert to its operative configuration. The device may be made of shape memory material, such as nitinol or other known pliable polymeric materials, to allow for expansion back into its operative configuration. Any or all of the device may be coated with Teflon to provide a smooth outer surface to reduce friction between the device and the patient during implantation and removal.

The bypass device according to the present invention is structured to inhibit the rate that chyme passes through GI tract 10, thereby enhancing the ability of chyme to activate satiety receptors 80 and effectively enhance satiety in a patient. In particular, the device is preferably structured to reduce the rate of gastric emptying such that obesity can be controlled by controlling satiety.

The bypass device of the present invention is also designed to provide periodic or continuous contact pressure on the pyloric antrum and or the proximal portion of the duodenum. This contact pressure modulates (preferably stimulates) one or more nerves within these two structures, thereby increasing their activity. In certain embodiments, this contact pressure is brought about by the design of the device; namely, the flow restrictor and anchor are coupled to each other by flexible elements or columns (discussed in detail below). These flexible columns are sized such that the anchor generally rests against the proximal portion of the duodenum and the flow restrictor generally rests against the distal portion of the pyloric antrum. The flexible columns also have enough "give" or flexibility to allow the anchor and flow restrictor to move back and forth with the peristaltic motion of the GI tract. Thus, the anchor and flow restrictor may periodically move away from the proximal portion of the duodenum and the distal portion of the pyloric antrum, respectively. However, they will generally move back in contact with these structures to provide at least periodic pressure contact on these structures to stimulate the vagus nerves therein.

The bypass device is also designed to inhibit contact between chyme passing through the duodenum and the inner walls of the duodenum. This inhibits the absorption of nutrients/calories in the upper segments of the small intestine and delays mixing of chyme with digestive enzymes such that a quantity of food ingested by the patient will have a smaller caloric value with the sleeve in place. In addition, this reduces hormonal triggers that may help to down-regulate the production of glucose, thereby resulting in a nearly immediate relief of Type-II diabetes symptoms. The stabilization or elimination of Type-II diabetes symptoms will have a beneficial impact on patient health and further increase weight loss.

Incretins are gastrointestinal hormones, produced in response to the transit of nutrients that boost insulin production. Because an excess of insulin can determine hypoglycemia (extremely low levels of blood sugar)—a life-threatening condition, it has been speculated that the body has a counter-regulatory mechanism (or "anti-incretin" mechanism), activated by the same passage of nutrients through the upper intestine. The latter mechanism would act to decrease both the secretion and the action of insulin. Thus, in healthy patients, a correct balance between incretin and anti-incretin factors maintains normal excursions of sugar levels in the bloodstream. In some individuals, however, the duodenum and jejunum may be producing too much of this anti-incretin, thereby reducing insulin secretion and blocking the action of insulin, ultimately resulting in Type 2 diabetes.

Indeed, in Type 2 diabetes, cells are resistant to the action of insulin ("insulin resistance"), while the pancreas is unable to produce enough insulin to overcome the resistance. After gastrointestinal bypass procedures, the exclusion of the upper small intestine from the transit of nutrients may offset the abnormal production of anti-incretin, thereby resulting in remission of diabetes. However, it should be noted that the scientific community has not settled on a particular mechanism of action that causes patients undergoing such bypass procedures to become less "insulin resistant". Thus, the present invention is not limited to this particular mechanism of action or any particular mechanism of action.

Certain components of the bypass device according to the present invention may be discussed as being attached or connected to one another. Preferably, the device is constructed of one continuous piece and of one material, preferably silicone. However, two or more components of the device may be manufactured separately and subsequently assembled. If assembled, components may be glued together using a silicone-based glue.

Figure 2:
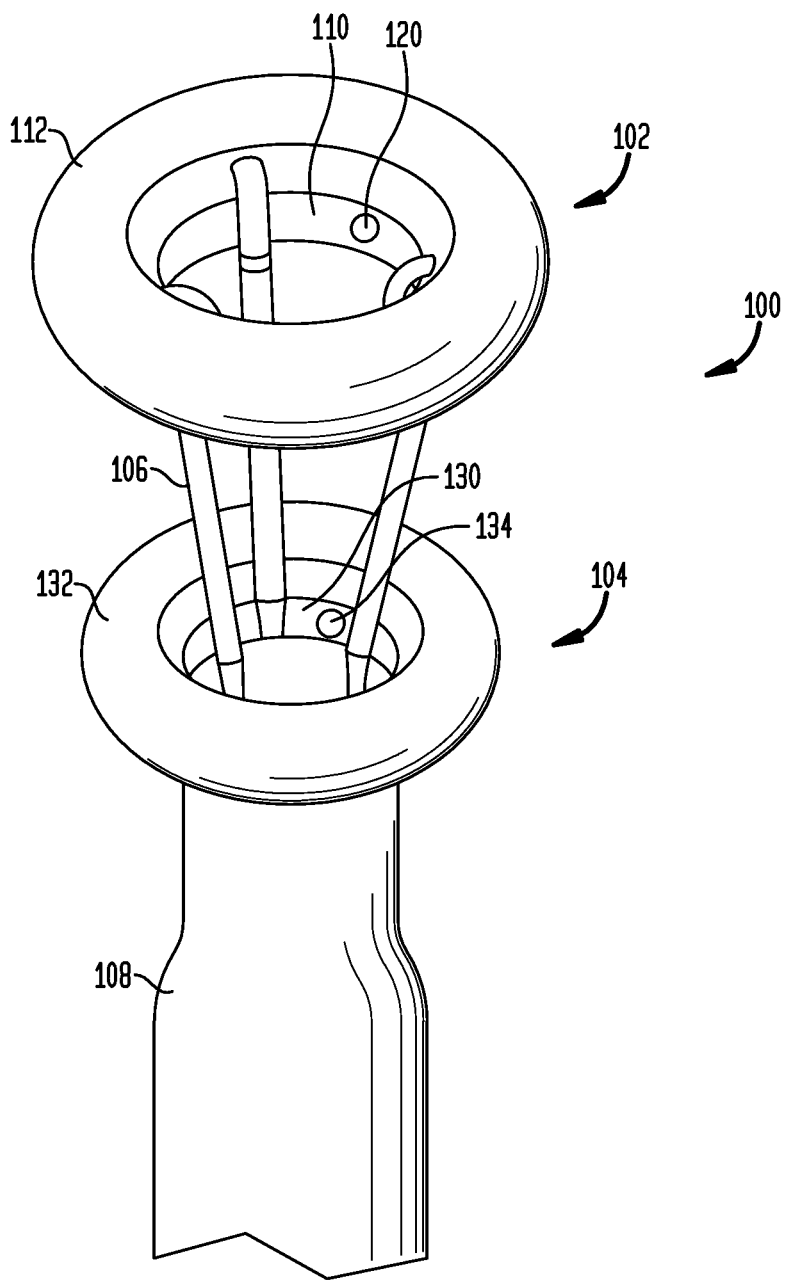
FIG. 2 is a perspective view of a bypass device in an operative configuration according to one embodiment of the present invention.

FIG. 2 illustrates one preferred embodiment of a bypass device 100 according to the present invention. As shown, device 100 includes a gastric anchor 102 coupled to a duodenal anchor 104 by a plurality of flexible silicone tethers or pyloric columns 106 and a hollow sleeve 108 coupled to the distal end of duodenal anchor 104. Pyloric columns 106 are designed to extend through the pyloric sphincter 20 to allow both gastric anchor 102 and duodenal anchor 104 to have some limited movement back and forth within the stomach 30 and duodenum 50, respectively, with the natural peristalsis motion of the GI tract (see FIG. 16). Pyloric columns 106 may be cylindrical or any other type of prismic shape and are preferably designed such that the distance between the distal end of gastric anchor 102 and the proximal end of duodenal anchor 104 is about 10-60 mm, preferably about 20-40 mm, and more preferably about 30 mm, in the fully extended, but relaxed condition (i.e., non-elastically extended). Preferably, device 100 includes at least two, preferably three, pyloric columns 106 each having a diameter of about 1-5 mm which are attached to the inside surfaces of anchors 102, 104. Alternatively, anchors 102, 104 may be coupled together with a hollow sleeve that extends through the pyloric sphincter 20. The sleeve would preferably be sufficiently flexible to allow sphincter 20 to open and substantially close without hindrance from the sleeve.

Figure 3:
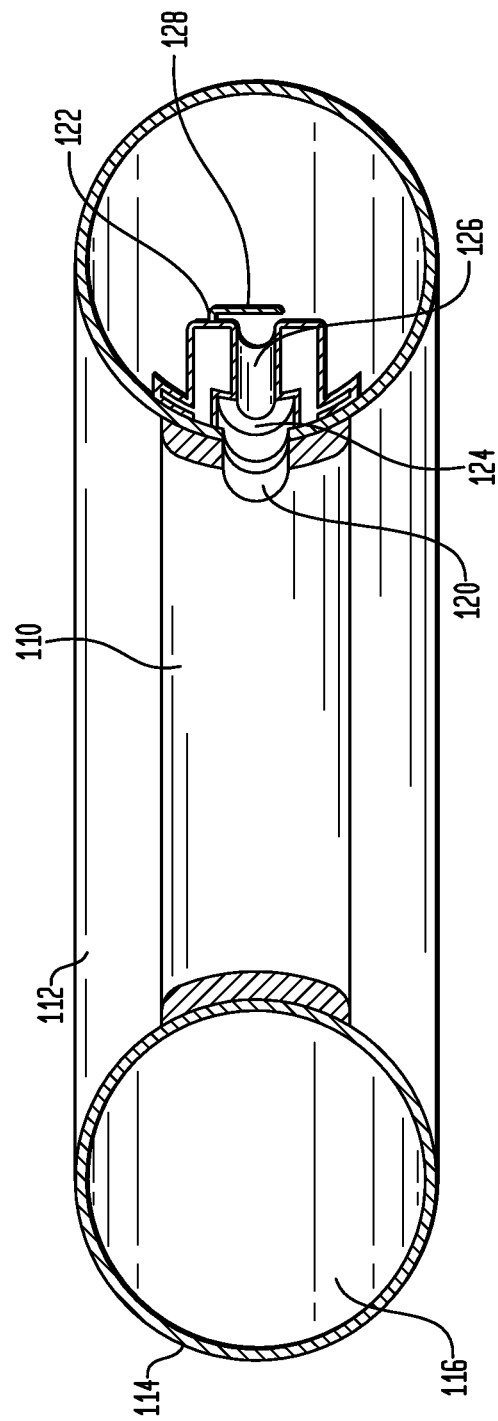
FIG. 3 is a cross-sectional view of a gastric anchor of the bypass device of FIG. 2.

FIG. 3 illustrates a cross-sectional perspective view of an exemplary embodiment of gastric anchor 102. As shown, gastric anchor 102 includes an internal ring 110 coupled to an annular inflatable membrane 112 having a substantially annular or toroidal shape. Inflatable membrane 112 comprises an outer wall 114 surrounding a hollow interior 116 configured for inflation via a suitable fluid. Ring 110 and membrane 112 preferably comprise a flexible biocompatible material, such as a phosphlipid resistant silicone material (e.g., a fluorosilicone copolymer). Alternatively, ring 110 may comprise a water-absorbent material, such as a hydrogel, that expands and hardens upon contact with fluid. Ring 110 provides structural support for anchor 102, while inflatable member 112 allows anchor 102 to move between a collapsed configuration for introduction through the patient's esophagus and an expanded configuration within the stomach. Thus, ring 110 is preferably harder and less flexible than inflatable membrane 112 having a durometer of at least about 70 A, preferably greater than about 80 A, while membrane 112 preferably has a durometer between about 30-60 A, more preferably between about 40-60 A.

In an alternative embodiment, anchor 102 may simply include an inflatable member 112 without support ring 112. In this embodiment, the inflatable member 112 would be inflated to a size and pressure sufficient to withstand peristalsis forces without compressing to a size that would allow the anchor 102 to pass through pyloric sphincter 20.

Gastric anchor 102 further includes a fluid inlet 120 for delivery of a fluid into hollow interior 116 of membrane 112. In the preferred embodiment, fluid inlet 120 comprises a valve 122 formed along the inner circumference of ring 110 and extending into interior 116 of membrane. As shown, valve 122 includes small chamber 124 in which a hole 126 is formed. Hole 126 extends radially from the inner surface of ring 110, through ring 110, into interior 116 of membrane 112. A flexible silicone flap 128, formed as part of the interior surface of the inflatable member 112, is located adjacent to hole 126. Silicone flap 128 serves to occlude hole 126 once the pressure within interior 116 of inflatable member 112 exceeds the pressure exterior to the member 112, thereby forming a one-way valve to prevent fluid egress from membrane 112.

In addition to, or as an alternative to, the one-way valve, a curable fluid, such as silicone, may be injected into the fluid pathway after the saline. The curable fluid will cure and harden, thereby preventing any fluid egress from the interior of inflatable member 112. In another embodiment, the inflatable members of the anchors may comprise a material that self-seals when punctured with a very sharp small instrument such as a syringe. In this embodiment, the inflatable members of the bypass device may simply be inflated with a syringe and then self-sealed by the material to prevent fluid egress.

In the preferred embodiment, ring 110 has an inner diameter of about 10-50 mm, preferably about 20-40 mm, and more preferably about 30 mm, and a thickness of about 1-5 mm, preferably about 3 mm. Inflatable membrane 112 has an outer diameter of about 30-70 mm, preferably about 40-50, and more preferably about 45 mm, when the pressure within membrane 112 is equal to the pressure outside (the state of nominal inflation, i.e., complete inflation without elastic deformation). In the preferred embodiment, however, membrane 112 is designed such that fluid can be injected into interior 116 until it has expanded significantly beyond the initiation of elastic deformation, with a maximum exterior diameter of the implanted gastric portion preferably being between about 50 and 60 mm.

Duodenal anchor 104 preferably has a similar structure as gastric anchor 102; including an inner ring 130 and an annular inflatable membrane 132 having a substantially annular or toroidal shape (see FIG. 2). Inflatable membrane 132 is designed to inflate into a substantially annular shape that provides for a secure anchor against the distal opening of the pyloric sphincter. This ensures that anchor 104 will remain in place within the duodenum 50 despite the natural peristalsis forces acting against anchor 104. Anchor 104 further includes a valve structure 134 (similar in design to gastric anchor 102) for delivering a fluid into an interior of membrane 132 to inflate membrane 132. In the exemplary embodiment, ring 130 has an inner diameter of between about 10-20 mm, preferably about 15 mm, a thickness of between about 1-5 mm, preferably about 3 mm. Inflatable membrane 132 preferably has an outer diameter of between about 20-30 mm, preferably about 25 mm, when the pressure within membrane 132 is equal to the pressure outside (the state of nominal inflation, i.e., complete inflation without elastic deformation). Similar to the gastric component, membrane 132 is designed for inflation beyond the initiation of elastic deformation, with a maximum exterior diameter of the implanted duodenal anchor being between about 30 and 50 mm, preferably between about 35 to 40 mm.

In an alternative embodiment, gastric and duodenal anchors 102, 104 include one or more expandable components that either completely or partially replace the fluid used in the previous embodiment to inflate or expand anchors 102, 104. In a preferred embodiment, the expandable components comprise fluid-absorbent materials designed to expand upon contact with certain fluid, such as hydrogels. Hydrogels are networks of polymer chains that are water-insoluble and hydrophilic. In this embodiment, a plurality of hydrogel components (not shown) are housed within the inflatable members of anchors 102, 104. The hydrogel components will be introduced into the patient in the "dry" or smaller state within anchors 102, 104. A fluid, such as saline, is delivered into the interior of the inflatable members and is absorbed within the hydrogel components (which may be of any shape, such as spheres or the like) to expand these components, thereby expanding the inflatable members.

In one aspect of this embodiment, the anchors 102, 104 include a plurality of hydrogel beads, preferably about 0.5 to 3.0 mm in diameter, designed to expand to a larger size (e.g., about 4-6 mm in diameter) upon hydration with a fluid, such as saline. In this embodiment, anchors 102, 104 may or may not include inner rings 110 and they may not require one-way valves. The hydrogel balls provide additional rigidity to the anchors 102, 104. In addition, they provide additional safety in the event that the inflatable members are punctured with a small hole as the balls will remain within inflatable members in such event (as opposed to a puncture that will allow all of the fluid to exit inflatable members in the previous embodiments). Upon removal of the device, the inflatable members will be punctured with a large enough hole to allow the hydrogel balls to exit the interiors of the inflatable members. The hydrogel balls can be allowed to pass through the patient's GI tract and excreted naturally.

Figure 4:
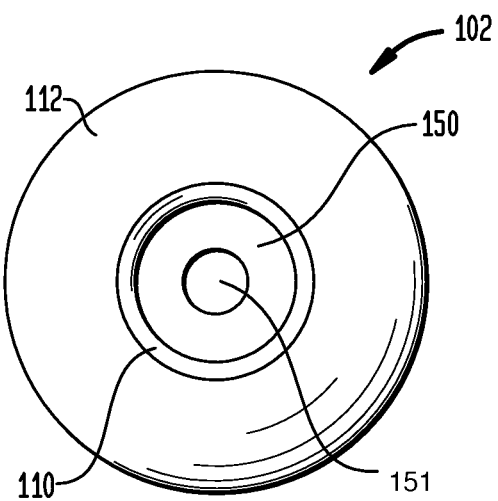
FIG. 4 is a top view of an alternative embodiment of a gastric anchor according to the present invention.

FIG. 4 illustrates an alternative embodiment of gastric anchor 102. In this embodiment, anchor 102 is substantially similar in design and construction as the anchor shown in FIG. 2, comprising a central support ring 110 surrounded by an inflatable member 112 having an internal valve 120. However, this anchor 102 also includes an internal restrictor plate 150 attached to support ring 110. Plate 150 has a central hole 151 designed to allow chyme to pass therethrough. Plate 150 serves to substantially inhibit the flow of chyme from the stomach to the pyloric sphincter. It is believed that this will cause the prolongation of satiety, and result in fewer meals being eaten and/or smaller meals being ingested. The inner diameter of hole 151 will vary depending on the rate of chyme flow desired for the individual patient. For example, hole 151 may have a diameter of about 5-20 mm.

Figure 5:
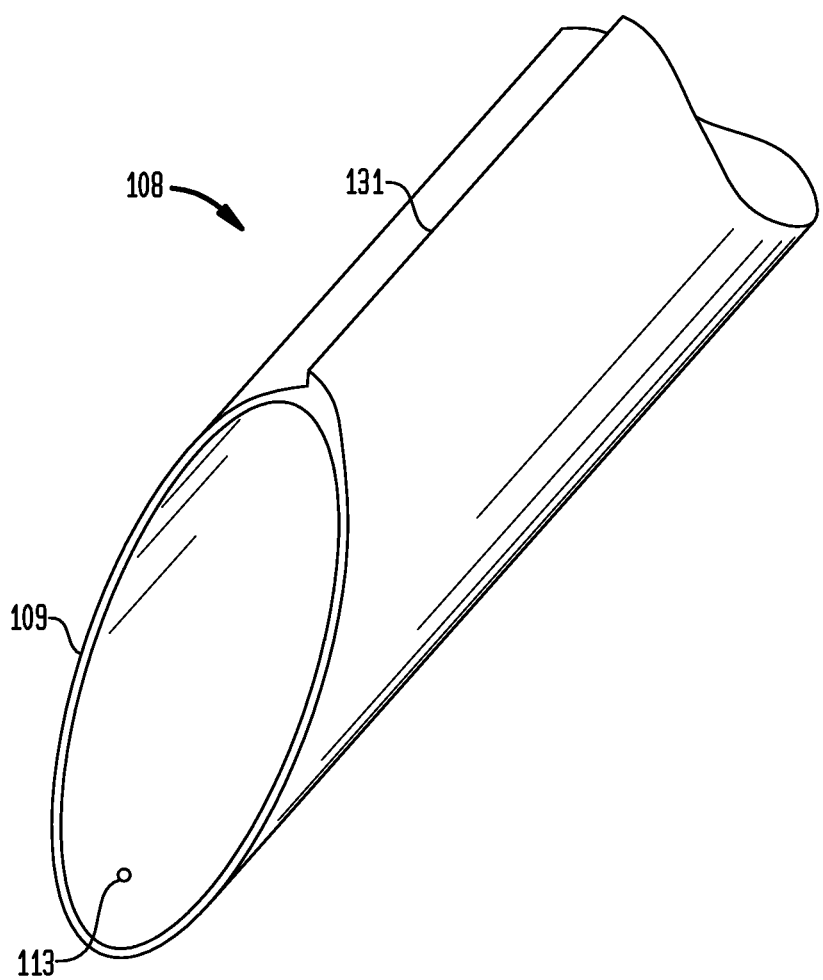
FIG. 5 illustrates a distal end of a hollow sleeve according to the present invention.

Referring to FIG. 5, sleeve 108 may be manufactured to any length according to a particular patient and/or surgical procedure, and in the preferred embodiment includes at its distal end a beveled tip 109. Along its length, sleeve 108 may have one or more side holes 113 which provide further access for chyme to enter sleeve 108. In some embodiments, a rib 131 is disposed along sleeve 108 and is preferably substantially parallel to the longitudinal axis of sleeve 108, though rib 131 may extend only partially along sleeve 108 and may take on a curved or other type of orientation with respect to the longitudinal axis. Rib 131 may be comprised of silicone and additionally may include a radiopaque material, such as barium, so that rib 131 may be detected by a fluoroscope. Rib 131 may be provided as a separate component and later attached to sleeve 108, or rib 131 may essentially be the overlapping seam formed during the manufacture of sleeve 108 when a flat piece of material is rolled into a tubular shape. In such a configuration, sleeve 108 may be comprised of a homogenous material attached by a radiopaque glue. Of course, as rib 131 is primarily used as an aid during implantation and/or removal of obesity device 100, rib 131 need not necessarily be included in this or any other embodiment according to the present invention.

Sleeve 108 preferably has a diameter that will substantially correspond with the inner diameter of the patient's duodenum and a length that will allow the sleeve to extend into at least the proximal portion of the jejunum depending on the individual patient's anatomy. Thus, sleeve 108 will typically have a length of between about 20-80 cm, preferably between about 55-75 cm, a thickness of about 0.05 mm to 0.22 mm and a diameter of between about 1 to 3 cm, preferably about 2.5 cm. Preferably, the proximal portion of sleeve 108 has an inner diameter of about 1.2 cm that expands laterally in the proximal direction to 1.5 cm so that it may be sealed to the lower surface of anchor 104. The material of the sleeve is preferably silicone, such as a polyethylene-reinforced silicone.

Sleeve 108 may include one or more markers (e.g., barium) designed for viewing the position of the sleeve within the intestines through fluoroscopy, such as rib 131 or other markers that are spaced along the length of sleeve 108. In addition, sleeve 108 may further include components that inhibit twisting or kinking of the sleeve 108. In one embodiment, these components include one or more stiffening elements, such as rings, coupled to either the inside or the outside of the sleeve at spaced locations along its length. These rings can, for example, be made of a slightly thicker silicone material that would resist twisting or kinking of the sleeve around the ring. In other embodiments, the stiffening elements may be in spiral shape or extending lengthwise along at least a portion of the sleeve 108.

Sleeve 108 may also include one or more internal lumens extending along a portion of or the entire length of the sleeve. The fluid lumens comprise a proximal end configured for coupled to a fluid delivery system to allow a fluid to flow through sleeve to extend sleeve through the patient's duodenum and/or to ensure that sleeve remains patent without any twists or kinks along its length. In one embodiment, the sleeve comprises multiple (e.g., 2-5) internal lumens extending from the proximal to the distal end of the sleeve and spaced from each other around the circumference of the sleeve. In another embodiment, the sleeve comprises an internal lumen that extends in a spiral pattern down the length of the sleeve.

In yet another alternative embodiment, sleeve 108 may further include one or more fluid chamber(s) coupled to one or more of the internal lumens. The fluid chamber(s) facilitate implantation of the sleeve within the patient by allowing the physician to at least partially fill one or more of the chambers before withdrawing the scope from the duodenum (discussed in more detail below). In addition, the fluid chambers provide stiffness to the sleeve to provide more stability to the sleeve and ensure that it remains in place within the patient after implantation. The fluid may also include a material that is observable under fluoroscopy (e.g., barium or the like) such that the location of the internal lumens and/or the fluid chambers can be viewed by a physician after implantation.

In one embodiment, the fluid chamber comprises an annular passage extending around the circumference of the sleeve at or near its distal end. This configuration provides the additional advantage that, when filled, the annular fluid chamber provides a distal anchor for the sleeve and the entire bypass device to provide additional against proximal migration of the sleeve and/or device. In another embodiment, the sleeve comprises multiple annular fluid chambers spaced along the length of the sleeve to provide additional rigidity to the sleeve, thereby ensuring that the sleeve remains patent and preventing any kinking or twisting along its length.

In an alternative implantation method, the sleeve 108 may be initially folded "accordion-style" and tucked into the interior of the anchor 104. The distal end of sleeve 108 is initially closed, with a small silicone rubber knob (not shown) attached to the bottom of sleeve 108 (e.g., like a "sock" with a ball on the inside surface of the "toe"). Just proximal to the ball, at a region where the diameter of sleeve 108 is about 2.1 cm, is a circumferential perforation (not shown) such that the ball and the "toe portion" of the sleeve will tear away from sleeve 108 leaving an open tubular sleeve behind.

Figure 6:
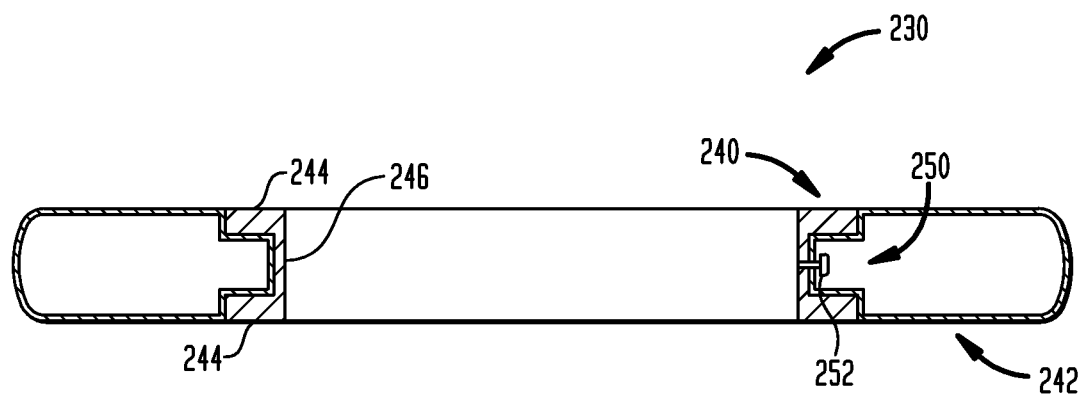
FIG. 6 is a cross-sectional view of an alternative embodiment of a duodenal anchor according to the present invention.
Figure 7:
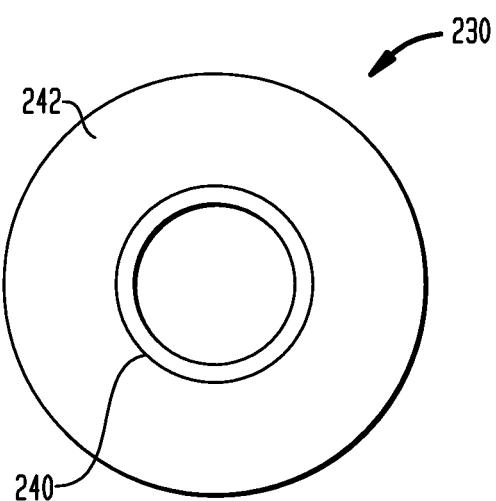
FIG. 7 is a top view of the duodenal anchor of FIG. 6.

Referring now to FIGS. 6 and 7, an alternative embodiment of a duodenal anchor 230 will now be described. As shown, anchor 230 comprises an annular support ring 240 coupled to an inflatable flexible membrane 242. In this embodiment, support ring 240 comprises two flat ring elements 244 connected together by a semi-rigid central ring 246 that holds the flat ring elements 244 apart from each other. Flat ring elements 244 and central ring 246 preferably comprise a suitable material, such as silicone, which may be molded as one-piece or molded separated and glued together with a suitable silicone glue. Flat ring elements 244 are preferably separated from one another by a distance of about 8-12 mm. Flexible membrane 242 is sealed to the exterior circumferential surfaces of flat ring elements 244 and central ring 246. Membrane 242 is initially tucked in a space 250 between flat ring elements 244 with sufficient additional material such that when saline is injected into the interior of membrane 242, an inflated "inner tube" structure is created. This inner tube structure is intended to inflate to a maximum diameter of between 30-45 mm (depending on the specific duodenal anatomy of a given patient).

A one-way valve 252 is disposed between ring elements 244 at one location around the circumference thereof and directed inwardly. This valve 252 is initially coupled to a thin tube (not shown) that extends up along the exterior of the gastric anchor through which membrane 242 can be inflated. In an exemplary embodiment, a small wire (not shown) is incorporated into the seal of the inner membrane 242 to the rings to permit simple and rapid deflation of membrane 242 for removal of the device. A small ball (not shown) may also be coupled to the wire and located external to ring elements 244 and membrane 242 for grasping by an endoscopic instrument. Pulling the ball causes the wire to tear through membrane 242 and the seal, thus rupturing membrane 242 and collapsing anchor 230.

Figure 8:
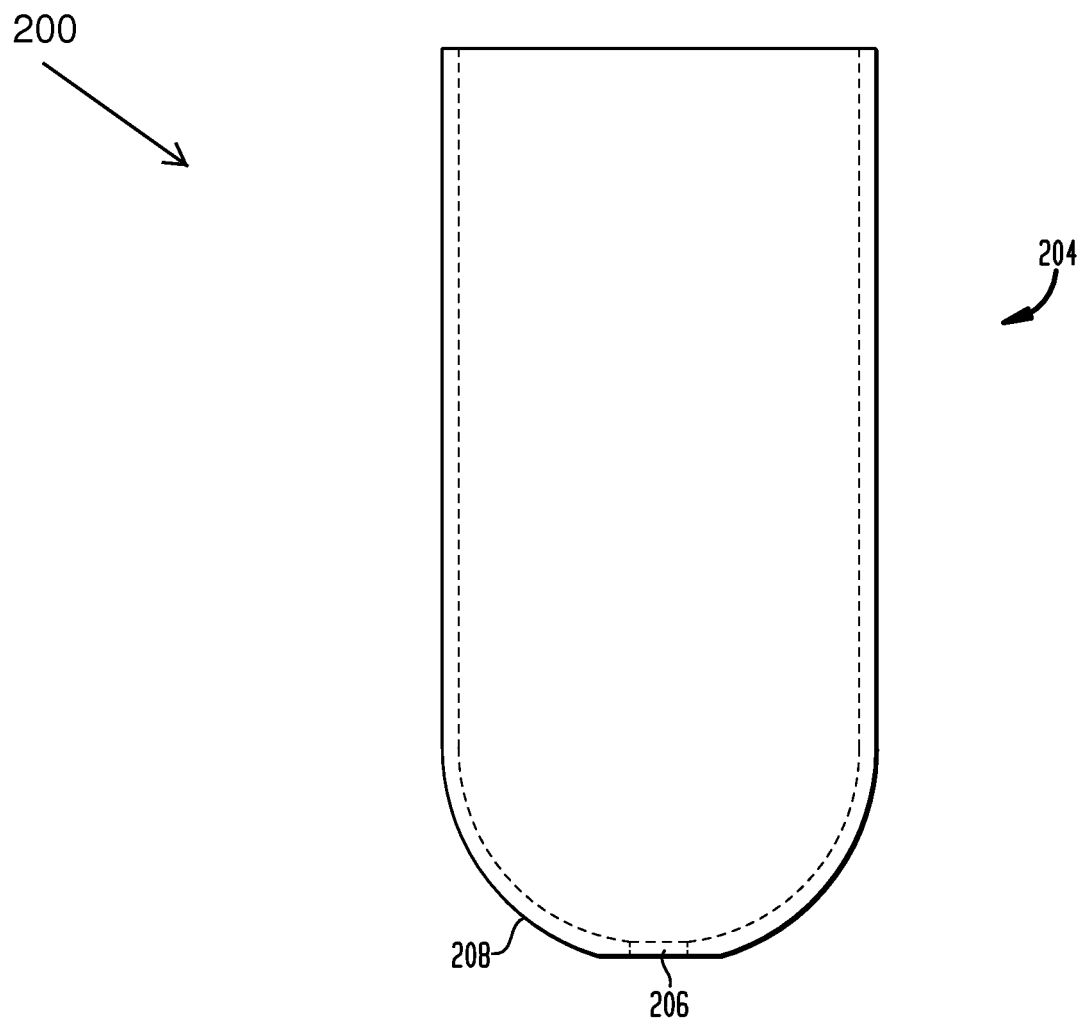
FIG. 8 is a perspective view of a dissolvable proximal capsule of a delivery system according to the present invention.

Referring now to FIGS. 8-10B, bypass device 100 further comprises a deployment system 200 for facilitating the deployment of device 100. As shown in FIGS. 8 and 9, deployment system 200 includes a proximal housing or capsule 202 and a distal housing or capsule 204. Capsules 202, 204 both comprise a biocompatible dissolvable material, such as gelatin and the like, designed to dissolve within the patient's body. As shown in FIG. 8, distal capsule 204 is sized and shaped to house sleeve 108 in a folded, compressed or collapsed configuration and duodenal anchor 104 in its collapsed or deflated configuration (see FIG. 10A). Distal capsule 204 is open at its proximal end, and has a bullet-shaped distal tip 208 with a small hole 206. Distal tip 208 is designed to facilitate passage of the capsule 202 (and sleeve 108 and anchor 104 therein) through the pylorus and into the duodenum. Hole 206 is sized and shaped for passage of a guidewire therethrough (see FIGS. 11-15). Capsule 202 is preferably about 80-160 mm long (preferably about 100-140 mm long) about 10-30 mm wide (preferably about 20 mm) and is preferably constructed to survive for less than 30 minutes before dissolving in the human intestines.

As shown in FIG. 9, proximal capsule 202 is sized and shaped to house gastric anchor 102 in its collapsed configuration and at least a portion of columns 106 therein (see FIG. 10A). Proximal capsule 202 is substantially cylindrically shaped and is primarily designed to facilitate passage of these components through the esophagus to minimize any damage to the inner walls of the esophagus. To that end, capsule 204 has a slightly curved distal end 205 with an opening 207 that is larger than distal opening 206 of distal capsule 204 to accommodate the various components of bypass device 100 therethrough, such as flexible columns 106; delivery structure 150 and fluid tube 210 (see FIG. 10B). In the preferred embodiment, capsule 202 is about 30-70 mm long (preferably about 50 mm) and about 10-30 mm wide (preferably about 20 mm). Capsule 202 preferably comprises a material that will dissolve in less than 15 minutes within the human stomach, such as gelatin and the like. Alternatively, capsules 202, 204 may comprise a resorbable material or a material that can be safely excreted by the patient.

Referring now to FIGS. 10A and 10B, deployment system 200 further includes fluid tubes 210, 212 coupled to valves 122, 134 of gastric and duodenal anchors, respectively. Tubes 210, 212 each include small one-way valves (not shown), such as an umbrella valve or a duckbill valve, formed in their distal tips. Tubes 210, 212 are preferably coupled to valves 122, 134 such that their own own-way valves are formed within the small chambers 124 of valves 122, 134. Upon inflation of the respective components, the tubes 210, 212 are then cut proximal to valves 122, 134 such that their one-way valves provide additional protection to ensure that fluid injected into the inflatable membranes 112, 132 cannot escape through the holes.

Deployment system 200 further comprises a central tube structure 150 designed to extend through bypass device 100 (i.e., through the center of gastric and duodenal anchors 102, 104 and sleeve 108). Central tube structure 150 has a support tube 152 with an inner lumen (not shown) sized for passage of a guidewire therethrough (discussed in detail below). Support tube 152 has an inner diameter of at least 2.8 mm and preferably about 3 mm. Support tube 152 extends through hole 206 in distal capsule 204 and preferably has widened distal tip 155 designed to engage the outer surface of distal tip 208 of capsule 204. This facilitates passing of guidewire into the distal opening of support tube 152. Alternatively, support tube 152 may comprise an enlarged distal end (not shown) having a larger diameter than hole 206 that is located within capsule 204. In this embodiment, the enlarged distal end of support tube 152 operates to push against capsule to propel capsule 204 forward as it advances through the patient's GI tract. Support tube 152 preferably comprises a material that has sufficient flexibility to easily navigate the patient's small intestines, yet sufficient rigidity to allow for a pushing force from outside of the patient's body to advance tube 152 and the rest of bypass device 100 through the patient's GI tract (discussed below). Suitable materials for support tube 152 are polypropylene and the like.

Central tube structure 150 further comprises a flexible tube 154 extending alongside support tube 150. Flexible tube 154 houses a wire 156 coupled to a snare or a clamp 158 at its distal end. An actuator, such as a handle 160 (see FIG. 12), is coupled to the proximal end of wire 156 for opening and closing clamp 158. As discussed below, flexible tube 154 and clamp 158 are designed to facilitate advancement of sleeve 108 through the patient's small intestines to its final deployment position. Note that flexible tube 154 and support tube 152 may alternatively comprise a single tubular structure with two separate lumens (one for wire 156 and one to accommodate the guidewire).

In one embodiment, sleeve 108 comprises one or more small extensions or polyps (not shown) extending from its distal tip. In this embodiment, tube 154 includes a distal tip (not shown) with a clamp or fastener designed to fasten to the polyps to facilitate advancement of sleeve 108 as discussed above. When the sleeve is in its final deployment position, an actuator on handle on the proximal end of the tube 154 allows the use to pull the clamp proximally relative to the distal tip to sever the polyps and thereby detach tube 154 from the sleeve 108. At this point, central tube structure 150 can be removed from the patient. The polyps will then pass through the patient's GI tract in a normal manner.

In an alternative embodiment, deployment system 200 includes a thin, hollow sheath coupled to a silicone ball (not shown). The ball is detachably coupled to the distal end of sleeve 108 and the sheath extends through sleeve 108 and duodenal and gastric anchors 102, 104. The ball has an axial hole formed therethrough aligned with the axial bore of the sheath. The axial bore of the flexible sheath has a length of about 120 mm, and an outer diameter of about 5 mm. The sheath and ball together allow the user to advance sleeve 108 through the intestines to its final deployment position.

In reference to FIGS. 11-16, a method of implanting and removing a bypass device 100 according to the present invention will now be described. While the description of this method will be specifically directed to the embodiments illustrated in FIGS. 2 and 3, it will be understood by those skilled in the art that this method (or similar methods) can be used to implant and remove all of the embodiments of the present invention, including embodiments or designs that may not be specifically described or illustrated herein.

Figure 11:
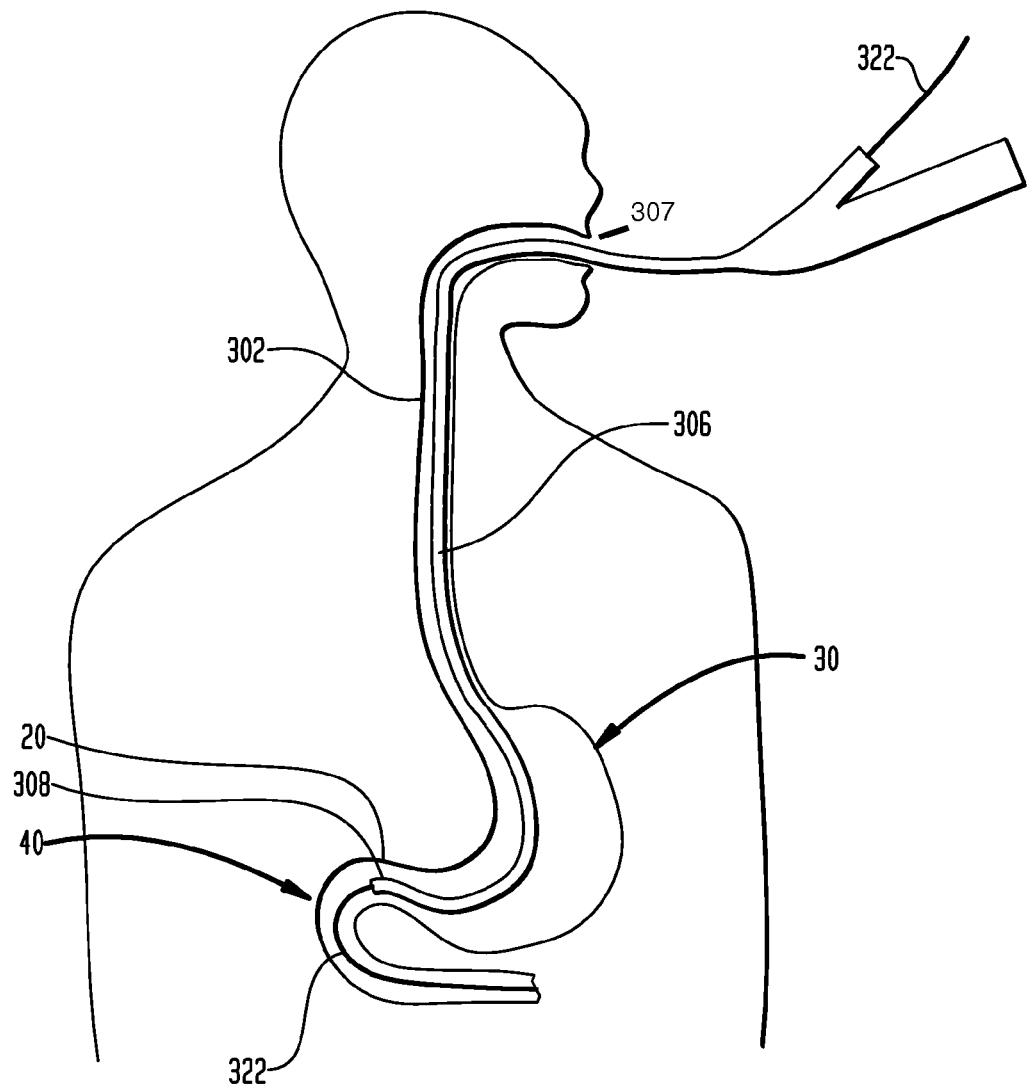
FIG. 11 illustrates the insertion of a gastroscope and guidewire through an esophagus of a patient.
Figure 15:
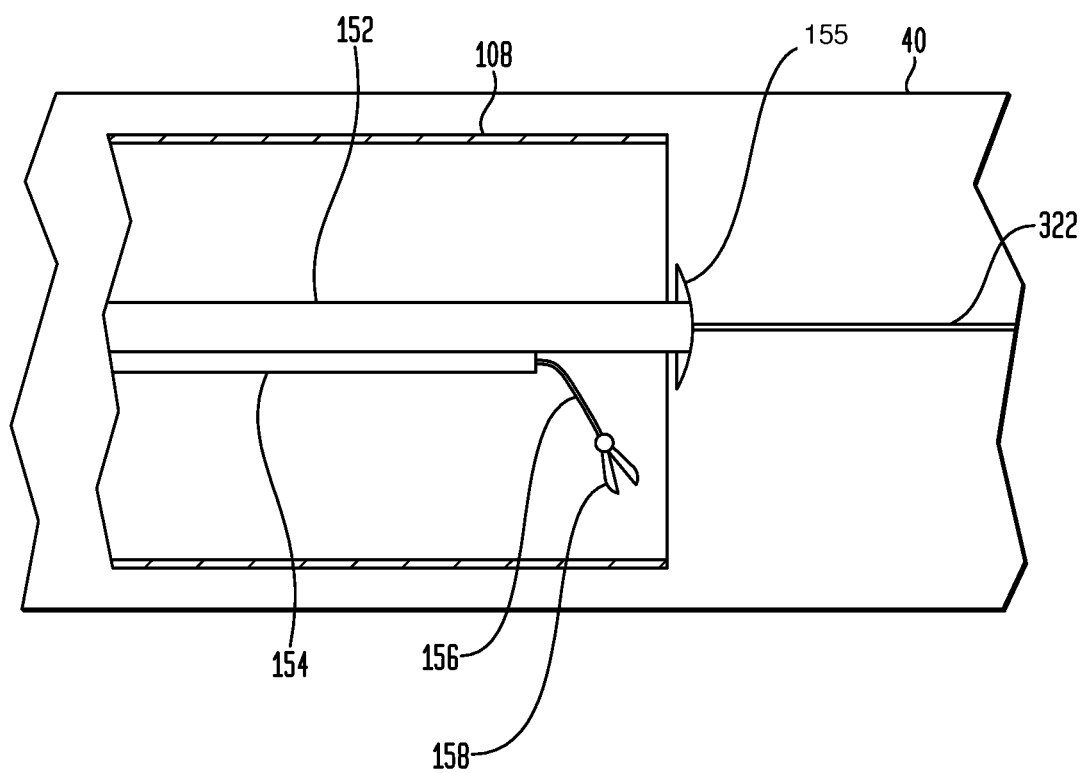
FIG. 15 illustrates the deployment of the sleeve into the small intestines of the patient.

Device 100 enters and exits the patient through esophagus 302 and is ultimately positioned in its operative state, wherein pyloric columns 106 extend through pyloric sphincter 20 (e.g., see FIG. 15). Initially, a gastroscope 306 is lubricated, inserted into patient's mouth 307, and fed through esophagus 302 and the gastroesophageal ("GE") junction into stomach 30, as shown in FIG. 11. Gastroscope 306 is preferably approximately 9.8 millimeters in length, and preferably has approximately a 2.8 millimeter working channel and suitable viewing and recording equipment, for example. It will be understood that tools and components that are described as being passed through or inserted into gastroscope 306 are passed through or inserted into its working channel. A lubricant such as Surgilube or equivalent may be provided as needed to lubricate the bypass device and/or any of the associated surgical equipment.

Gastroscope 306 should ultimately be positioned such that its distal end 308 is adjacent to pyloric sphincter 20. Preferably, a guidewire 322 is hydrated and inserted through gastroscope 306. Guidewire 322 is passed through pyloric sphincter 20, which may be aided by manipulation of gastroscope 306. It may also be beneficial to pass a distal end 308 of gastroscope 306 through pyloric sphincter 20 in order to maneuver guidewire 322 through same. There should preferably be at least about 30-40 centimeters of the length of guidewire 322 passed distally through pyloric sphincter 20 and into small intestine 40 so that any further movement of guidewire 322 during the insertion procedure does not result in the accidental removal of the distal end of guidewire 322 to a position proximal of pyloric sphincter 20. Of course, the length of guidewire 322 that should preferably be passed distally through pyloric sphincter 20 may vary according to different patients and/or procedures and may be less or more than 30-40 centimeters. After guidewire 322 is appropriately positioned, gastroscope 306 is removed from the patient.

Figure 12:
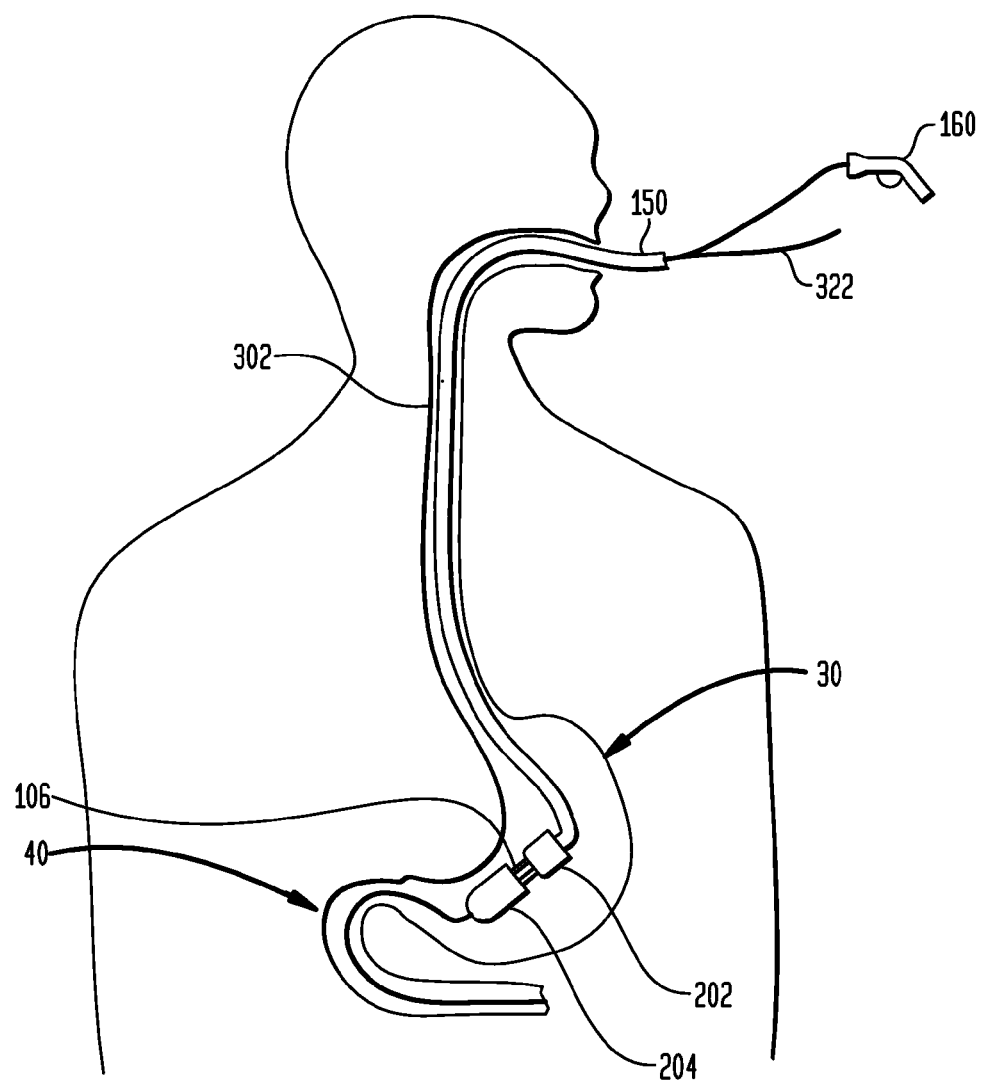
FIG. 12 illustrates the bypass device and a portion of the delivery system inserted into the stomach in the esophagus of the patient.
Figure 13:
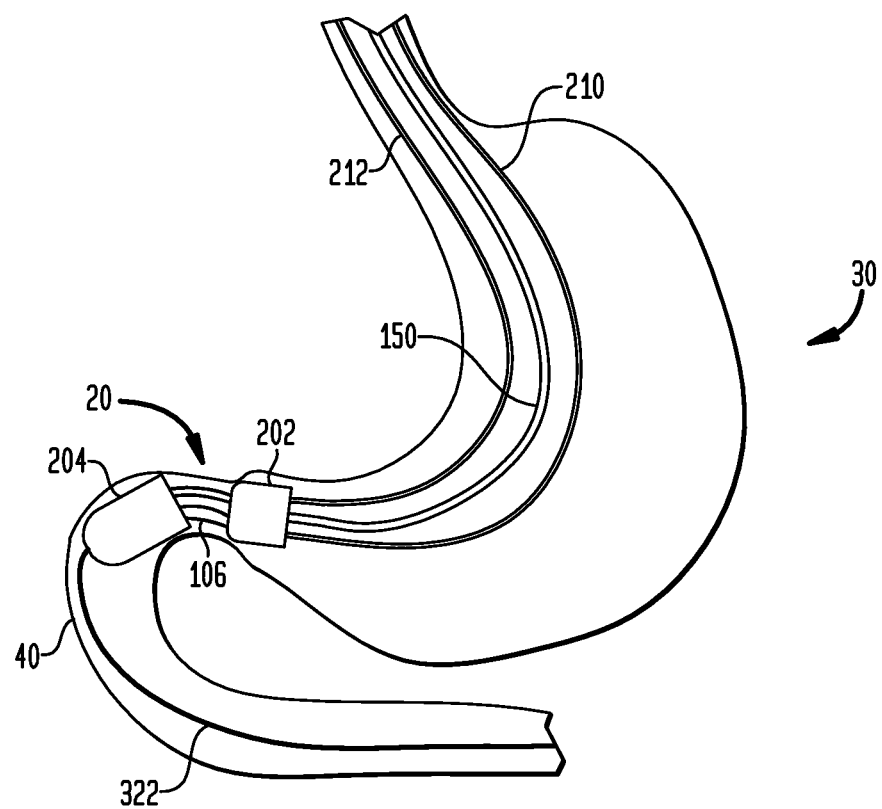
FIG. 13 illustrates the deployment of the duodenal anchor and the sleeve into the duodenum of the patient.
Figure 14:
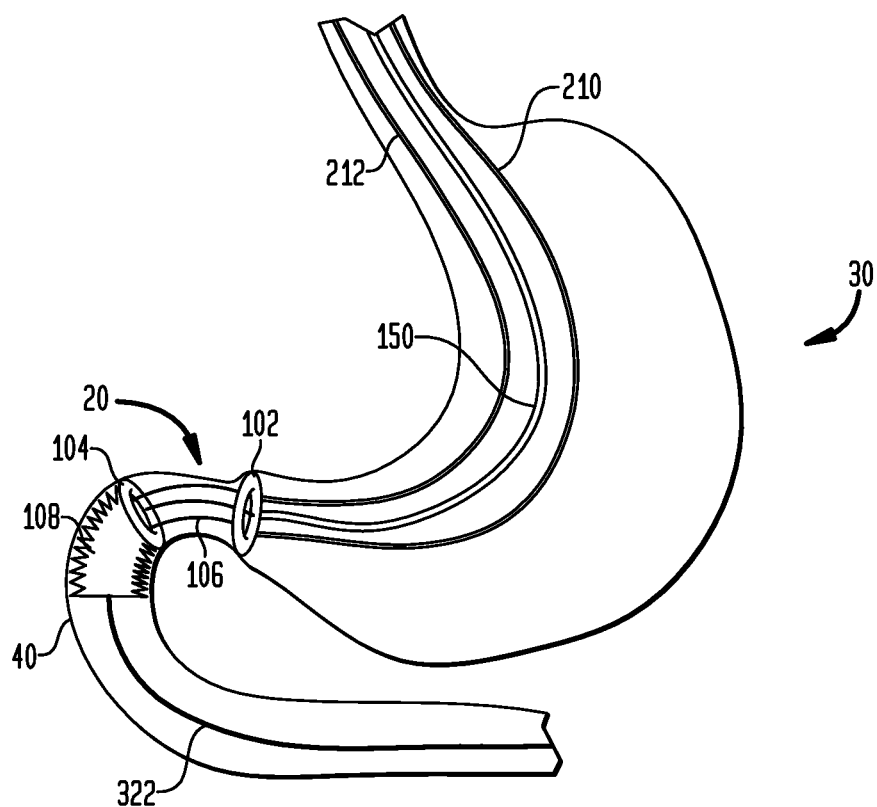
FIG. 14 illustrates the inflation of the gastric and duodenal anchors.

Referring now to FIG. 12, bypass device 100 and delivery system 200 are lubricated and positioned over the guidewire 322 outside of the patient by advancing the proximal end of guidewire 322 through hole 206 in distal capsule 204 and into the inner lumen of support tube 152 (see FIG. 10A). In some embodiments, an overtube (not shown) may be positioned over the guidewire 322 and advanced through the esophagus and into the patient's stomach. The overtube typically has an inner diameter of approximately 16 mm. However, in the preferred embodiment, an overtube is not required for implantation of bypass device 100. A small steerable scope (not shown) may be advanced through the esophagus into stomach 30 through the pylorus and into the proximal portion of the duodenum. The scope is used to confirm the tissue of the stomach, pylorus and duodenum are robust and show not overt signs that they will not tolerate the device. In an exemplary embodiment, a small tube (not shown) may be inserted into the pylorus. The tube includes a distal inner tube-shaped balloon (not shown) that expands to a known diameter with a known volume of saline. In conjunction with the scope images and other prior imaging data, this instrument is used to determine the appropriate size of bypass device 100 to be used, particularly the appropriate size of duodenal anchor.

Referring now to FIG. 12, once the appropriate size bypass device 100 is selected, distal capsule 204 (containing sleeve 108 and duodenal anchor 104) and proximal capsule 202 (containing gastric anchor 102 and at least a portion of columns 106) are then advanced through the esophagus and into the stomach along guidewire 322. Once through the esophagus, distal and proximal capsules 204, 202 separate, but remain flexibly coupled together by columns 106 and fluid tube 210 (note that tubes 210, 212 are not shown in FIG. 12). The capsules 202, 204 are also still aligned with each other by virtue of delivery tube structure 150 and guidewire 322 that remain extending through the entire device 100. Once the entire device is within the stomach, support tube 152 is used to push the distal end of delivery tube structure 150 and distal capsule 204 through the pylorus into the proximal duodenum (see FIG. 13). This may require the use of a dilator (not shown) to maintain the pylorus in its maximum diameter. Alternatively, a separate pusher rod (not shown) may be used to push the distal components of bypass device 100 into stomach 30. It should be noted that it may not be necessary to encapsulate any components of device 100 in order to advance them through the patient's GI tract. In this case, these components will simply be advanced in their deflated configurations.

At this point, the surgeon will wait until capsules 202, 204 dissolve (unless capsules 202, 204 are not being used). It is expected that proximal capsule 202 will dissolve more rapidly, as it is designed to do so, and is subjected to a slightly more caustic environment within the stomach (alternatively, capsules 202, 204 may comprise material that can be excreted naturally by the patient). Once the proximal components of bypass device 100 are freed from capsule 202, a fluid, such as saline, is introduced through fluid tube 212 into the interior of inflatable member 112 until it is filled to the appropriate size (see FIG. 14). After inflating gastric anchor 102, and after distal capsule 204 has also dissolved, fluid is delivered through fluid tube 210 into the interior of inflatable member 132 of duodenal anchor 104 in a similar fashion.

Referring now to FIG. 15, once duodenal anchor 104 has been inflated into its operative configuration, sleeve 108 is advanced through the duodenum and into the jejunum to its final deployment position. Specifically, support tube 152 is used to push sleeve 108 and delivery structure 150 through the patient's small intestines. Once in final position, clamp 158 is released via the actuator device or handle outside of the patient (not shown) to disengage it from the distal end of sleeve 108.

In an alternative embodiment, the surgeon will not wait until distal capsule 204 is dissolved before advancing sleeve 108 to its final deployment position in the small intestines. In this embodiment, once capsule 204 has been advanced through the pylorus into the proximal duodenum, gastric anchor 102 is inflated as discussed above. Capsule 204 is then advanced further into the duodenum until duodenal anchor 104 is forced out of the proximal opening of capsule 204 (anchor 104 will be prevented from further distal movement by gastric anchor 102). Capsule 204 will then be advanced through the duodenum until the distal end of sleeve 108 reaches its final deployment position. Clamp 158 is then disengaged from sleeve 108 and removed from the patient as described above and capsule 204 will eventually dissolve.

Figure 16:
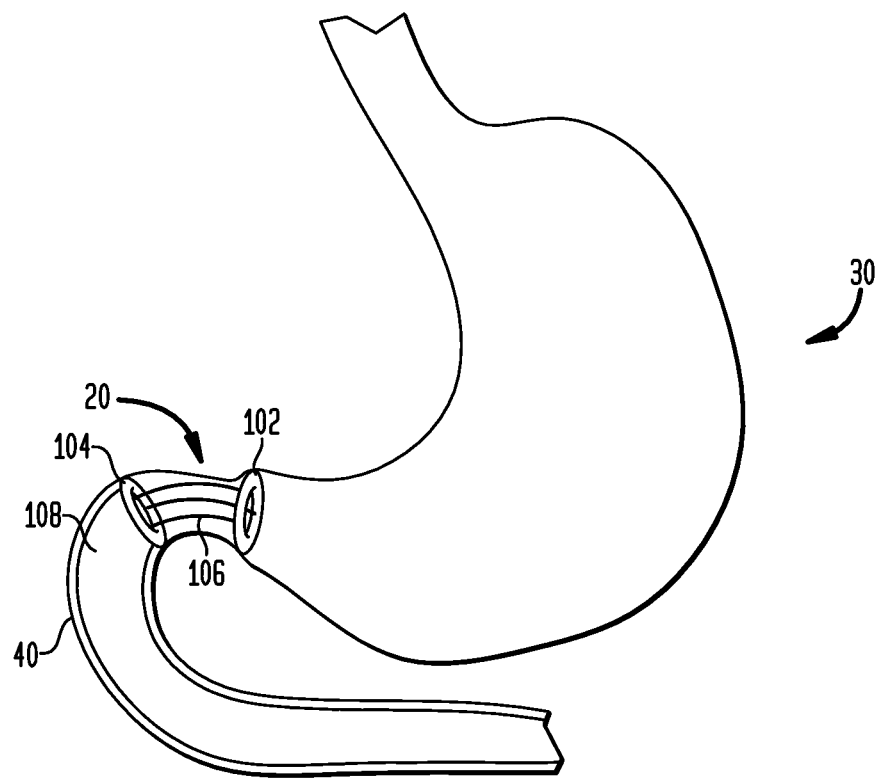
FIG. 16 illustrates the bypass device in place in its operative configuration in the patient.

As shown in FIG. 16, bypass device 100 should now be in its final position with gastric anchor 102 in pyloric antrum of stomach 30 and duodenal anchor 104 just distal to the pyloric sphincter 20. Delivery structure 150 is removed from the patient and the distal end of fluid tubes 210, 212 are cut with scissors or the like and removed. A gastroscope and/or fluoroscope (not shown) may be used to confirm the final placement of device 100. Once device 100 is in place, guidewire 322 can be also removed from the patient.

A method for removing bypass device 100 according to the present invention will now be described. A gastroscope may be advanced through the esophagus and into the stomach 30 of patient in a suitable position for the surgeon to view the procedure. A sharp instrument (not shown) such as scissors or the like, is advanced through the patient's esophagus into stomach 30. The sharp instrument is used to puncture gastric anchor 102 such that the fluid within the interior of membrane 112 exits into the stomach to deflate anchor 102. Alternatively, a syringe or similar suction device (not shown) may be attached to the valve inlet 120 to withdraw the fluid from gastric anchor 102.

Once deflated, gastric anchor is preferably positioned to the side of the antrum. A grasping or cutting instrument (not shown) is advanced through the esophagus to cut each of the pyloric columns 106 to detach gastric anchor 102 from the distal portion of device 100. The last column 106 that is severed will be held by the grasping instrument to ensure that duodenal anchor 104 and sleeve 108 do not migrate in the distal direction after being detached from gastric anchor. At this point, a grasping tool or snare (not shown) is advanced into stomach 30 to grab gastric anchor 102 and gastric anchor 102 is then pulled through the esophagus and removed from the patient.

The sharp cutting instrument is then advanced through the pyloric sphincter 20 to puncture membrane 132 of duodenal anchor 104 to deflate duodenal anchor 104. The grasping instrument may then be used to pull anchor 104 and sleeve 108 into stomach 30. Once duodenal anchor 104 and sleeve 108 are within stomach 30, they may be sliced up and removed or removed as a single unit. Subsequent to the removal of device 100, a scope (not shown) can be used to determine if any tissue injury or insult that has been sustained by the implantation, use, or removal of device 100. Provided no additional access to the stomach, pylorus, or duodenum is required, removal of the scope concludes the procedure.

Alternatively, the duodenal anchor 104 can be deflated without severing columns 106 and removing gastric anchor 102. In this embodiment, the sharp instrument is advanced around gastric anchor 102, through columns 106 and pylorus 20 to duodenal anchor 104. Duodenal anchor is deflated and pulled into the stomach (along with sleeve 108). The entire bypass device 100 may then be removed as a single unit, or it may be sliced up into smaller components to facilitate passage through the patient's esophagus.

Figure 17:
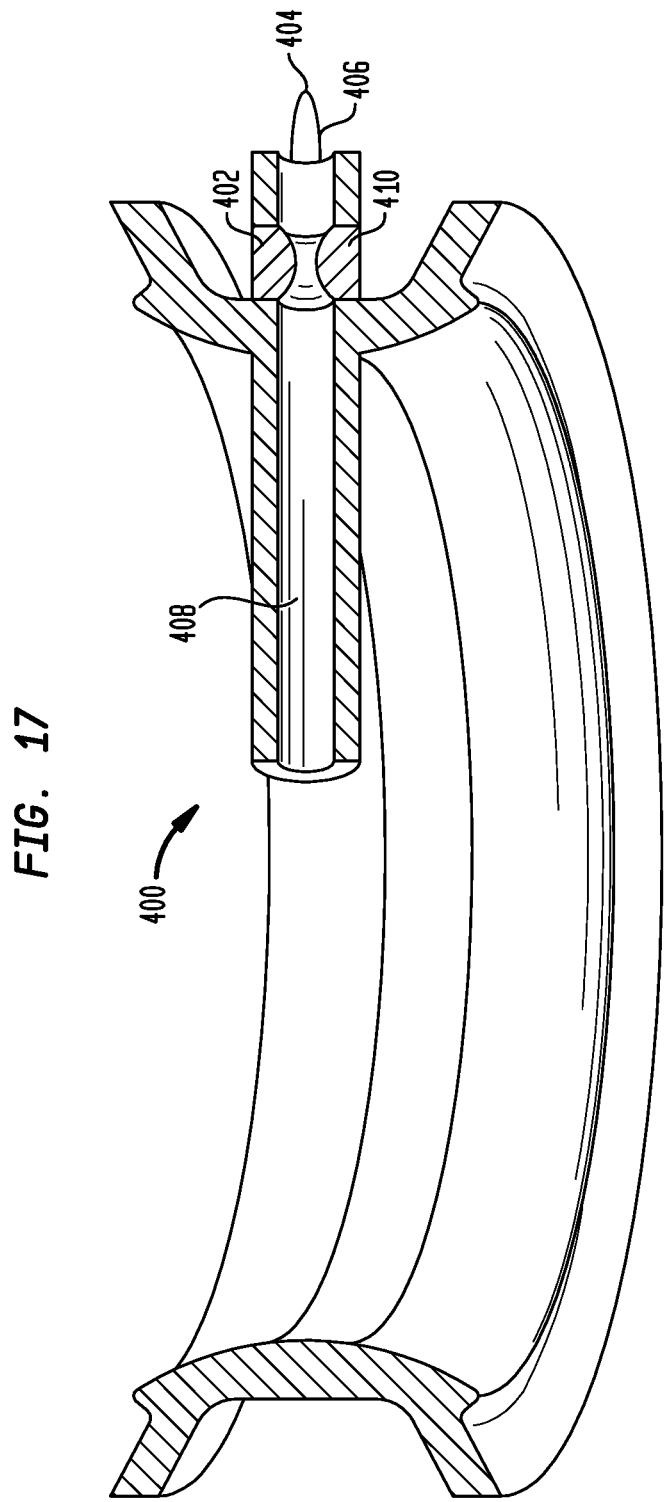
FIG. 17 is a partial cross-sectional view of an alternative embodiment of a valve for the duodenal and gastric anchors of the bypass device.

FIG. 17 illustrates one portion of an alternative embodiment of the gastric and duodenal anchors (for convenience only one of the anchors is shown in FIG. 17). In this embodiment, the anchors both include an outer wall housing a hollow interior designed for inflation as described above. FIG. 17 illustrates a central portion 400 of the outer wall of the anchors. As shown, the anchors further include a valve 402 having an inlet 404, a one-way valve member 406, a fluid passage 408 and an expandable member 410 located within fluid passage 408 between the interior of the anchor and valve member 406. Expandable member 410 preferably comprises a material designed to slowly absorb fluid upon, such as water or saline and expand with the absorbed fluid. In the preferred embodiment, expandable member 410 comprises a hydrogel material although other materials can be used that are well known in the art.

To inflate the anchor, fluid is delivered through inlet 404 such that it passes via fluid passage 408 past expandable member 410 and valve member 406 into the interior of the anchor. Valve member 406 is designed to prevent the fluid from flowing back through fluid passage 408 and inlet 404. As additional protection from this event occurring, however, expandable member 410 will absorb fluid as the fluid fills the interior of the anchor and passes back through passage 408 to saturate expandable member 410. Expandable member 410 is designed to expand when hydrated such that it completely blocks fluid passage 408, thereby preventing any fluid flow in either direction through fluid passage. This not only provides additional protection from fluid leakage, but also prevents any unwanted fluid (such as stomach acid and the like) from passing into the interior of the anchor.

Figure 18:
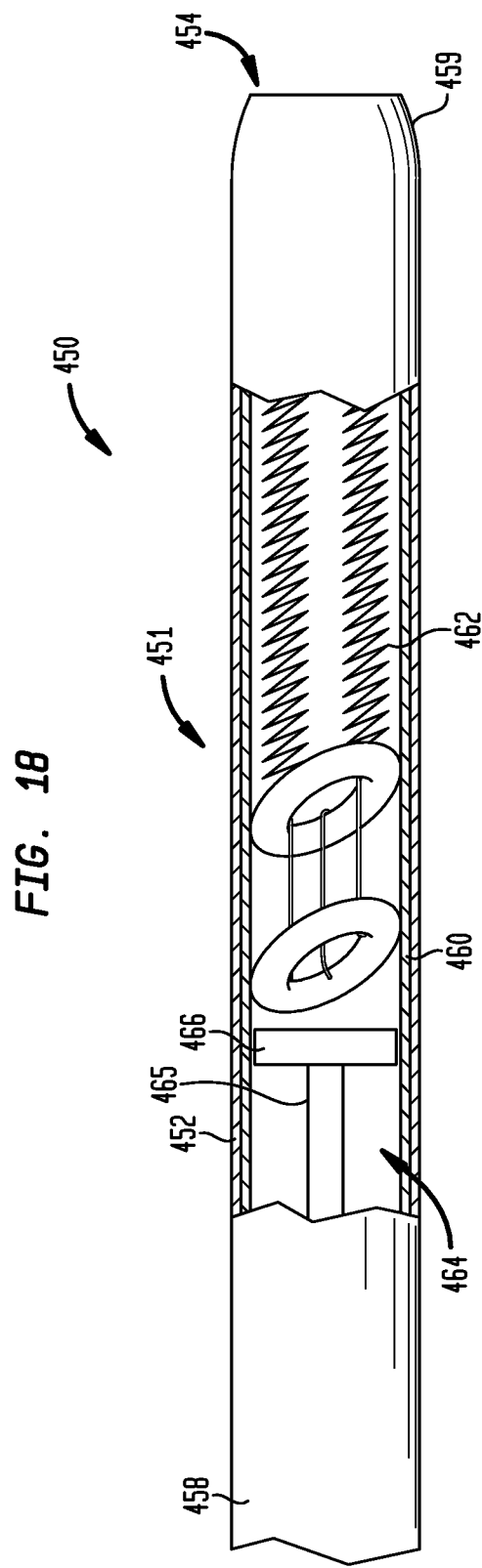
FIG. 18 illustrates an alternative introducer tube for the delivery system of the present invention.

FIG. 18 illustrates an alternative embodiment of a delivery system 450 of the present invention. In this embodiment, system 450 comprises an introducer tube 451 defining an elongate shaft 452 that has sufficient flexibility to extend through a patient's esophagus into the stomach (similar to the overtube described above). Shaft 452 has an open distal end 454 and an open proximal end (not shown as the entire shaft 452 of tube 451 is not shown in FIG. 18) and an internal lumen 458 designed as a working channel for passing instruments therethrough. Tube 451 further comprises a thin flexible bag or sleeve 460 comprising a suitable biocompatible material such as silicone or the like. Sleeve 460 houses a bypass device 462 such as one of the bypass devices described above. Sleeve 460 is preferably long enough to extend entirely through internal lumen 458 of shaft 452 to facilitate placement of sleeve 460 and device 462 in tube 451 (see below). In the preferred embodiment, sleeve 460 has open distal and proximal ends and is fastened to the proximal end of introducer tube 451 such that sleeve 460 remains within tube 451 when device 462 is propelled from tube 451 (see below). Sleeve 460 is also sized to allow it to fit within internal lumen 458 while still housing bypass device 462 in its collapsed configuration.

System 450 may optionally include a pusher or advancing member 464 including an elongate rod 465 with a proximal handle (not shown) and a distal pusher 466 designed to press against a proximal end of bypass device 462 when bypass device 462 is loaded within lumen 458 of tube 451. In some embodiments, handle (not shown) can be used to collapse or expand pusher 466 (discussed below). Tube 451 further comprises a tapered distal end 459 around distal opening 454 to provide for atraumatic advancement through the esophagus.

In use, bypass device 462 is placed within sleeve 460 and sleeve 460 is loaded into the distal end portion of internal lumen 458. In a preferred embodiment, the user extends the proximal end of sleeve 460 through the entire length of lumen 458 and pulls sleeve 460 proximally such that bypass device 462 is pulled into the distal end portion of lumen 458. Once loaded, the device 462 is ready for implantation in the patient.

To implant the device, introducer tube 451 is extended through the patient's esophagus such that its proximal opening 454 is positioned within the stomach. Bypass device 462 is then propelled out of tube 451 into the stomach. This can be accomplished by passing advancing member 464 through proximal opening of introducer tube 451 and advancing it through lumen 458 until it propels bypass device 462 out of the distal opening 454 of tube 451. Alternatively, other devices, such as a gastroscope, can be used to propel bypass device into the stomach.

In the preferred embodiment, sleeve 460 has open proximal and distal ends and is designed to remain within lumen 458 of tube 451 as bypass device 462 is advanced into the stomach. Thus, both sleeve 462 and tube 451 can be easily removed from the patient after device 462 has been deployed. In other embodiments, sleeve 462 passes into the stomach along with device 462 and is then detached or removed from device 462. This can be accomplished by a variety of means, such as cutting the sleeve away from the device 462. Alternatively, sleeve 462 may already include a cut-a-way portion that can be easily detached to open sleeve 462 and allow bypass device 462 to be removed. In yet another embodiment, sleeve 462 may comprise a dissolvable material that dissolves away within the stomach (similar to the capsules discussed above). Once it has been deployed into the stomach, bypass device 462 may be passed along a guidewire and deployed into its final position as discussed above.

In certain embodiments, introducer tube 451 is long enough to extend through the esophagus and stomach and through the pylorus into the duodenum of the patient. In these embodiments, tube 451 may optionally include a bend at its distal end portion to facilitate passage of the tube 451 through the natural bend in the human stomach between the esophagus and the pylorus. Alternatively, the delivery system may include a separate overtube having such a bend. In this embodiment, the separate overtube will be first inserted through the esophagus with a separate straight introducer therein (i.e., to maintain the overtube in a substantially straight configuration as it passes through the esophagus). Once the overtube has passed through the esophagus, the straight introducer is removed such that the overtube is allowed to bend within the stomach into its natural position. At that point, the flexible introducer tube 451 housing the bypass device is advanced through the overtube to the duodenum.

In use, once the distal opening of tube 451 resides in the duodenum, the distal end portions (i.e., the sleeve and the duodenal anchor) of the bypass device are propelled out of the distal opening of the introducer tube 451 and into the duodenum of the patient. The duodenal anchor is then inflated to prevent proximal movement of the distal end portions of the bypass device. The introducer tube 451 is then retracted through the pylorus and into the stomach. As this occurs, the gastric anchor will naturally be pulled out of the distal end of the introducer tube 451 from the counterforce of the inflated duodenal anchor against the distal surface of the pylorus. The gastric anchor may then be inflated within the stomach and the sleeve extended through the duodenum as described above.

In yet another alternative embodiment, the pusher device or advancing member is designed to perform multiple functions. Namely, the pusher device is sized and shaped to fit between the gastric and duodenal anchors within the introducer tube. In this capacity, the pusher device is used to push or propel duodenal anchor and sleeve out of the distal opening of the introducer tube into the duodenum. In addition, the pusher device will function to prevent the gastric anchor from being advanced through such distal opening when the distal opening is located within the duodenum. Once the distal opening of the introducer tube has been retracted through the pylorus into the stomach, the pusher device is designed to collapse and retract proximally through the middle of the gastric anchor. It can then be expanded again to propel the gastric anchor through the distal opening of the introducer tube and into the patient's stomach.

In one embodiment, the pusher device comprises an elongate rod coupled to a umbrella-shaped or claw-shaped proximal pushing device. The rod is sized to extend through the introducer tube and through the center of the gastric anchor. The proximal pushing device is sized to reside between the gastric and duodenal anchors. Distal advancement of the rod will cause the pusher device to propel the duodenal anchor through the distal opening of the introducer tube. The pusher device further comprises an actuator at the proximal end of the rod for collapsing the umbrella-shaped pushing device such that it can be retracted proximally through the center of the gastric anchor. The actuator can then be used to expand the pushing device such that further distal advancement of the rod will cause the pusher device to propel the gastric anchor through the distal opening in the introducer tube.

In yet another embodiment, an alternative method for implanting and removing the bypass devices of the present invention is now described. In this embodiment, the hollow sleeve includes one or more projections at its distal end designed to allow an endoscopic forceps, clips, clamp or similar device to attach to the projections. The projections can be loops, strings, protuberances or the like and are preferably made of the same material as the sleeve (such as silicone). The gastric and/or duodenal anchors may also include such projections for similar purposes.

In use, the bypass device is attached to an endoscopic scope by passing an endoscopic forceps or clamping device through the working channel of the scope and attaching the forceps to the projections on the distal end of the sleeve. The physician may then attach the remainder of the bypass device to the outer surface of the scope with a shroud, sleeve or other fastening device or just simply align the bypass device with the shaft of the scope. Alternatively, the scope may be advanced through the center of the two anchors of the bypass device and the sleeve such that the entire bypass device is positioned around the scope. The scope is advanced with the distal end of the sleeve through the patient's esophagus and stomach and through the pylorus into the duodenum. The remainder of the sleeve and the anchors of the bypass device are thereby pulled into the stomach alongside the scope.

Alternatively, the physician may attach the forceps to the projections on either the gastric or duodenal anchor and advance those portions of the implant through the esophagus first (i.e., passing the device into the stomach backwards). In this embodiment, the physician may then detach the forceps from the bypass device, remove the scope and attach the forceps to the distal end of the sleeve to advance the remainder of the sleeve into the patient's stomach. To avoid retraction of the anchors back through the esophagus, the gastric anchor may be fully or partially inflated after the forceps have been detached from the anchor and before withdrawing the scope through the esophagus.

After the anchors have been advanced into the stomach of the patient, the gastric anchor is preferably either partially or fully inflated as described above to prevent movement of the gastric anchor through the pylorus into the duodenum or through the lower esophageal sphincter into the esophagus. The physician then continues to advance the scope and the distal end of the sleeve through the duodenum to a position near the final target site within the patient's intestines (either in the distal duodenum or the proximal jejunum). At this point, the physician may detach the forceps from the distal end of the sleeve and withdraw the scope and forceps back into the patient's stomach.

To prevent the sleeve from "following" the scope proximally into the stomach, the physician will preferably temporarily fixate the sleeve within the duodenum. According to the present invention, one method of temporarily fixating the sleeve is to use a detachable clip (rather than the forceps described above) to grab the projection on the distal end of the sleeve. Once in position within the duodenum, the clip is opened and attached to mucosal tissue within the duodenum. The clip can then be deployed such that it is no longer attached to its shaft, but instead fastens the sleeve to the mucosal tissue on the inner wall of the intestines. This allows the scope and shaft of the clip device to be withdrawn while the sleeve is fixated within the duodenum.

In certain embodiments, multiple clips may be used to fasten the sleeve to the inner walls of the intestines. The clips may serve the purpose of creating an additional anchor for the device to prevent migration and to ensure that the sleeve remains patent during the period of time it is implanted within the patient. In addition, the clips will preferably be observable under fluoroscopy such that the physician can ensure that the sleeve has remained in place after implantation.

In another embodiment, the sleeve comprises one or more internal lumens extending down a portion of, or the entire length of, the sleeve. The internal lumens are preferably fluidly coupled to one of the flexible columns which are, in turn, fluidly coupled to a valve within the gastric anchor. In an exemplary embodiment, the sleeve will comprise 3 or 4 internal lumens spaced around its circumference. In use, a fluid is delivered through the gastric anchor and column and into the internal lumens of the sleeve. The fluid causes the sleeve to extend fully and inhibits proximal migration of the sleeve when the scope is retracted from the patient's duodenum. In addition, the fluid-filled lumens will ensure that the sleeve remains patent without any kinks or twists along its length.

Once the scope has been retracted from the duodenum, the duodenal anchor is advanced past the patient's pylorus into the proximal portion of the duodenum. Preferably, the scope is used to push the duodenal anchor through the pylorus. Alternatively, the forceps can be attached to one of the projections on either of the gastric or duodenal anchors to push and/or pull the duodenal anchor into position. The duodenal anchor is then inflated as described above.

In yet another alternative embodiment, the sleeve is "self-deploying" through the duodenum. In this embodiment, the sleeve is positioned within the proximal duodenum as described above and then allowed to "self-deploy" and advance through the duodenum into position. In one embodiment, the sleeve comprises internal fluid lumens as described above and the fluid is delivered into the lumens to force the sleeve to extend down the length of the duodenum. In another embodiment, the sleeve comprises a mass at its distal end (e.g., a thickened annular portion of the sleeve, one or more balls or projections attached to the distal end or the like). The mass will advance through the patient's intestines through natural peristalsis and pull the sleeve distally until it is fully extended. In yet another embodiment, the sleeve comprises a dissolvable portion at its distal end that occludes all or a portion of the distal end of the sleeve. In this embodiment, fluid is flushed through the sleeve and because its distal end is occluded causes the sleeve to extend distally. After the dissolvable portion dissolves within the intestines, the distal end of the sleeve is opened up to allow chyme to pass therethrough.

Figure 19:
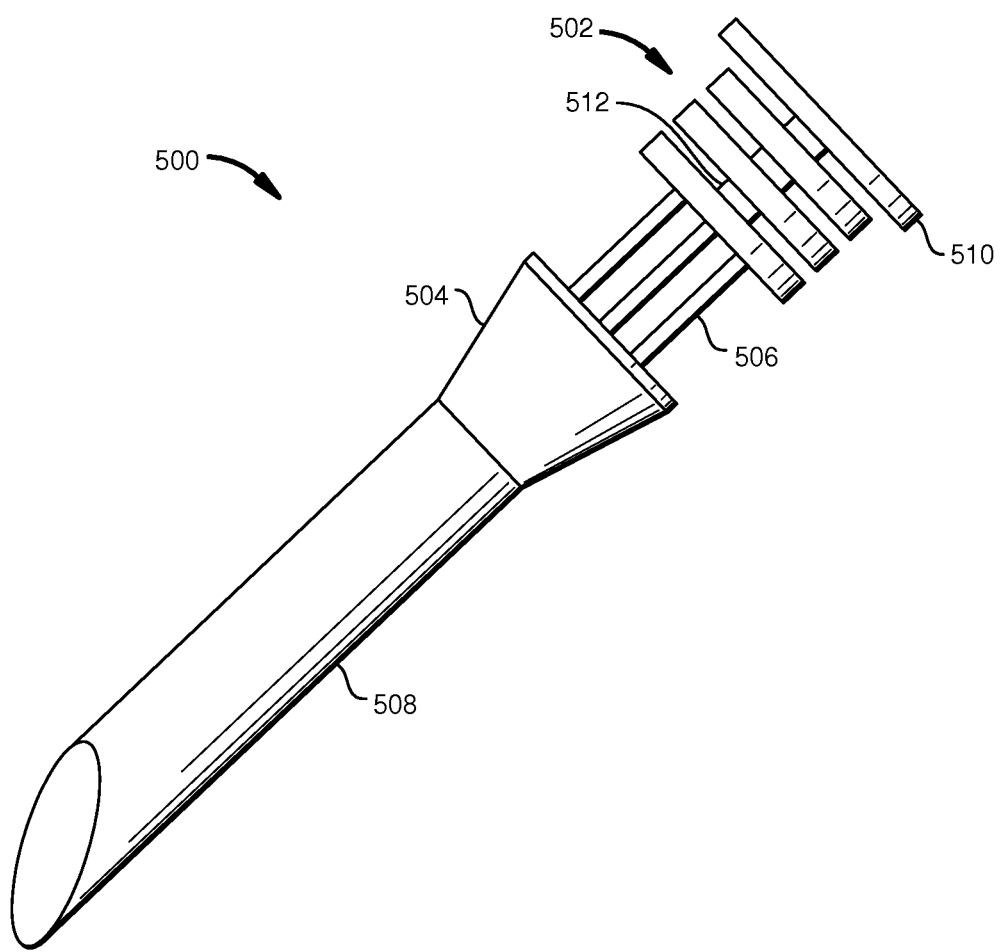
FIG. 19 is a perspective view of an obesity device in an operative configuration according to one embodiment of the present invention.
Figure 20:
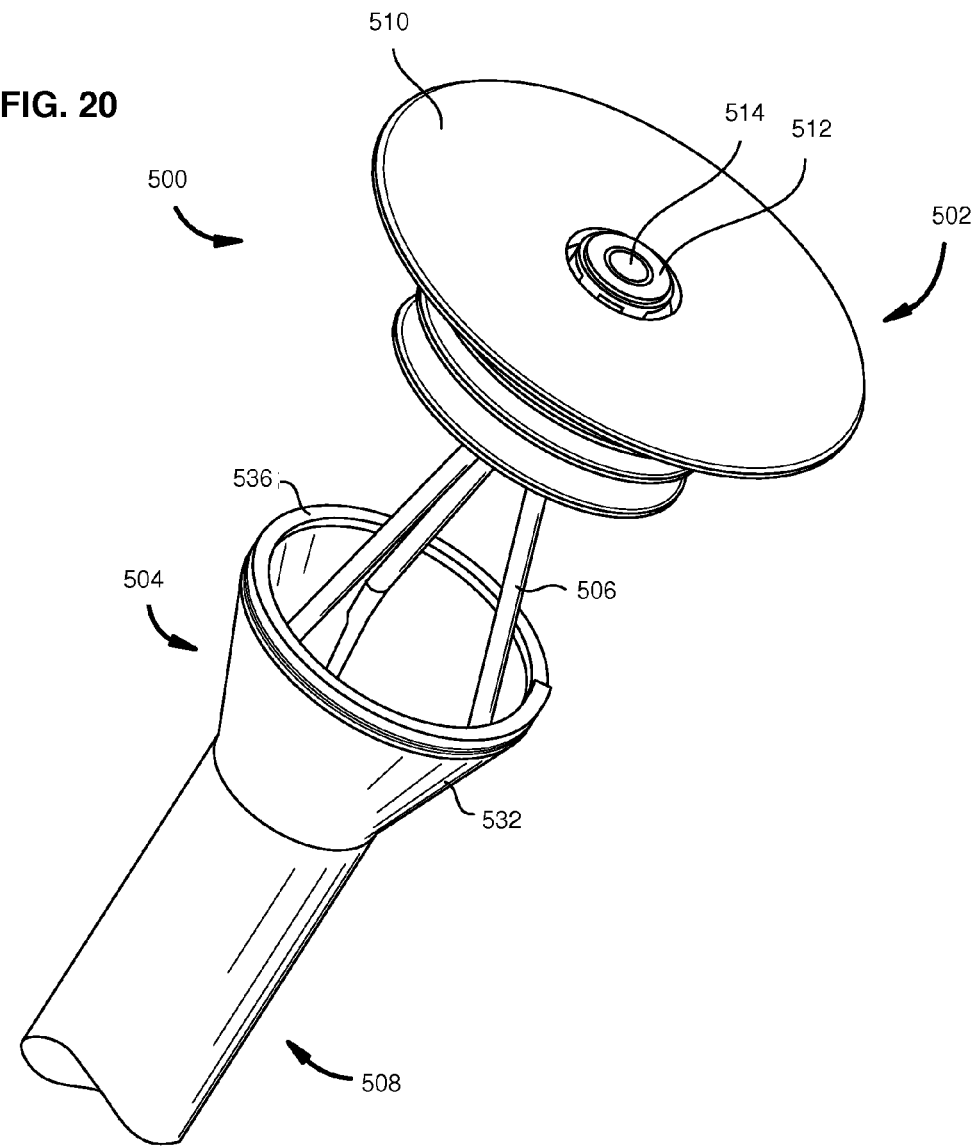
FIG. 20 is a close-up perspective of a proximal portion of the obesity device of FIG. 19.

FIGS. 19 and 20 illustrate an embodiment of an obesity device 500 according to the present invention. As shown, device 500 includes a gastric flow restrictor 502 coupled to a duodenal anchor 504 by a plurality of flexible silicone tethers or pyloric columns 506 and a hollow sleeve 508 coupled to the distal end of anchor 504. Pyloric columns 506 are designed to extend through the pyloric sphincter 20 to allow both flow restrictor 502 and anchor 504 to move back and forth within the stomach 30 and duodenum 50, respectively, with the natural peristalsis motion of the GI tract (see FIG. 36). Pyloric columns 506 may be cylindrical or any other type of prismic shape and are preferably designed such that the distance between the distal end of flow restrictor 510 and the proximal end of anchor 504 is about 30 mm in the fully extended, but relaxed condition. Preferably, device 500 includes three or more pyloric columns 506, which are attached to the distal end of flow restrictor 502, through a button (not shown). The button is preferably comprised of a material having a greater rigidity than the rest of device 500, and may either be co-molded into device 500 or assembled afterward as a separately manufactured component. The button is preferably configured similarly to a conventional button, being disc-shaped and having two or more bores (not shown). The button may be disposed within or adjacent to the distal-most flange. Alternatively, columns 506 may be glued to flow restrictor 502 or coupled to flow restrictor 502 during the molding process, as described above.

Figure 21:
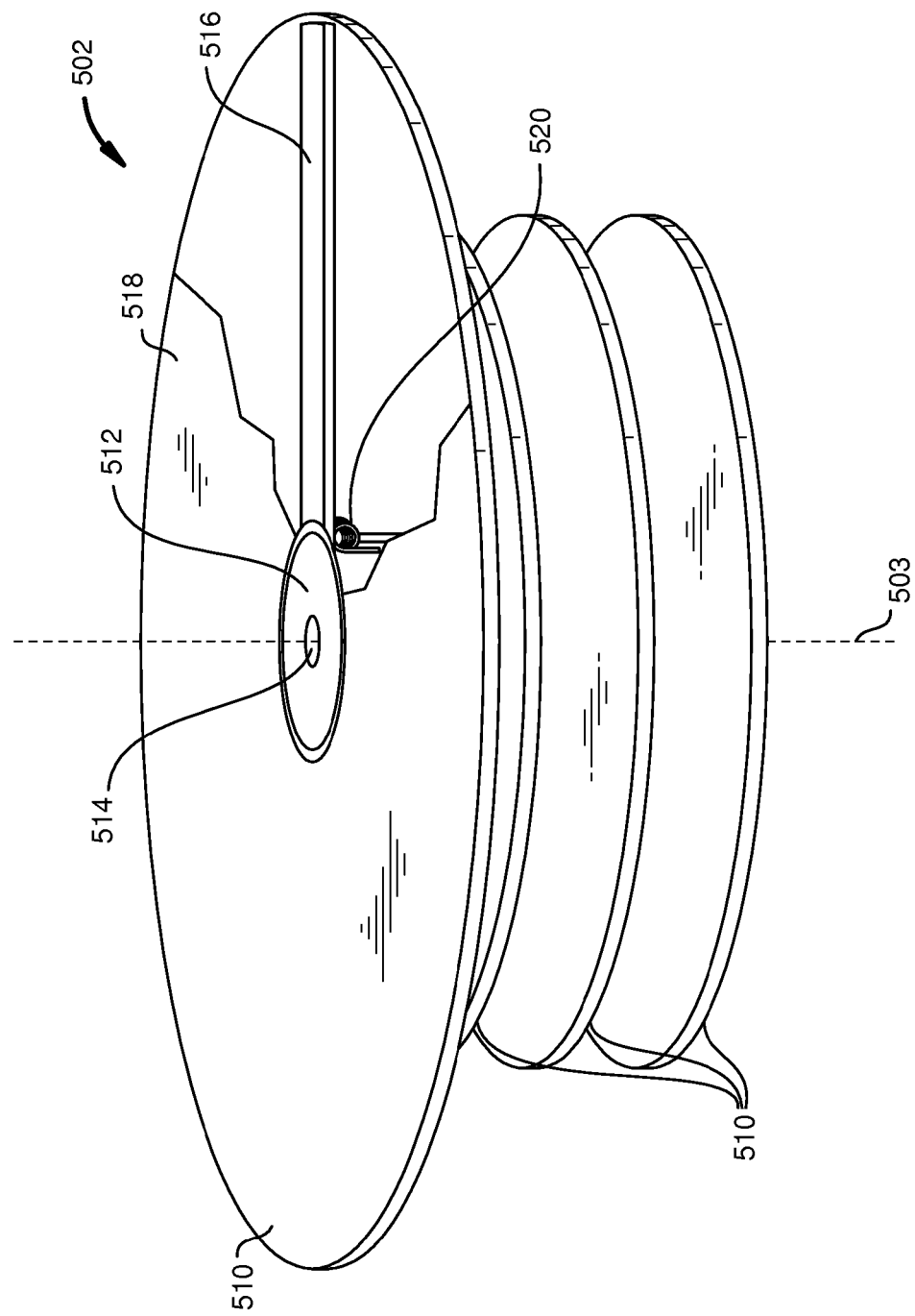
FIG. 21 is a partial cut-a-way top view of a flow restrictor of the obesity device of FIG. 19.

FIG. 21 illustrates one embodiment of gastric flow restrictor 502 in an operative or expanded configuration. Flow restrictor 502 defines a longitudinal axis 503 and comprises one or more flanges 510 coupled to a central tube 512 extending substantially parallel to axis 503. Central tube 512 preferably comprises a moderate durometer silicone approximately 20-50 mm in length and about 4-10 mm in outer diameter. Central tube 512 defines a lumen 514 along axis 503 for passage of a guidewire (not shown) during implantation and removal of obesity device 500 (discussed in detail below). In some embodiments, lumen 514 will have a inner diameter sized to also allow a scope (not shown) with a working channel to pass through. In other embodiments, lumen 514 will be smaller and sized only for passage of a guidewire.

Flow restrictor 502 further comprises one or more discs or flanges 510 extending outward from tube 512 and longitudinally spaced from each other. Flanges 510 may have identical or varying outer diameters, and due to their composition, may flex and bend during positioning of device 500 in stomach 30. Flanges 510 preferably have a thickness of about 1-6 mm and comprise a lower durometer silicone than central tube 512. In the preferred embodiment, obesity device 500 comprises a proximal flange that is larger in diameter than the distal flanges and effectively serves as the proximal surface of the central tube 512. This provides flow restrictor 502 with a shape substantially corresponding to the anatomy of the distal portion of stomach 30. All of the flanges 510 will have an outer diameter larger than the maximum diameter of the pyloric sphincter 20. The proximal flange preferably has an outer diameter of about 40-60 mm, preferably about 50 mm, while the distal flanges preferably have an outer diameter of about 20-40 mm, preferably about 25 mm. Flanges 510 may also bend or flex due to the natural peristaltic action of stomach 30 during contact with surrounding stomach tissue. It should be understood by one of ordinary skill in the art that flanges 510 may be of any configuration that allows flanges 510 to be connected to one another in a generally parallel and stacked configuration while allowing device 500 to be positioned as described below.

As flanges 510 act to control or inhibit the flow of chyme between stomach 30 and duodenum 50, the flow of gasses and other stomach fluids is similarly inhibited. Along with the normal peristaltic action of the surrounding tissue, such gasses may cause a buildup of pressure that may tend to force devices in a distal or proximal direction. Accordingly, flanges 510 may include one or more recesses, semicircular cutaway sections or radial slits (not shown) to aid in relieving such pressure between stomach 30 and duodenum 50 when device 500 is fully inserted by allowing such gasses to pass through the recesses. It is contemplated that the recesses or slits may be staggered circumferentially about flanges 510 without compromising the ability of the recesses to reduce pressure. These radial slits or cutaways may also assist in permitting the flow restrictor to be compressed into an "overtube" for endoscopic placement and/or permit food to pass around flanges 510.

Flanges 510 preferably comprise one or more ribs 516 housed within a relatively flexible covering or frame 518. Ribs 516 are preferably stiff enough to provide support for the flexible covering 518 in the operative position and will define a pivot point near central tube 512 to allow ribs 516 to pivot between the compact and operative positions. In an exemplary embodiment, ribs 516 and covering 518 are molded from a suitable biocompatible plastic, such as silicone. Ribs 516 have a durometer suitable for providing stiffness and support to the device, while frame 518 will have a softer durometer allowing flexibility and minimizing any adverse impact from tissue contact with the flanges.

Each flange 510 is movable between a first or operative position (FIGS. 20 and 21) wherein flanges 510 extend radially outward substantially perpendicular to longitudinal axis 503 and a second or compact position (not shown) wherein flanges 510 bend downward such that they form a small acute angle (almost parallel with) the longitudinal axis. In this respect, flow restrictor 502 operates in a similar manner as an umbrella. In the operative position, flanges 510 are designed to inhibit chyme flow from stomach 30 to pyloric sphincter 20. In addition, since flanges 510 have a larger outer diameter than the inner diameter of pyloric sphincter 20 in its open position, they will prevent distal movement of flow restrictor 502 through pyloric sphincter 20. In the compact position, flanges 510 can be bent downward to substantially reduce the diameter of flow restrictor 502, allowing flow restrictor 502 to be advanced endoscopically through the patient's esophagus (not shown) and into stomach 30, as discussed in more detail below.

Figure 24:
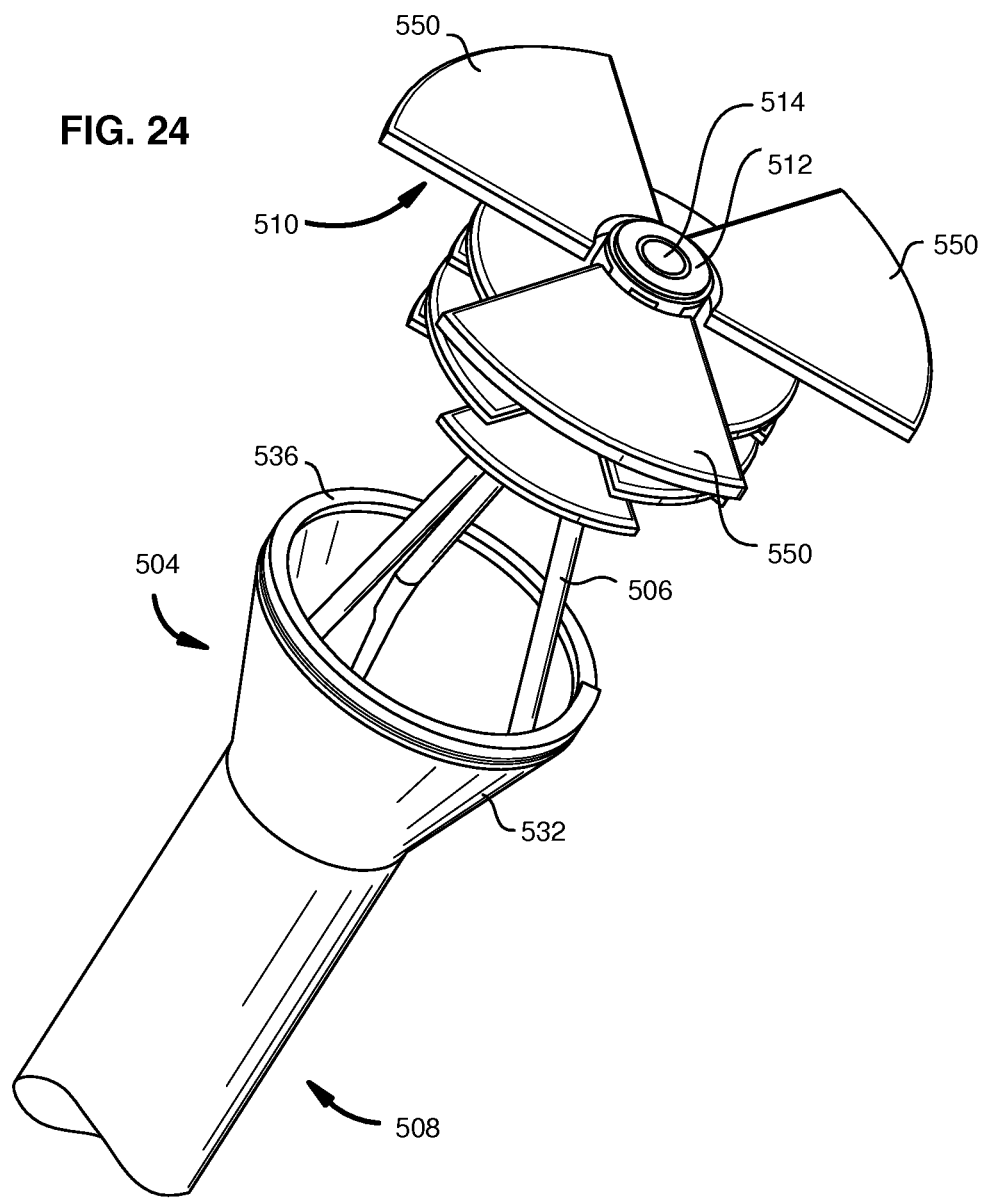
FIG. 24 is a perspective view of an alternative embodiment of a flow restrictor having multiple projections to form a fan-blade shape.

As shown in FIG. 21, frame 518 of each of the flanges 510 has a substantially annular shape. However, it will be recognized that flanges 510 may have a variety of different shapes (e.g., square, triangular, diamond, rectangular, etc). In an alternative embodiment, the frames 518 comprise multiple projections 550 extending radially outward from central tube 512, e.g., a fan blade shape (see FIG. 24), a rose-petal shape and the like. As shown in FIG. 24, projections 550 of each flange 510 are preferably circumferentially spaced from the projections 550 of immediately adjacent flanges along the longitudinal axis 503 of flow restrictor 502. For example, projections 550 of the top or proximal flange 510 are circumferentially spaced from each of the projections 550 in the next flange 510 below the top flange in the direction of the longitudinal axis. In this manner, when projections 550 are folded downward in the compact configuration, they will not interfere with each other, allowing the flow restrictor to conform to a smaller overall diameter in the compact configuration. Alternatively, flanges 510 may have a configuration wherein the projections fold downward in a spiral direction overlapping each other as they are folded into the compact configuration.

Figure 22:
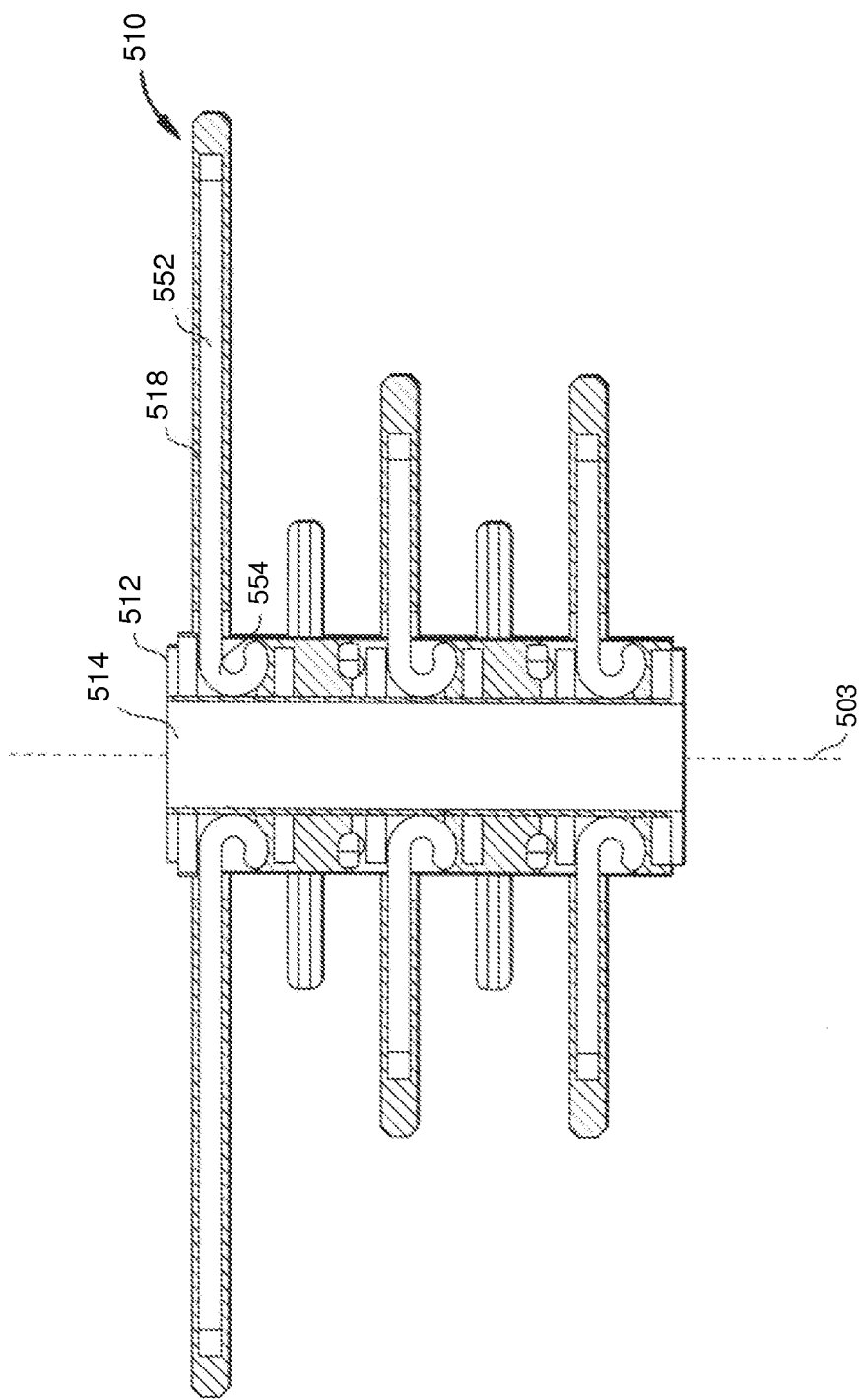
FIG. 22 is a cross-sectional view of an alternative embodiment of a flow restrictor according to the present invention.
Figure 23:
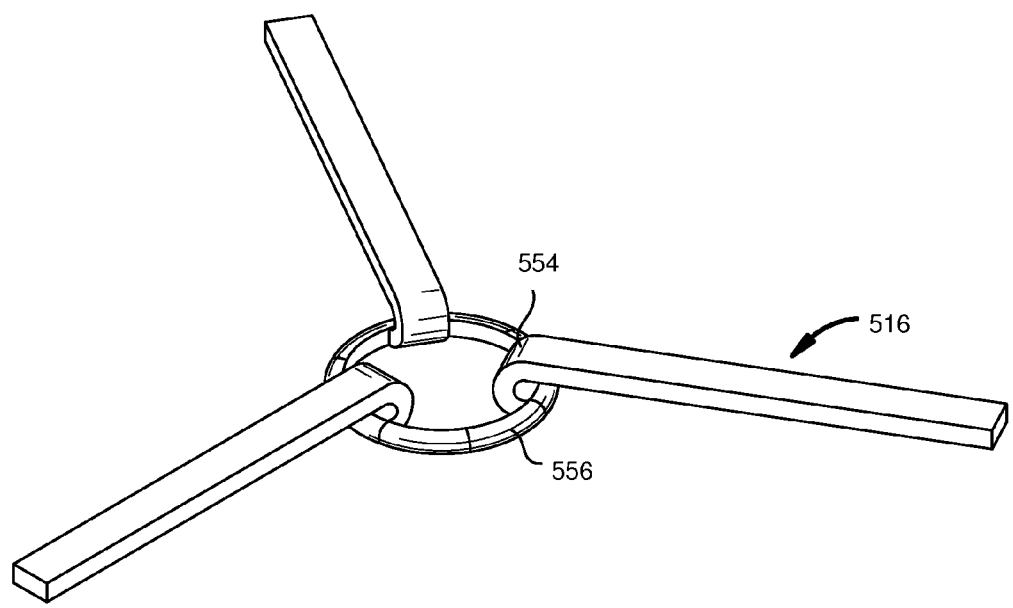
FIG. 23 is perspective view of an interior portion of the flow restrictor of FIG. 22.

In any of these embodiments, flow restrictor 502 further comprises a locking mechanism for locking, biasing or otherwise securing ribs 516 in the operative or expanded position. This ensures that the flow restrictor will remain in the operative position while implanted in the patient. In one embodiment shown in FIG. 21, the locking mechanism comprises a plurality of leaf springs 520 coupled to ribs 516 at pivot points on central tube 512. Leaf springs 520 bias ribs 516 into the operative position. Alternatively, ribs 516 may be designed to bias themselves into the operative configuration. This embodiment is illustrated in FIGS. 22 and 23. As shown, ribs 516 each comprise a rod 552 that extends radially outward in the operative configuration within the frame 518 of each flange 510 as discussed above. In addition, ribs 516 comprise a curved pivot bar 554 that extend around a circular ring 556 coupled to central tube 512. Curved pivot bar 554 operates to bias the rod 552 of each rib 516 radially outward into the operative configuration.

Figure 27:
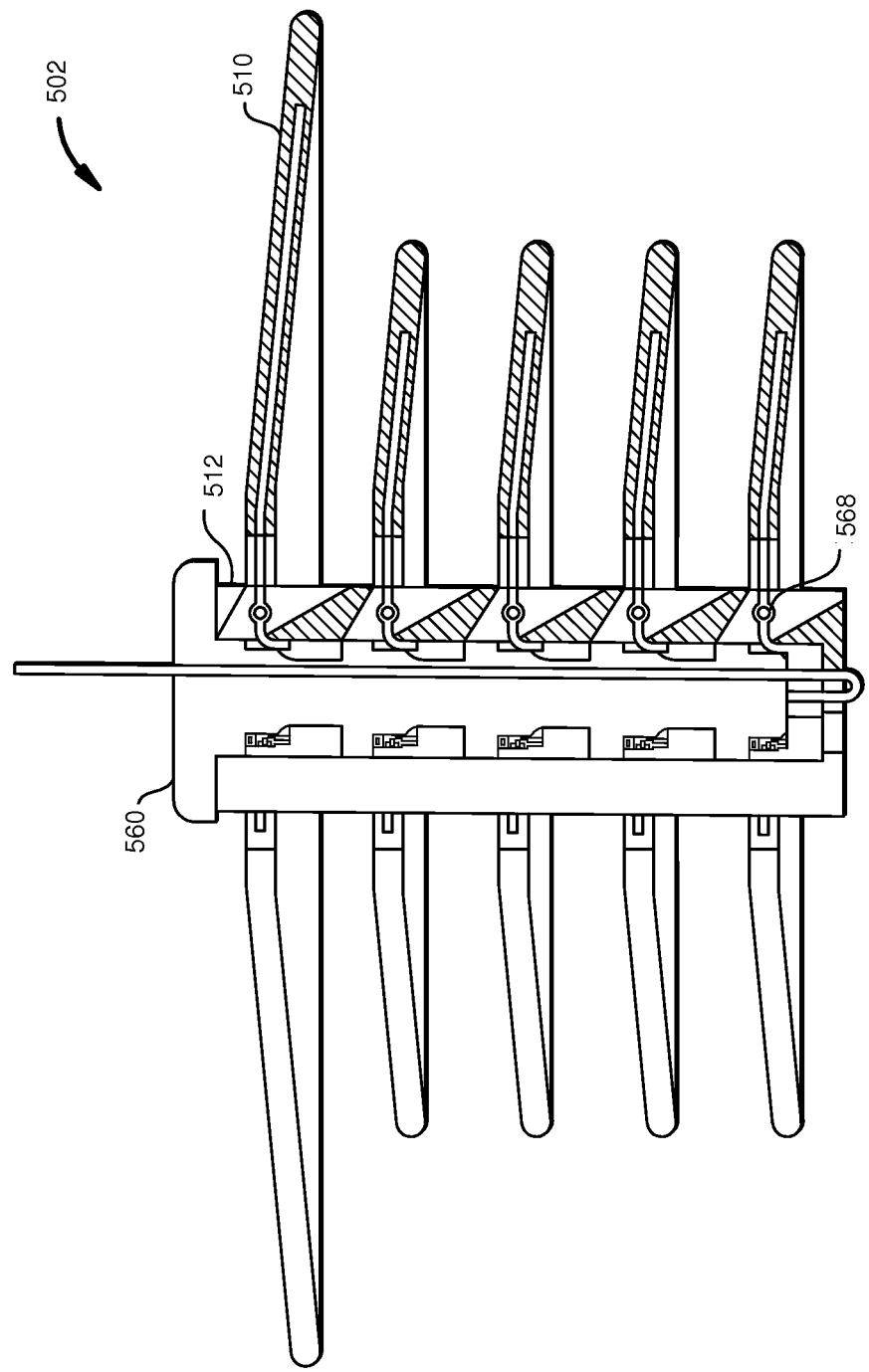
FIG. 27 is a partial cross-sectional view of another alternative embodiment of the flow restrictor according to the present invention.
Figure 28:
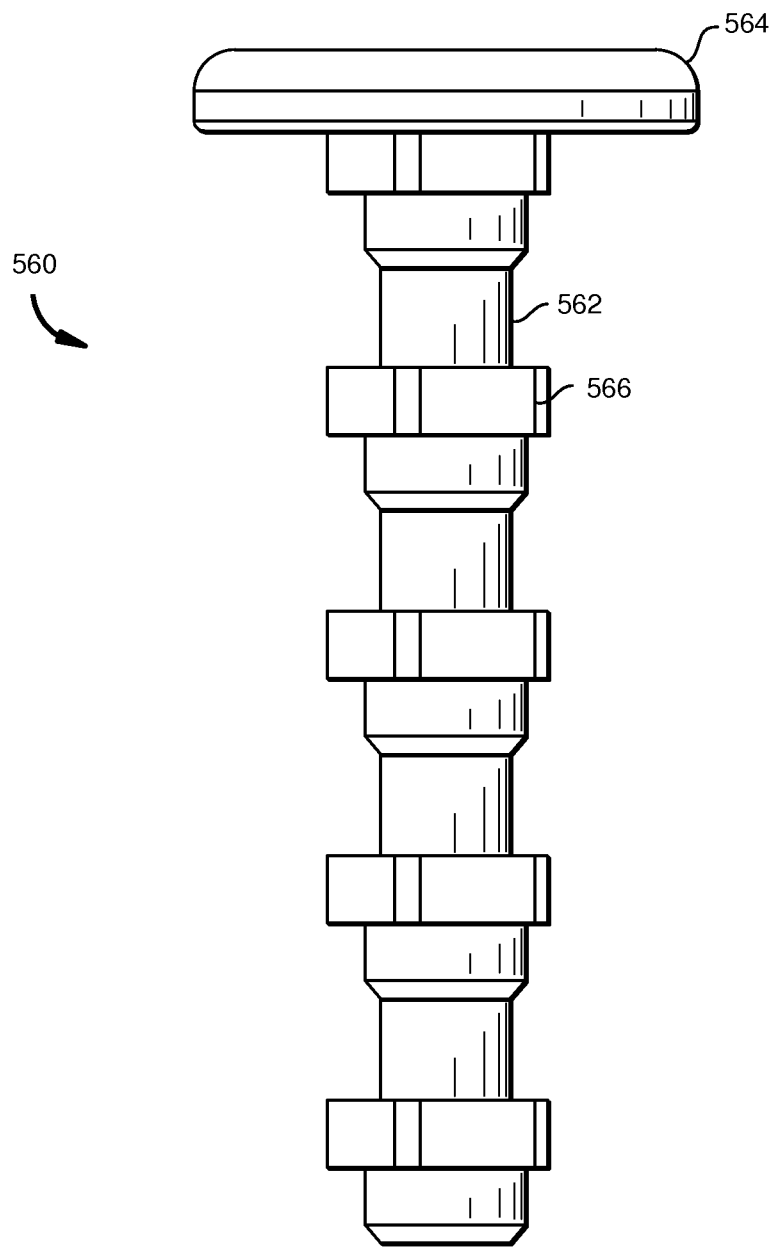
FIG. 28 is a perspective view of a plunger of the flow restrictor of FIG. 27.

Alternatively, the locking mechanism may comprise a separate device that engages the ribs and pivots them into the operative position. FIGS. 27 and 28 illustrate such an embodiment. As shown, flow restrictor 502 comprises a plunger 560 that is extendable through lumen 514 (see FIG. 22) of central tube 512. Plunger 560 comprises a head 564 coupled to a main body 562 with multiple projections 566 extending radially outward from body 562. In this embodiment, ribs 516 each define a rim 568 extending through tube 512 into lumen 514. Projections 566 are designed to engage rims 568 of ribs 516 when plunger 560 is advanced into lumen 514. Upon such engagement, plunger 560 will cause ribs 516 to pivot into the operative position as shown in FIG. 27. Ribs 516 and thereby flanges 510 will remain secured in the operative position so long as plunger 560 remains within lumen 514 of tube 512. Plunger 560 can be locked into place within central opening by any suitable means. When the plunger 560 is removed, ribs 516 are free to pivot such that the user can bend flanges 510 into the compact configuration for insertion or removal into or from the patient.

Figure 25:
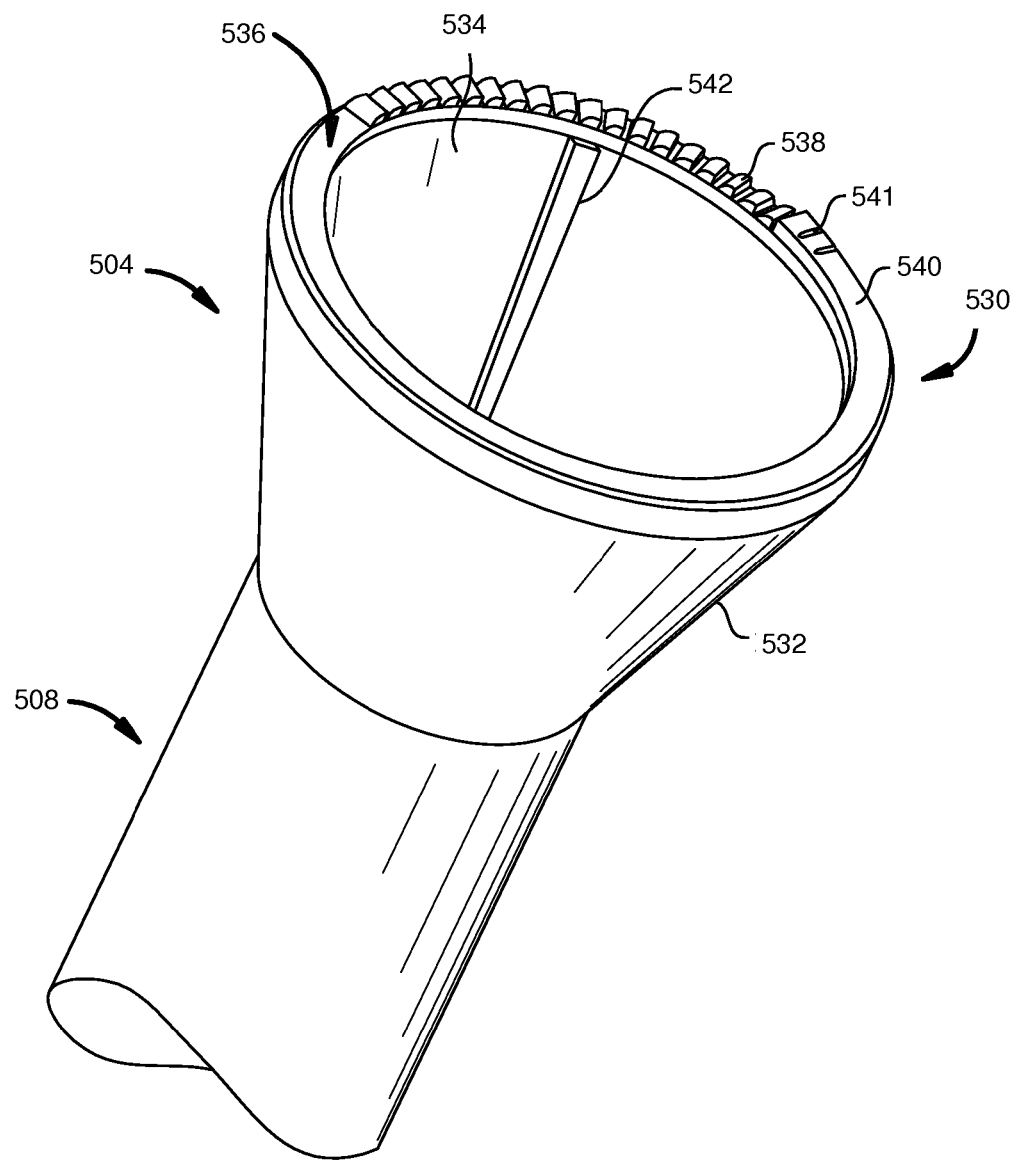
FIG. 25 is a perspective view of an anchor and a sleeve of the obesity device of FIG. 19.
Figure 26:
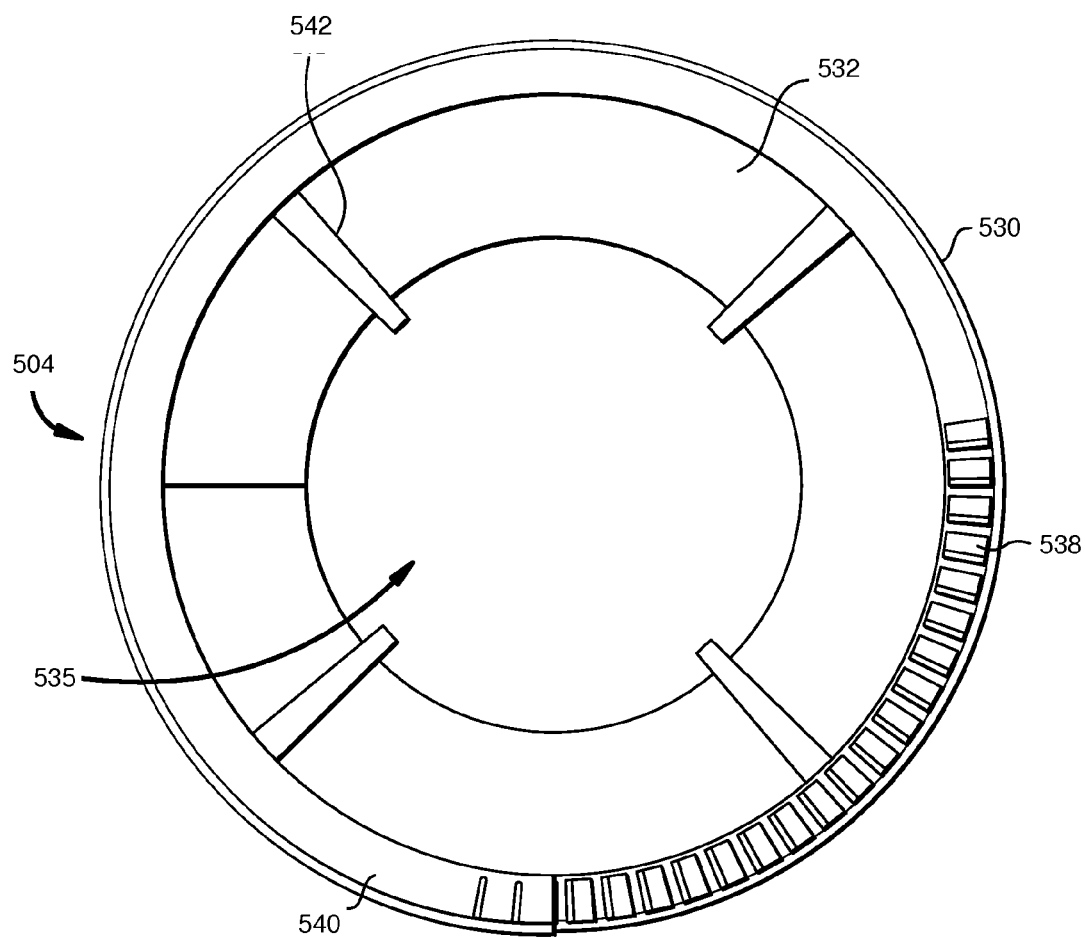
FIG. 26 is a top perspective view of the anchor of FIG. 25.

FIGS. 25 and 26 illustrate one preferred embodiment of anchor 504 and the proximal end of sleeve 508 in the expanded or operative configuration. As shown, anchor 504 comprises a locking member 530 and a tube 532 coupled to and extending distally from locking member 530. Locking member 530 preferably has a harder durometer than tube 532 to provide for a secure anchor against the distal opening of the pyloric sphincter. This ensures that anchor 504 will remain in place within the duodenum 50 despite the natural peristalsis forces acting against anchor 504. Tube 532 preferably has a funnel shape in the operative configuration such that its proximal opening 534 is larger than its distal opening 535 to generally correspond to the narrowing shape of the GI tract distal of the pyloric sphincter. Anchor 504 further comprises one or more bosses or ribs 542 extending from locking member 530 to the distal end 535 of tube 532 at the junction between tube 532 and sleeve 508. Bosses 542 provide structural support for anchor 504. Preferably, bosses 542 will have a slightly harder durometer than tube 532 and anchor 508, but a softer durometer than locking member 530. Bosses 542 will provide an elastic spring such that they will provide distal resistance against natural peristalsis forces pressing tube 532 towards the pyloric sphincter. In addition, bosses 542 provide a natural coupling point for pyloric columns 506 as shown in FIG. 20.

Locking member 530 is designed to move the proximal end of tube 504 between a first or compact position sized and shaped for advancement through the pyloric sphincter into the duodenum and a second or operative position sized and shaped for anchoring against the pyloric sphincter at the proximal end of the duodenum to prevent movement of anchor 504 through the pyloric sphincter. Locking member 530 is preferably designed to allow for movement from the compact position towards the operative position, while preventing the reverse movement back towards the compact position. This locks anchor 504 into the operative position after insertion into the patient. Locking member 530 may be biased towards the operative position, or it may be designed to require a force applied to locking member 530 to move it into the operative position.

In one embodiment (shown in FIGS. 25 and 26), locking member 530 comprises a ratchet having an annular sliding bar 536 coupled to the proximal end of tube 532. Bar 536 has a spiral configuration and is designed for circular displacement over itself. Bar 536 includes teeth 538 that engage a catch (not shown) within a hollow section 540 of bar 536 to allow for movement of bar 536 in the clockwise direction, but prevent reverse movement in the counterclockwise direction. Thus, as bar 536 rotates clockwise, its outer diameter increases to increase the outer diameter of proximal opening 534 of tube 532. Bar 536 can be expanded outward with a force applied to its inner surface (e.g., from a separate balloon designed for such purpose as discussed in detail below). Hollow section 540 of bar 536 further comprises a tab 541 that can be removed to release bar 536 from teeth 538 and allow for compression of anchor 504 during removal of the device (discussed below).

In an alternative embodiment, the locking member comprises a bar member that is movable between a substantially spiral configuration to a substantially circular configuration. In exemplary embodiments, the locking member will have multiple operative positions such that the physician can appropriately size the anchor depending on the anatomy of the individual patient.

Figure 29:
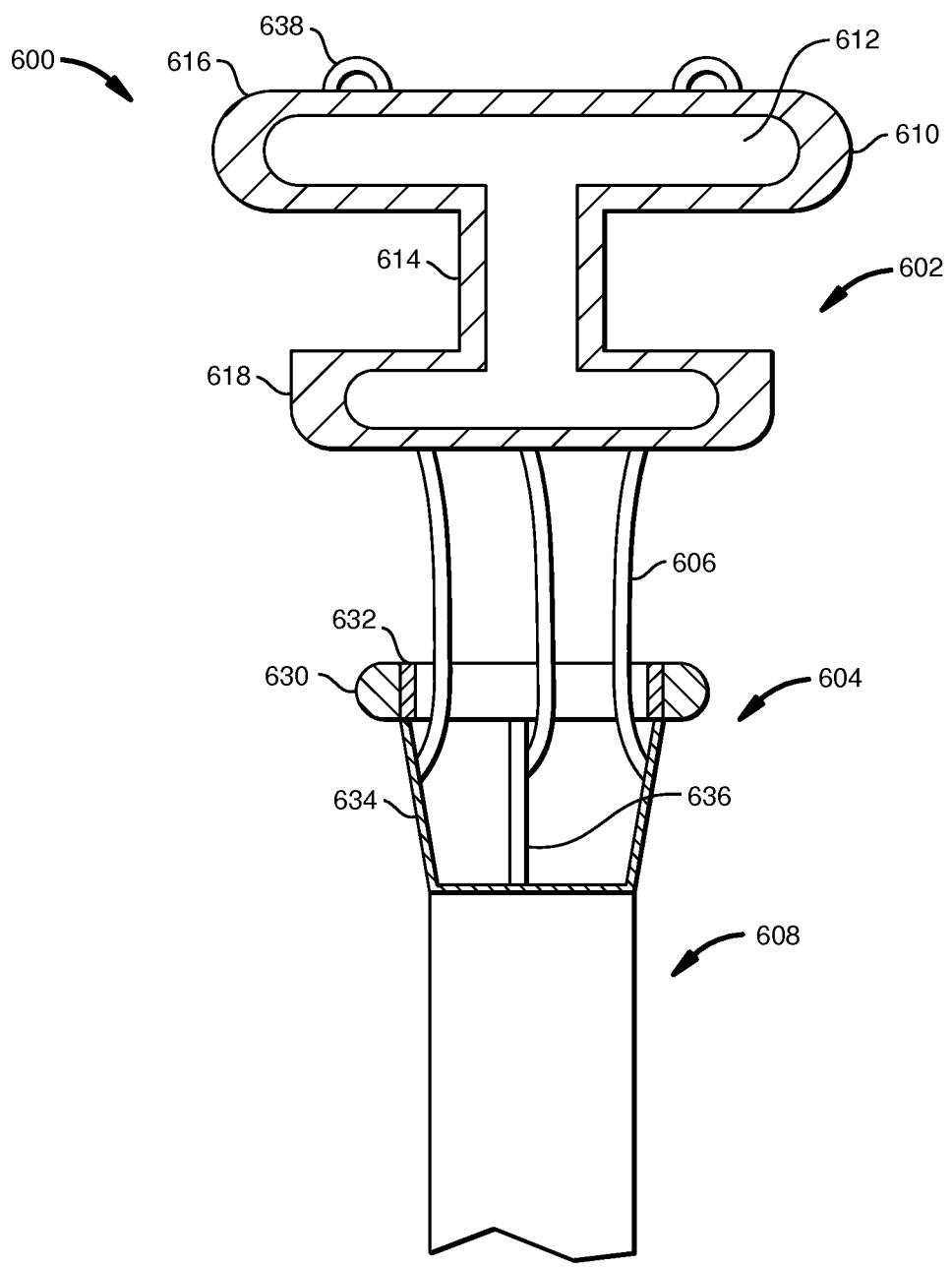
FIG. 29 is a cross-sectional view of yet another alternative embodiment of the obesity device of the present invention.
Figure 30:
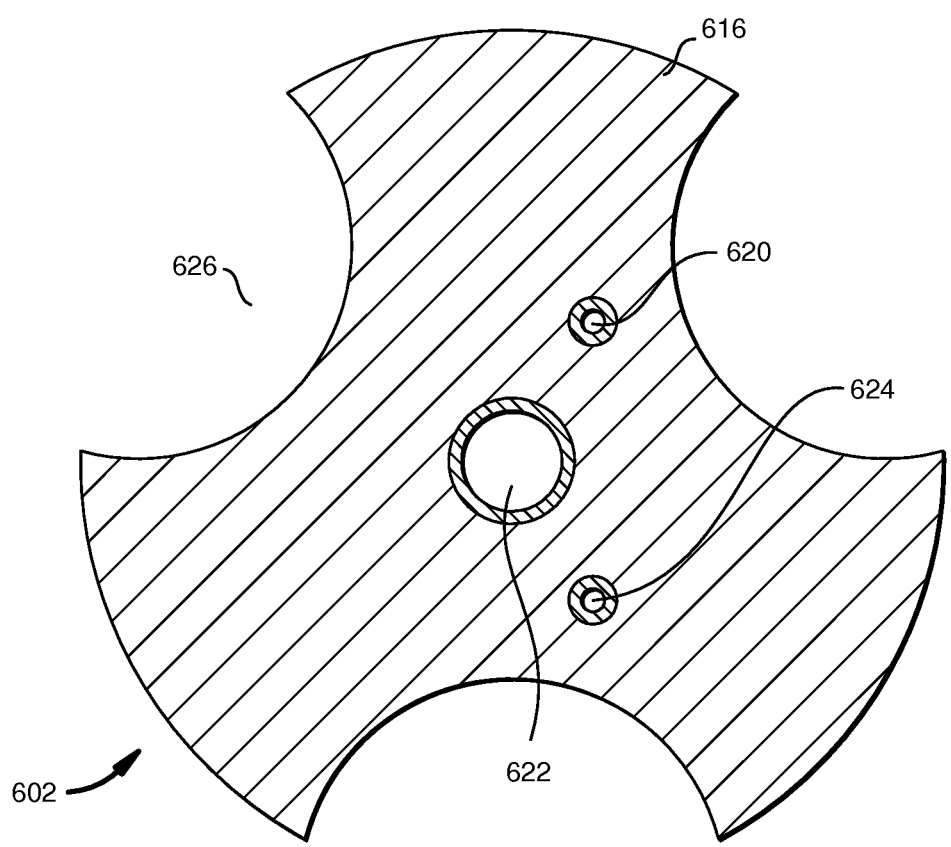
FIG. 30 is cross-sectional top view of a flow restrictor of the obesity device of FIG. 29.

FIGS. 29 and 30 illustrate an alternative embodiment of an obesity device 600 that is inflated into the operative configuration. As shown, obesity device 600 comprises a flow restrictor 602 coupled to an anchor 604 with a plurality of pyloric columns 606, and a hollow sleeve 608 coupled to anchor 604 (only the proximal portion of sleeve 608 is shown in FIG. 29). In this embodiment, flow restrictor 602 comprises an outer collapsible shell 610 surrounding a hollow interior section 612. Collapsible shell 610 is movable between the inflated or operative configuration shown in FIG. 29 to a deflated or collapsed configuration (not shown) for placement and removal from the patient. Collapsible shell 610 has a roughly cylindrical inner core portion 614 with proximal and distal flanges 616, 618. Shell 610 preferably comprises a moderate durometer silicon with a wall thickness of about 0.5-4.0 mm, preferably between about 1-3 mm. Flanges 616, 618 are rounded at the circumference to provide atraumatic contact with tissue and are spaced from each other by about 10 to 40 mm, preferably between about 20 to 25 mm. Proximal flange 616 preferably has an outer diameter of about 40-60 mm and distal flange preferably has an outer diameter of about 25-35 mm. Flanges 616, 618 preferably each comprise one or more semicircular cutaways 626 to permit food passage and retrograde fluid pressure relief.

Interior section 612 is fluidly coupled to a tube 620 having an opening (not shown) at the proximal surface of proximal flange 616 for inflating interior section 612 into the operative configuration shown in FIG. 29. Tube 620 comprises a one-way valve (not shown), such as an umbrella valve, to ensure that fluid delivered into interior section 612 will not pass out of tube 620 after flow restrictor 602 has been inflated. Core portion 614 has an outer diameter of approximately 3-15 mm, preferably between about 4 to 6 mm, and a length of about 25-35 mm when interior section 612 is fully inflated. Flow restrictor 602 preferably includes a pair of protuberances 638 at its proximal end that can be grabbed by a simple grasping instrument to pull/manipulate the device as required during implantation/removal.

As shown in FIG. 30, a hollow tube 622 extends through the central axis of flow restrictor 602. Tube 622 preferably comprises a hard plastic wall with an interior diameter of about 2-4 mm. Tube 622 provides stiffness to flow restrictor 602 as well as providing a lumen for guide wire and instrument access through flow restrictor 602 to the distal components of obesity device 600 (discussed below). In addition, a fluid lumen 624 extends through flow restrictor 602 to allow for fluid passage through one of the fluid columns 606 to inflate anchor 604 as discussed below. Fluid lumen 624 will also comprise a one-way valve (not shown) to ensure that anchor 604 remains inflated during operation of the device. Alternatively, interior 612 of flow restrictor 602 may be fluidly coupled to the interior of anchor 604 or a separate exterior fluid line (not shown) may be used to deliver fluid into anchor 604 (discussed in more detail below with respect to the embodiment shown in FIGS. 31-32).

In this embodiment, anchor 604 comprises an inflatable annular tube 630 coupled to an internal support ring 632 and a funnel 634. Inflatable tube 630 is movable between a collapsed position for advancement through the pyloric sphincter and an expanded or inflated position wherein tube 630 has an outer diameter that is greater than the maximum diameter of the pyloric sphincter in its open position to prevent proximal migration of anchor 604 through the pyloric sphincter. Internal support ring 632 has a diameter slightly less than the maximum diameter of the pyloric sphincter and comprises a harder durometer silicone to provide stiffness and support to tube 630. In particular, support ring 632 ensures that tube 630 maintains a substantially circular shape as it encounters intestinal forces such that the tube 630 cannot be squeezed back through pyloric sphincter by the peristalsis forces within the small intestine.

Inflatable tube 630 is preferably fluidly coupled to one or more of the bosses 636 extending from proximal to distal ends of anchor funnel 634. Bosses 636, in turn, are fluidly coupled to one or more of the pyloric columns 606, i.e., through internal lumens in one or more of the bosses 636 and columns 606. Bosses 636 preferably have some elasticity and will provide stiffness to the overall funnel shape such that anchor 604 cannot be twisted into a smaller configuration for proximal migration through the pyloric sphincter. The boss 636 that includes a fluid lumen is fluidly coupled to internal lumen 624 in flow restrictor 602. Internal lumen 624 preferably has an inlet (not shown) at the proximal end of flow restrictor 602 allowing the physician to deliver fluid to lumen 624 and thus inflatable tube 630. In an exemplary embodiment, the one-way valve will be positioned at the proximal end of internal lumen 624 rather than within inflatable tube 610 as discussed above. In this embodiment, the one-way valve will preferably have a mechanism that will allow for opening of the value and removal of fluid from device 600 during removal of device 600 from the patient (discussed in detail below).

In addition to, or as an alternative to, the one-way valve, a curable fluid, such as silicone, may be injected into the fluid pathway after the saline. The curable fluid will cure and harden, thereby preventing any fluid egress from the interior of tube 630. In another embodiment, the inflatable members of the flow restrictor and/or the anchor may comprise a material that self-seals when punctured with a very sharp small instrument such as a syringe. In this embodiment, the inflatable members of the obesity device may simply be inflated with a syringe and then self-sealed by the material to prevent fluid egress.

Figure 31:
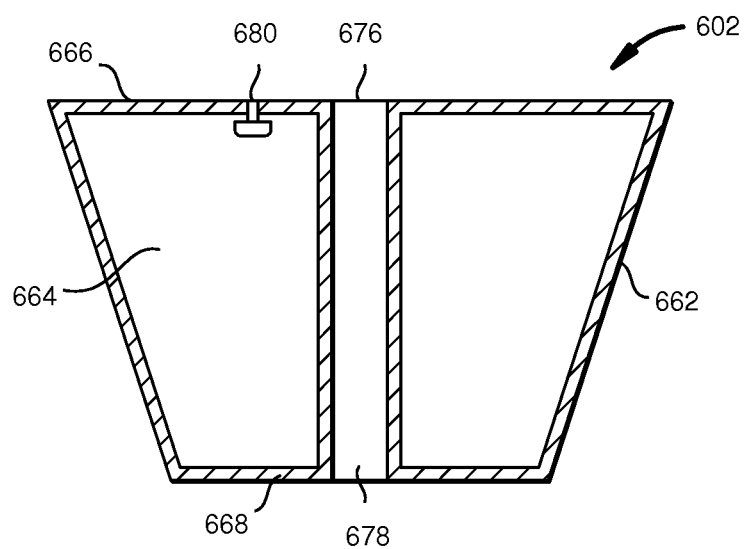
FIG. 31 is a cross-sectional view of another alternative embodiment of a flow restrictor for the obesity device of the present invention.
Figure 32:
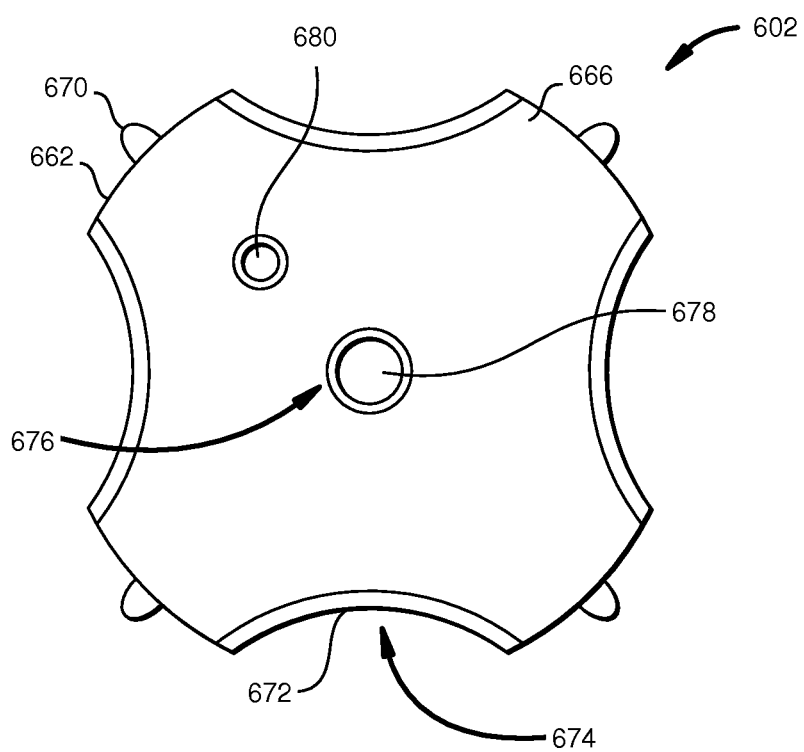
FIG. 32 is a top view of the flow restrictor of FIG. 31.

Referring now to FIGS. 31 and 32, another preferred embodiment of a flow restrictor 660 is illustrated. Similar to the previous embodiment, flow restrictor 660 comprises an inflatable outer membrane 662 surrounding a hollow interior 664 such that membrane 662 can be inserted into the patient's stomach in a deflated or collapsed configuration and then inflated into the operative configuration. In this embodiment, membrane 662 comprises a relative thin flexible material, such as silicone, preferably having a wall diameter of about 0.1 to 1 mm thick. Flow restrictor 660 further comprises proximal and distal sheets 666, 668 that may be molded with, or glued to, membrane 662 as discussed. Alternatively, sheets 666, 668 and membrane 662 may be constructed as a single piece such that membrane 662 constitutes the entire outer wall of the structure. Proximal and distal sheets 666, 668 preferably have a slightly greater thickness (e.g., preferably between about 0.5 mm to 2.0 mm) and stiffness than membrane 662 to provide flow restrictor 660 with support and to hold its annular shape in the operative configuration.

Flow restrictor 660 further comprises one or more ribs or bosses 670 and one or more support members 672 extending along membrane 662 from proximal sheet 666 to distal sheet 668. Bosses 670 and support members 672 preferably comprise a slightly thicker silicone material (i.e., preferably about 1.0 mm to 2.0 mm thick) and provide further support to the overall structure of flow restrictor 660. In an exemplary embodiment, support members 672 have an arcuate shape and form cut-a-ways or recesses 674 in the otherwise conical shape of flow restrictor 660. Recesses 674 provide paths for passage of chyme in stomach 30 past flow restrictor 660 to the pyloric sphincter and for passage of gases and/or fluids between the stomach and the duodenum. In the exemplary embodiment, bosses 670 are formed on the outside surface of membrane 662 and support members 672 are formed within the inner surface of membrane 662. However, it will be recognized by those skilled in the art that a variety of different configurations can be employed to provide structure to flow restrictor 660 in the inflated configuration.

Flow restrictor 660 further includes a central tube 676 having an inner lumen 678 extending along its longitudinal axis and a one-way valve 680 with an opening in distal sheet 666. Central tube 676 preferably has a wall thickness of about 0.1 mm to 1 mm and an inner diameter of between about 2 mm to 4 mm. Central tube 676 provides additional structural support for flow restrictor 660 and also provides a lumen for passage of a guidewire and/or other instruments, such as a gastroscope. One-way valve 680 is configured for coupling to a fluid tube (not shown) for delivering a fluid, such as saline, to the interior 664 of membrane 662 for inflation of flow restrictor 660.

In reference to FIGS. 33-39, a method of implanting and removing an obesity device 800 (similar to one of, or a combination of, the embodiments shown in FIGS. 19-32 according to the present invention will now be described. While the description of this method will be specifically directed to the embodiments illustrated above, it will be understood by those skilled in the art that this method (or similar methods) can be used to implant and remove all of the embodiments of the present invention, including embodiments or designs that may not be specifically described or illustrated herein.

Figure 36:
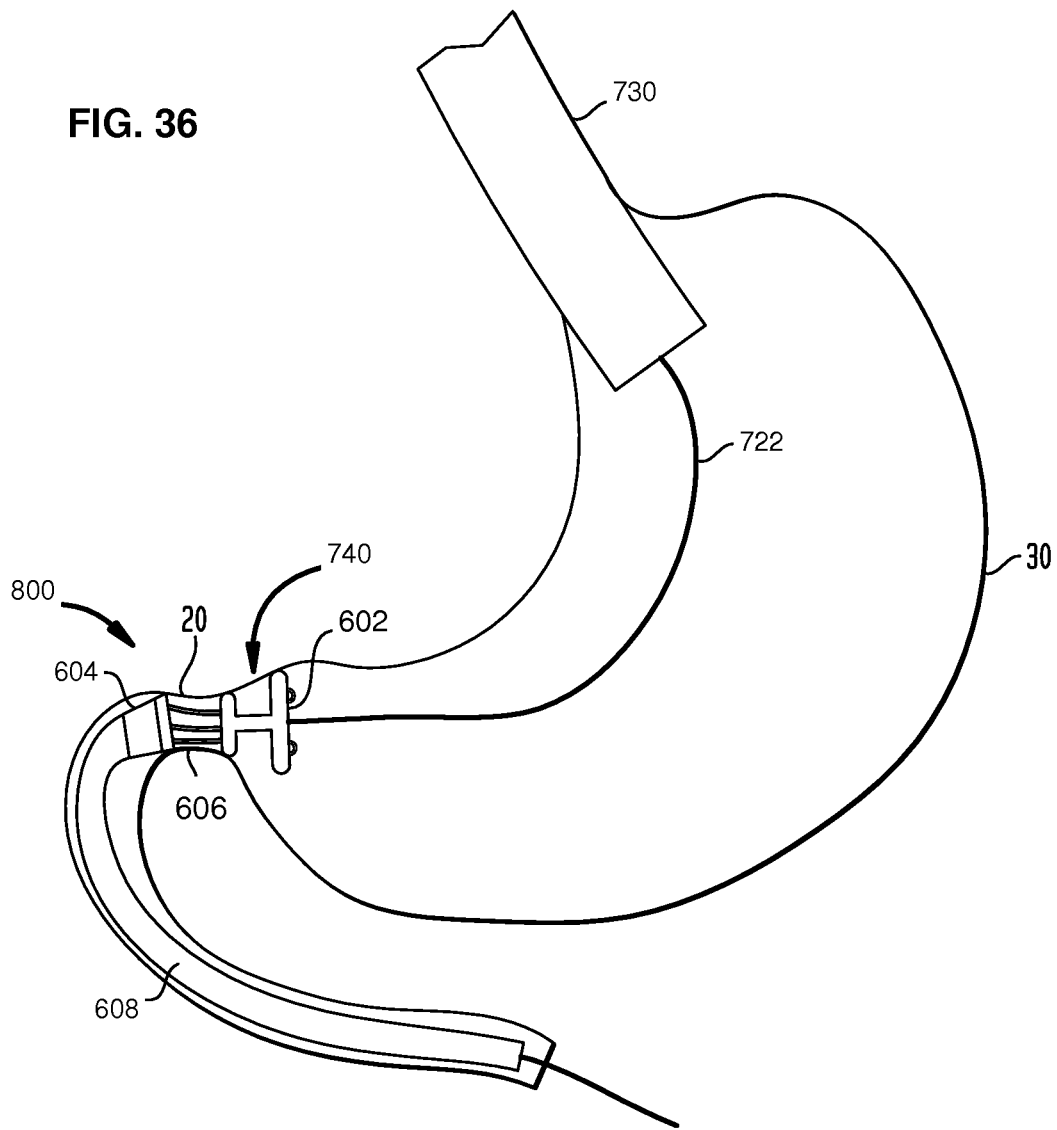
FIG. 36 illustrates the obesity device in place in its operative configuration in the patient.

Device 800 enters and exits the patient through esophagus 702 and is ultimately positioned in its operative state, wherein pyloric columns 606 (shown in FIG. 29) extend through pyloric sphincter 20 (e.g., see FIG. 36). In certain embodiments, flow restrictor 602 (FIG. 29) and anchor 604 (FIG. 29) are separately encapsulated for implantation such that each may be independently released. Ideally, anchor 604 is released first such that anchor 604 and sleeve 608 (FIG. 29) are advanced as a single uninflated structure into the duodenum, coupled to flow restrictor 602 by columns 606. The flow restrictor 602 is then inflated following the proper positioning of anchor 604 and sleeve 608. In other embodiments, the flow restrictor and anchor are not encapsulated and are simply advanced through the esophagus or the overtube in their deflated configurations.

Figure 33:
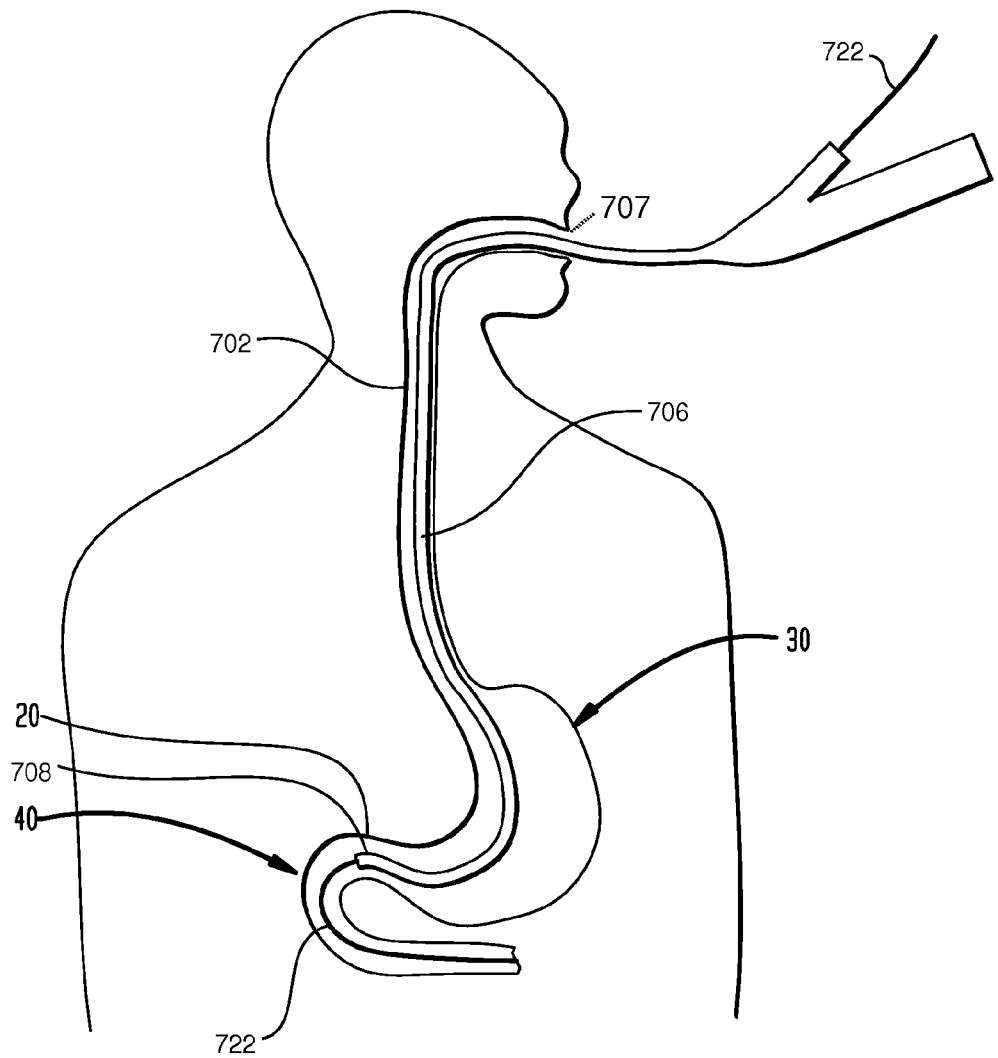
FIG. 33 illustrates the insertion of a gastroscope and guidewire through an esophagus of a patient.

Initially, a gastroscope 706 is lubricated, inserted into patient's mouth 707, and fed through esophagus 702 and the gastroesophageal ("GE") junction into stomach 20, as shown in FIG. 33. Gastroscope 706 is preferably approximately 9.8 millimeters in length, and preferably has approximately a 2.8 millimeter working channel and suitable viewing and recording equipment, for example. It will be understood that tools and components that are described as being passed through or inserted into gastroscope 706 are passed through or inserted into its working channel. A lubricant such as Surgilube or equivalent may be provided as needed to lubricate the obesity device and/or any of the associated surgical equipment.

Gastroscope 706 should ultimately be positioned such that its distal end 708 is adjacent to pyloric sphincter 20. Preferably, a guidewire 722 is hydrated and inserted through gastroscope 706. Guidewire 722 is passed through pyloric sphincter 20, which may be aided by manipulation of gastroscope 706. It may also be beneficial to pass a distal end 708 of gastroscope 706 through pyloric sphincter 20 in order to maneuver guidewire 722 through same. There should preferably be at least about 30-40 centimeters of the length of guidewire 722 passed distally through pyloric sphincter 20 and into small intestine 40 so that any further movement of guidewire 722 during the insertion procedure does not result in the accidental removal of the distal end of guidewire 722 to a position proximal of pyloric sphincter 20. Of course, the length of guidewire 722 that should preferably be passed distally through pyloric sphincter 20 may vary according to different patients and/or procedures and may be less or more than 30-40 centimeters. After guidewire 722 is appropriately positioned, gastroscope 706 is removed from the patient.

Figure 34:
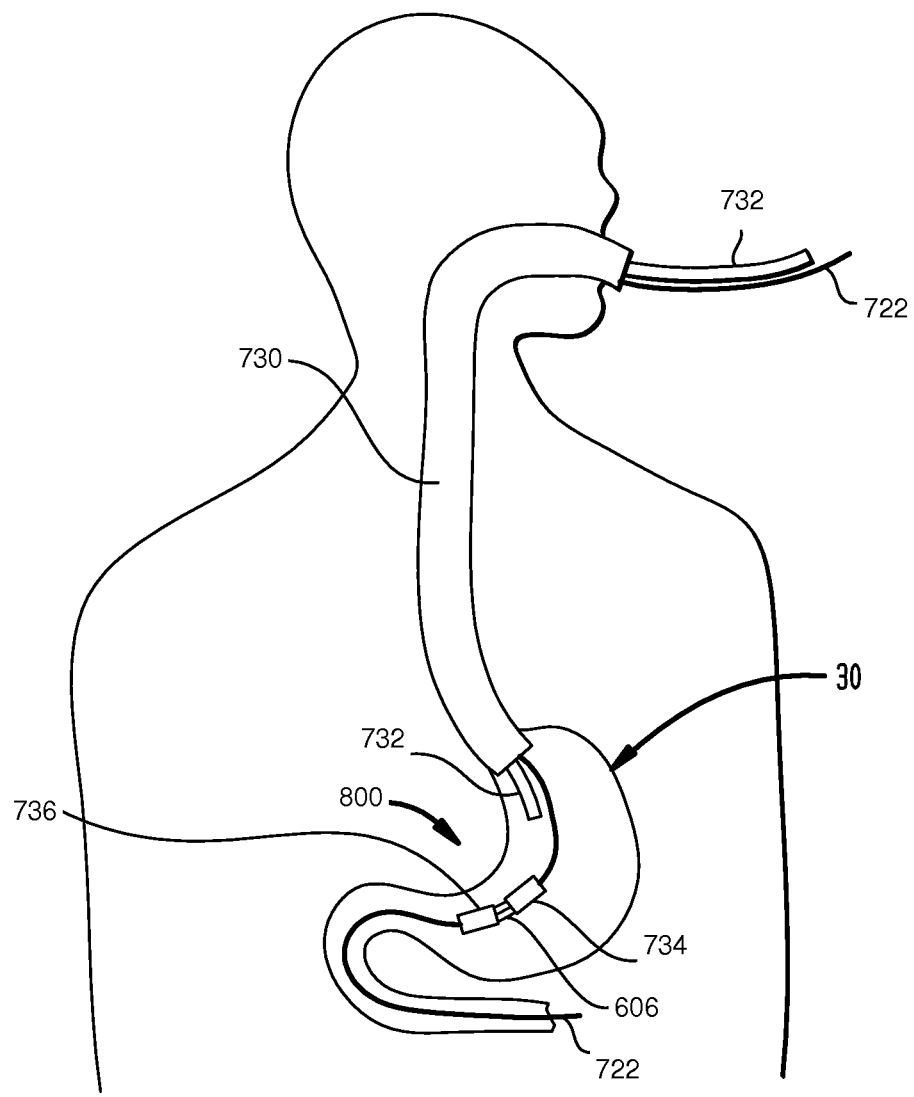
FIG. 34 illustrates the obesity device inserted into the stomach through an overtube in the esophagus of the patient.

Referring now to FIG. 34, an overtube 730 is positioned over the guidewire 722 and advanced through the esophagus and into the patient's stomach. Overtube 730 typically has an inner diameter of approximately 16 mm. Obesity device 800 is lubricated and positioned over the guidewire 722 outside of the patient. Once overtube 730 is positioned within stomach 30, a small steerable scope (not shown) is advanced through overtube 730 into stomach 30 through the pylorus and into the proximal portion of the duodenum. The scope is used to confirm the tissue of the stomach, pylorus and duodenum are robust and show not overt signs that they will not tolerate the device. In an exemplary embodiment, a small tube (not shown) may be inserted into the pylorus. The tube includes a distal inner tube-shaped balloon (not shown) that expands to a known diameter with a known volume of saline. In conjunction with the scope images and other prior imaging data, this instrument is used to determine the appropriate size of obesity device 800 to be used, particularly the appropriate size of anchor 604.

Once the appropriate size obesity device 800 is selected, a pusher rod 732 is used to push obesity device 800 into stomach 30. In the exemplary embodiment, flow restrictor 660 is encapsulated within a proximal capsule 734 and both anchor 604 and sleeve 608 are preferably encapsulated within a distal capsule 736 to help advance device 800 through overtube 730. It should be noted that it may not be necessary to encapsulate flow restrictor 660 and anchor 604 in order to advance them through overtube 730. In this case, these components will simply be advanced through overtube 730 in their deflated configurations.

Figure 35:
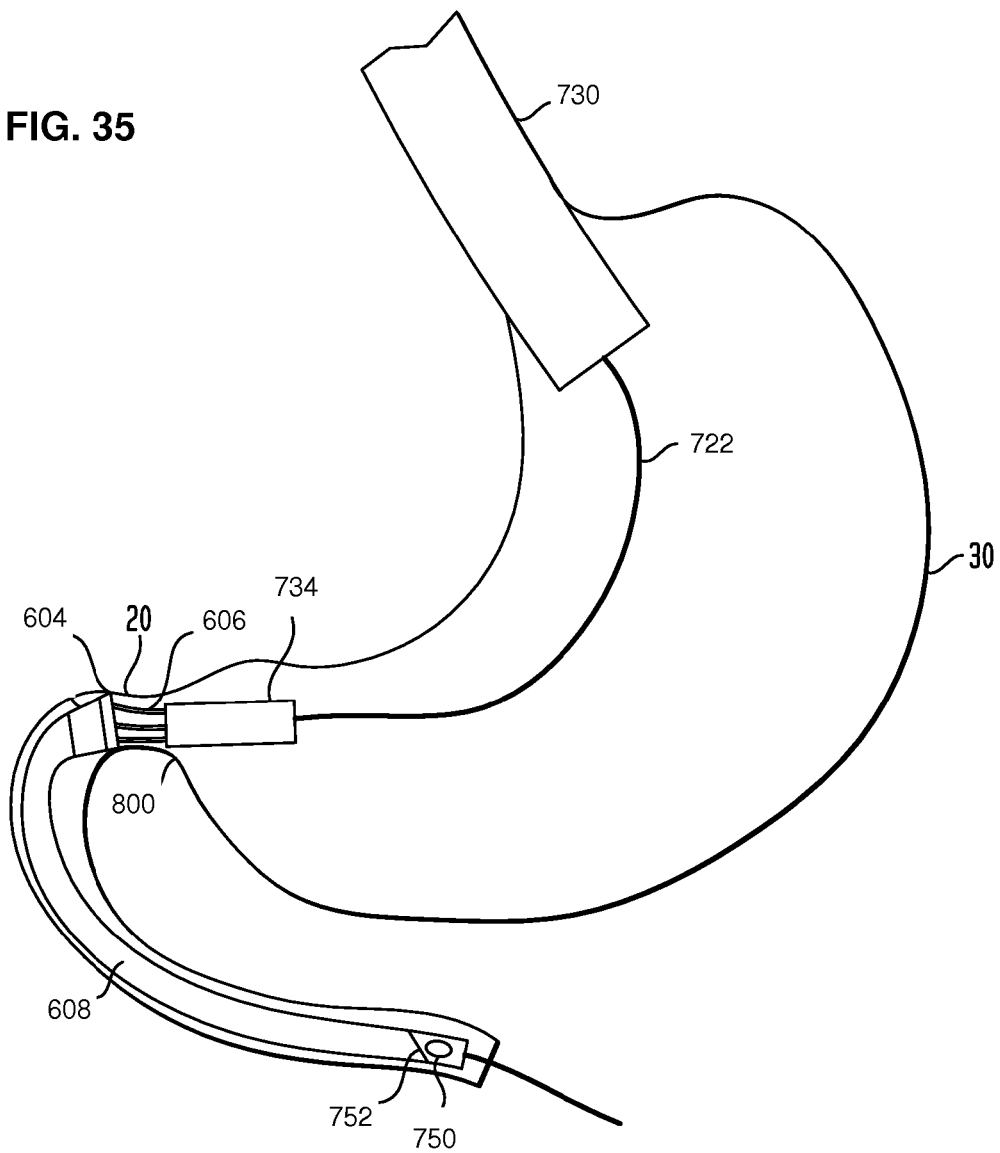
FIG. 35 illustrates the deployment of the anchor and the sleeve of obesity device into the small intestine of the patient.

Referring now to FIG. 35, distal capsule 736 is removed and anchor 630 and sleeve 608 are advanced with pusher rod 732 (not shown in FIG. 35) through the pylorus and into the proximal portion of the duodenum. This may require the use of a dilator (not shown) to maintain the pylorus in its maximum diameter. Once positioned properly, a fluid, such as saline or another appropriate fluid is injected through an external tube (not shown) and one-way valve into the expandable membrane to inflate the membrane to its expanded or operative configuration. The external tube would then be cut by a pair of scissors or other such instrument that can be advanced through the working channel of overtube 730. Alternatively, the fluid may be delivered through a syringe directly into the membrane or through an internal tube within the flow restrictor that is coupled to the interior of the membrane as described previously.

Once the anchor 630 has been inflated into its operative configuration, knob 750 at the distal end of sleeve 608 is grasped by a suitable grasping instrument and advanced downwardly through the duodenum and into the jejunum. When sleeve 608 has reached its maximum length, perforation 752 is torn and sleeve 608 is fully deployed. Knob 750 and perforation 752 can then be removed from the patient. Alternatively, sleeve 608 may be positioned either before anchor 630 has been inflated or after flow restrictor 660 has been inflated as described below.

Referring now to FIG. 36, proximal capsule 734 (shown in FIG. 35) is then disengaged from flow restrictor 660 and removed from the patient. A fluid, such as saline, is injected through inlet 680 (see FIG. 31) into the interior portion 664 of flow restrictor 660 to inflate flow restrictor 660 into its operative configuration. Obesity device 800 should now be in its final position with flow restrictor 660 in pyloric antrum 740 of stomach 30 and expandable membrane 642 of anchor 630 just distal to the pyloric sphincter 20. A gastroscope and/or fluoroscope (not shown) may be used to confirm the final placement of device 800. Once device 800 is in place, guidewire 722 and overtube 730 can be removed from the patient.

Figure 37:
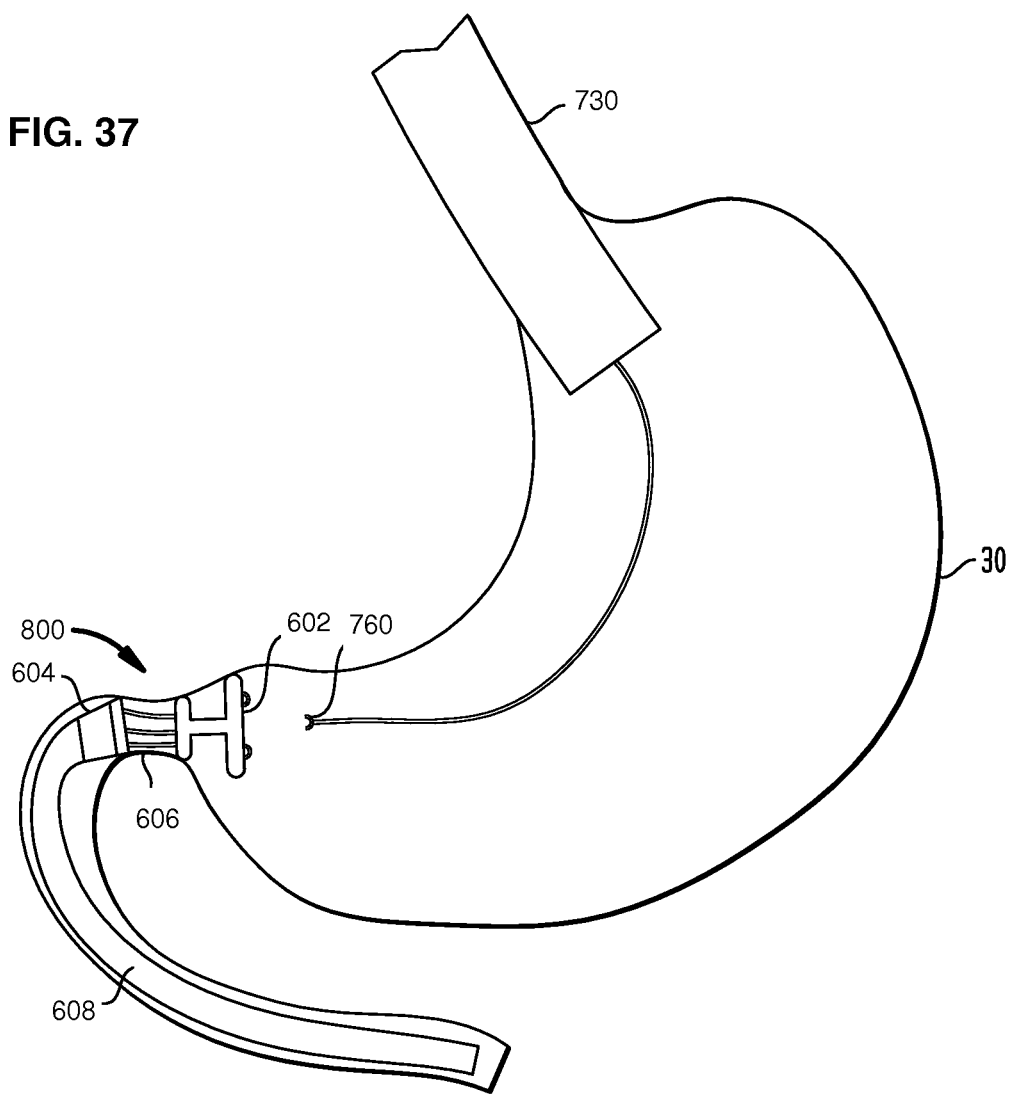
FIG. 37 illustrates the deflation of the flow restrictor in a step in the removal of the obesity device according to the present invention.
Figure 38:
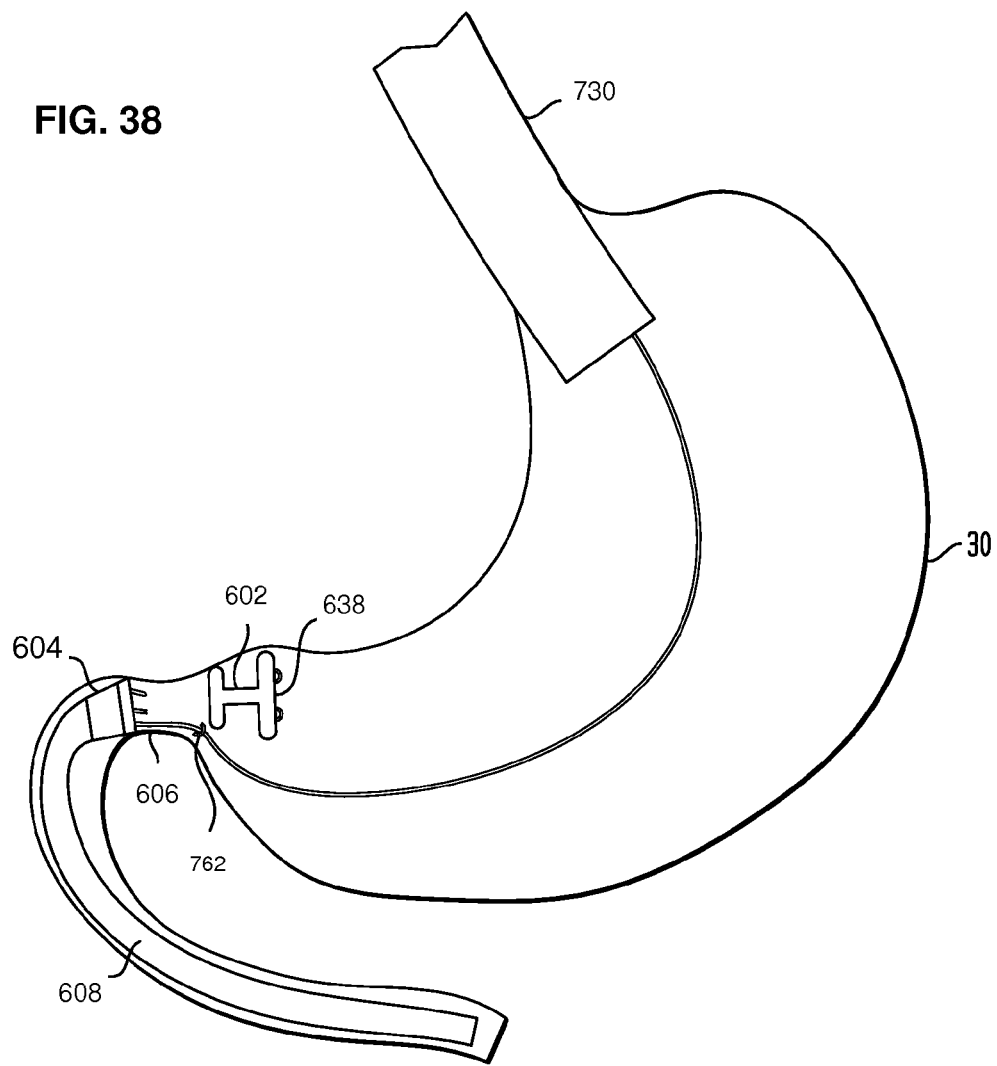
FIG. 38 illustrates the removal of the flow restrictor from the patient.
Figure 39:
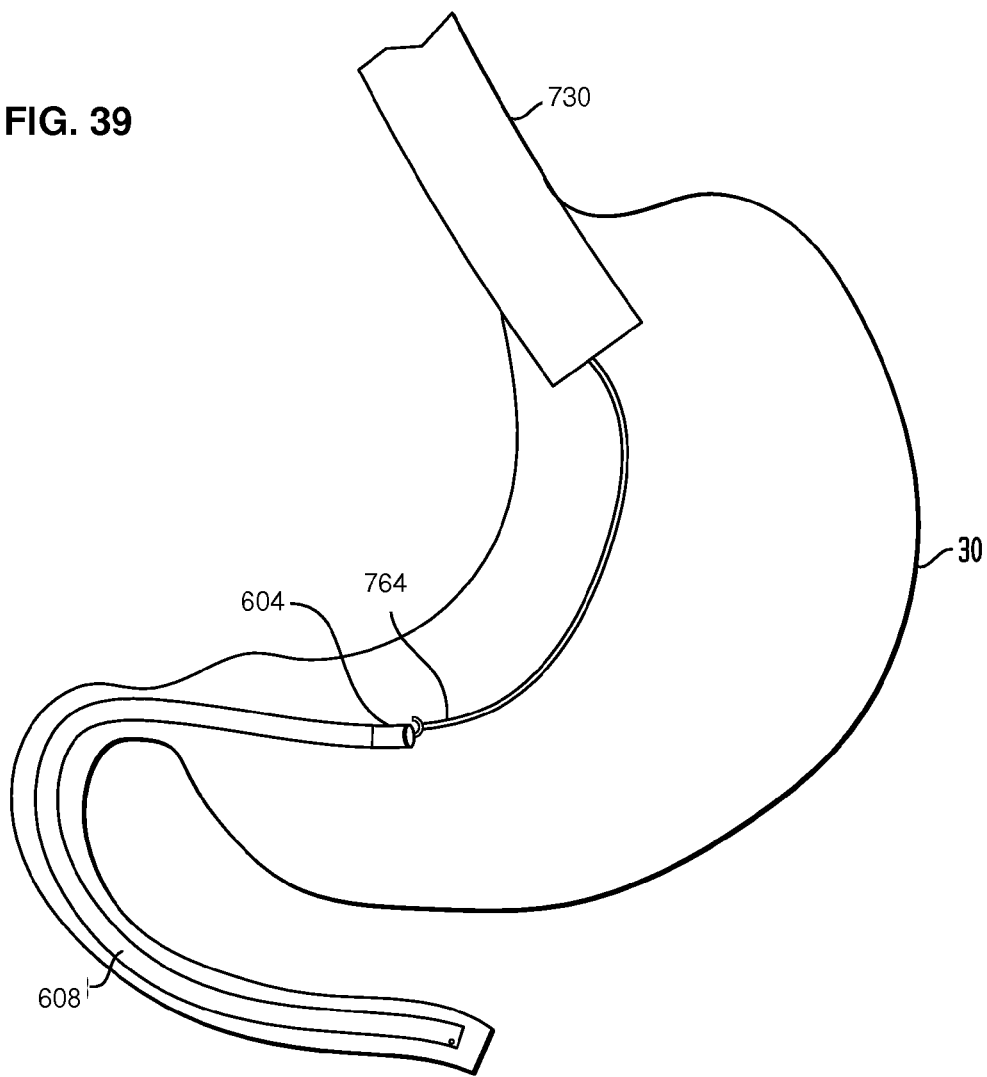
FIG. 39 illustrates the deflation of the anchor and removal of the remaining portions of the obesity device from the patient.

Referring now to FIGS. 37-39, a method for removing obesity device 800 according to the present invention will now be described. As shown in FIG. 29, overtube 730 is advanced through the esophagus and into position within the stomach 30 of patient and a gastroscope (not shown) is deployed through overtube 730 in a suitable position for the surgeon to view the procedure. A sharp instrument 760, such as scissors or the like, is advanced through overtube 730 into stomach 30. Sharp instrument 760 is used to puncture flow restrictor 660 such that the fluid within interior portion 664 of flow restrictor 660 exits interior portion 664 into the stomach to deflate flow restrictor 660. Alternatively, a syringe or similar suction device (not shown) may be attached to inlet 680 to withdraw the fluid from flow restrictor 660.

Referring now to FIG. 38, flow restrictor 660 is preferably positioned to the side of antrum 740. A grasping or cutting instrument 762 is advanced through overtube 730 to cut each of the pyloric columns 606 to detach flow restrictor 660 from the distal portion of device 800. The last column 606 that is severed will be held by grasping instrument 762 to ensure that anchor 630 and sleeve 608 do not migrate in the distal direction after being detached from flow restrictor 660. At this point, a grasping tool or snare (not shown) is advanced into stomach 30 to grab one or both of protuberances 638 on the proximal surface of flow restrictor 660. Flow restrictor 660 is then pulled through overtube 730 and removed from the patient.

Referring now to FIG. 39, a grasping instrument 764 is then advanced through the pyloric sphincter 20 to grasp a ball element attached to wire embedded in the inner membrane of the ring-inner tube structure. Grasping instrument 764 is pulled to cause the fluid within membrane 642 to exit membrane 642 and deflate anchor 630. Grasping instrument 764 may then be used to pull anchor 630 and sleeve 608 into stomach 30. In alternative embodiments, membrane 642 is fluidly coupled to a lumen (not shown) within flow restrictor 660 through one or more of the boss(es) 635 and column(s) 606. In these embodiments, cutting of the column(s) 606 will automatically deflate membrane 642.

Once anchor 630 and sleeve 608 are within stomach 30, they may be sliced up and removed or removed as a single unit. Subsequent to the removal of obesity device 800, a scope (not shown) can be used to determine if any tissue injury or insult that has been sustained by the implantation, use, or removal of device 800. Provided no additional access to the stomach, pylorus, or duodenum is required, removal of the scope and overtube 730 conclude the procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a wound in a diabetic patient comprising:
removably introducing an internal bypass device into a patient by advancing a duodenal anchor portion of the internal bypass device through an esophagus, a stomach and a pylorus into a duodenum of the patient;
extending a hollow sleeve of the internal bypass device through at least a portion of the duodenum;
advancing a gastric anchor portion of the internal bypass device through the esophagus and into the stomach of the patient;
spacing the duodenal anchor portion from the gastric anchor portion by at least 20 mm from each other; and
maintaining the hollow sleeve within the duodenum for a sufficient period of time to reduce a blood glucose level in the patient by inflating the duodenal anchor portion within the duodenum and inflating the gastric anchor portion within the stomach of the patient such that the hollow sleeve remains in position within the duodenum.

2. The method of claim 1 wherein the hollow sleeve is maintained within the duodenum for a sufficient period of time to increase peripheral vascular perfusion in the patient and accelerate healing of the wound.

3. The method of claim 1 wherein the hollow sleeve is maintained within the duodenum for a sufficient period of time to elevate an immune system response of the patient and accelerate healing of the wound.

4. The method of claim 1 wherein the hollow sleeve is maintained within the duodenum for a sufficient period of time to decrease insulin resistance within the patient.

5. The method of claim 1 wherein the hollow sleeve is maintained within the duodenum for a sufficient period of time to increase leukocyte activity in the patient.

6. The method of claim 1 wherein the hollow sleeve is maintained within the duodenum for a sufficient period of time to increase vascular endothelial growth factors in the patient's vascular tissue and accelerate healing of the wound.

7. The method of claim 1 wherein the hollow sleeve is maintained in the duodenum until the wound has closed.

8. The method of claim 1 wherein the blood glucose level is reduced to below 150 mg.

9. The method of claim 1 wherein the blood glucose level is reduced to below 125 mg.

10. The method of claim 1 wherein the internal bypass device is maintained within the duodenum for a sufficient period of time to reduce a fasting blood glucose level of the patient to below 99 mg.

11. The method of claim 1 wherein the wound is a diabetic foot ulcer.

12. The method of claim 1 wherein the maintaining step is carried out by anchoring the hollow sleeve in position within the duodenum.

13. The method of claim 1 wherein the internal bypass device is maintained within the duodenum for at least three weeks.

14. The method of claim 1 wherein the internal bypass device is maintained within the duodenum for at least two months.

15. A method of treating a chronic lower limb wound in a patient having a lack of innate ability to regulate glucose levels, comprising positioning a flexible sleeve between chyme exiting a stomach of the patient and at least a portion of an inner surface of the duodenum for a sufficient period of time to decrease a blood glucose level of the patient, wherein the positioning step comprises:
  advancing a duodenal anchor through an esophagus, a stomach and a pylorus into a duodenum of the patient;
  extending the flexible sleeve through at least a portion of the duodenum;
  advancing a gastric anchor through the esophagus and into the stomach of the patient;
  spacing the duodenal anchor and the gastric anchor at least 20 mm from each other; and
  maintaining the flexible sleeve within the duodenum by inflating the duodenal anchor within the duodenum and inflating the gastric anchor within the stomach of the patient such that the flexible sleeve remains in position within the duodenum.

16. The method of claim 15 wherein the sleeve is maintained in position within the duodenum until the blood glucose level of the patient is normalized.

17. The method of claim 15 wherein the sleeve is maintained in position within the duodenum until an increase in peripheral blood perfusion occurs within the patient.

18. The method of claim 15 wherein the sleeve is maintained in position within the duodenum until an increase in leukocyte activity occurs within the patient.

19. The method of claim 15 wherein the sleeve is maintained in position within the duodenum until the chronic lower limb wound is closed.

20. A method of increasing the perfusion of blood at the site of a chronic lower limb wound in a patient having a lack of innate ability to regulate glucose levels, comprising positioning a flexible sleeve between chyme exiting the patient's stomach and at least a portion of an inner surface of the patient's duodenum for a sufficient period of time that permits normalization of glucose levels in the patient, wherein the positioning step comprises:
  advancing a duodenal anchor through an esophagus, a stomach and a pylorus into a duodenum of the patient;
  extending the flexible sleeve through at least a portion of the duodenum;
  advancing a gastric anchor through the esophagus and into the stomach of the patient;
  spacing the gastric anchor and the duodenal anchor about 20-40 mm from each other; and
  maintaining the flexible sleeve within the duodenum by inflating the duodenal anchor within the duodenum and inflating the gastric anchor within the stomach of the patient such that the flexible sleeve remains in position within the duodenum.

* * * * *